United States Patent [19]
Vickery

[11] Patent Number: 5,821,225
[45] Date of Patent: *Oct. 13, 1998

[54] METHOD FOR THE TREATMENT OF CORTICOSTEROID INDUCED OSTEOPENIA COMPRISING ADMINISTRATION OF MODIFIED PTH OR PTHRP

[75] Inventor: Brian H. Vickery, Mountain View, Calif.

[73] Assignee: Syntex (U.S.A.) Inc., Palo Alto, Calif.

[ * ] Notice: The term of this patent shall not extend beyond the expiration date of Pat. No. 5,693,616.

[21] Appl. No.: 477,022

[22] Filed: Jun. 7, 1995

Related U.S. Application Data

[63] Continuation-in-part of Ser. No. 184,328, Jan. 18, 1994, which is a continuation-in-part of Ser. No. 915,247, Jul. 14, 1992, Pat. No. 5,589,452.

[51] Int. Cl.⁶ .......................... A61K 38/29; A61K 38/16
[52] U.S. Cl. .................................. 514/12; 514/2; 514/8; 514/13; 514/14; 514/15; 514/16; 514/17; 514/18; 514/19; 435/69.1
[58] Field of Search .............................. 514/2, 8, 12, 13, 514/14, 15, 16, 17, 18, 19; 435/69.1

[56] References Cited

U.S. PATENT DOCUMENTS

| | | | |
|---|---|---|---|
| 5,171,670 | 12/1992 | Kronenberg et al. | 435/68.1 |
| 5,229,489 | 7/1993 | Kanmera et al. | 530/324 |
| 5,317,010 | 5/1994 | Pang et al. | 514/12 |
| 5,382,658 | 1/1995 | Kronis et al. | 530/397 |
| 5,393,869 | 2/1995 | Nakagawa et al. | 530/324 |
| 5,434,246 | 7/1995 | Fukuda et al. | 530/324 |

OTHER PUBLICATIONS

Bowie et al. Science 247:1306–1310, 1990.

Adachi, et al., "Corticosteroid–Induced Osteoporosis", Semin. Arthritis Rheum., 22:6 (1993) pp. 375–384.

*Primary Examiner*—Elizabeth C. Kemmerer
*Attorney, Agent, or Firm*—Heller Ehrman White & McAuliffe

[57] ABSTRACT

Synthetic polypeptide analogs of parathyroid hormone PTH, parathyroid hormone related peptide PTHrp, and of the physiologically active truncated homologs and analogs of PTH and PTHrp, in which amino acid residues (22-31) form an amphipathic α-helix, said residues (22-31) selected from hydrophilic amino acids (Haa) and lipophilic amino acids (Laa) ordered in the sequence:

$$Haa(Laa\ Laa\ Haa\ Haa)_2\ Laa$$

and their pharmaceutically acceptable salts are useful for the prophylaxis and treatment of corticosteroid induced osteopenia in mammals.

9 Claims, 4 Drawing Sheets

METHOD FOR THE TREATMENT OF CORTICOSTEROID INDUCED OSTEOPENIA COMPRISING ADMINISTRATION OF MODIFIED PTH OR PTHRP

CROSS-REFERENCE TO RELATED APPLICATIONS

This application is a continuation-in-part of U.S. patent application Ser. No. 08/184,328, filed Jan. 18, 1994, which is a continuation-in-part of U.S. patent application Ser. No. 07/915,247, filed Jul. 14, 1992, now U.S. Pat. No. 5,589,452.

BACKGROUND OF THE INVENTION a) Field of the Invention

This invention relates to methods for the treatment of corticosteroid induced osteopenia via the administration of therapeutically effective amounts of certain novel analogs of parathyroid hormone and parathyroid hormone related peptide.

b) Description of Related Art

Osteoporosis is the most common form of metabolic bone disease and may be considered the symptomatic, fracture stage of bone loss (osteopenia). Although osteoporosis may occur secondary to a number of underlying diseases, 90% of all cases appear to be idiopathic. Postmenopausal women are particularly at risk for idiopathic osteoporosis (postmenopausal or Type I osteoporosis). Another high risk group for idiopathic osteoporosis is the elderly of either sex (senile or Type II osteoporosis). Osteoporosis has also been related to corticosteroid use, immobilization or extended bed rest, alcoholism, diabetes, gonadotoxic chemotherapy, hyperprolactinemia, anorexia nervosa, primary and secondary amenorrhea, and oophorectomy.

In the various forms of osteoporosis, bone fractures, which are the result of bone loss that has reached the point of mechanical failure, frequently occur. Postmenopausal osteoporosis is characterized by fractures of the wrist and spine, while femoral neck fractures seem to be the dominant feature of senile osteoporosis.

The mechanism by which bone is lost in osteoporotics is believed to involve an imbalance in the process by which the skeleton renews itself. This process has been termed bone remodeling. It occurs in a series of discrete pockets of activity. These pockets appear spontaneously within the bone matrix on a given bone surface as a site of bone resorption. Osteoclasts (bone dissolving or resorbing cells) are responsible for the resorption of a portion of bone of generally constant dimension. This resorption process is followed by the appearance of osteoblasts (bone forming cells) which then refill with new bone the cavity left by the osteoclasts.

In a healthy adult subject, the rate at which osteoclasts and osteoblasts are formed is such that bone formation and bone resorption are in balance. However, in osteoporotics an imbalance in the bone remodeling process develops which results in bone being lost at a rate faster than it is being made. Although this imbalance occurs to some extent in most individuals as they age, it is much more severe and occurs at a younger age in postmenopausal osteoporotics or following oophorectomy.

Adachi, et al. in *Seminars in Arthritis and Rheumatism*, 22:6, 375–84 (June 1993) report that despite much conflicting data regarding the pathophysiology of corticosteroid induced osteoporosis, it is generally agreed that there is a relative decrease in bone formation and a relative increase in bone resorption. Bone loss with resulting fractures and osteonecrosis is a frequent consequence of corticosteroid therapy. There is evidence that bone loss occurs rapidly within the first 6 to 12 months of corticosteroid therapy; there also appears to be a close relationship between rate of bone loss and corticosteroid dose. Men are equally susceptible to the effects of corticosteroids. The estimated incidence of fractures and osteonecrosis ranges from 30 to 50%.

There have been many attempts to treat osteoporosis with the goal of either slowing further bone loss or, more desirably, producing a net gain in bone mass. Certain agents, such as estrogen and the bisphosphonates, appear to slow further bone loss in osteoporotics. Agents which slow bone loss, because of the different durations of bone resorption and formation, may appear to increase bone mass (on the order of 3 to 7%). However, this apparent increase is limited in time, not progressive, and is due to a decrease in "remodeling space." In addition, because of the close coupling between resorption and formation, treatments which impede bone resorption also ultimately impede bone formation.

It has been suggested that treatment with parathyroid hormone (PTH) would lead to both increased bone turnover and a positive calcium balance. However, human clinical trials have shown that any increase in trabecular bone is offset by a decrease in cortical bone, so that there is no net increase in total bone.

Hefti, et al. in *Clinical Science* 62, 389–396 (1982) have reported that daily subcutaneous doses of either bPTH(1–84) or hPTH(1–34) increased whole body calcium and ash weight of individual bones in both normal and osteoporotic adult female rats.

Liu, et al. in *J. Bone Miner. Res.* 6:10, 1071–1080 (1991) have noted that ovariectomy of adult female rats induced a 47% loss in the percentage of trabecular bone in the proximal tibial metaphysis, accompanied by a significant increase in the number of osteoblasts and trabecular osteoclasts. Daily subcutaneous injections of hPTH(1–34) completely reversed the loss of trabecular bone and resulted in amounts of trabecular bone exceeding that of sham operated controls. The number of osteoblasts increased and the number of osteoclasts decreased.

Hock et al. in *J. Bone Min. Res.* 7:1, 65–71 (1992) have reported that daily subcutaneous injections of hPTH(1–34) to healthy adult male rats for 12 days increased trabecular and cortical bone calcium and dry weight. Total bone mass, trabecular bone volume, trabecular thickness and number, and osteoblastic surfaces were increased.

The mammalian parathyroid hormones, e.g. human (hPTH), bovine (bPTH), and porcine (pPTH), are single polypeptide chains of 84 amino acid residues, with molecular weights of approximately 9500. Biological activity is associated with the N-terminal portion, with residues (1–34) apparently the minimum required.

The N-terminal segment of human PTH differs from the N-terminal segment of the bovine and porcine hormones by only three and two amino acid residues, respectively:

hPTH(1–34):
Ser Val Ser Glu Ile Gln Leu Met His Asn Leu Gly Lys His Leu
 1           5              10              15
Asn Ser Met Glu Arg Val Glu Trp Leu Arg Lys Lys Leu Gln Asp
              20              25              30
Val His Asn Phe (SEQ ID NO:1);

-continued bPTH(1–34):

| Ala | Val | Ser | Glu | Ile | Gln | Phe | Met | His | Asn | Leu | Gly | Lys | His | Leu |
|-----|-----|-----|-----|-----|-----|-----|-----|-----|-----|-----|-----|-----|-----|-----|
| 1   |     |     |     | 5   |     |     |     |     | 10  |     |     |     |     | 15  |
| Ser | Ser | Met | Glu | Arg | Val | Glu | Trp | Leu | Arg | Lys | Lys | Leu | Gln | Asp |
|     |     |     |     | 20  |     |     |     |     | 25  |     |     |     |     | 30  |
| Val | His | Asn | Phe | (SEQ ID NO:2); | pPTH(1–34):

| Ser | Val | Ser | Glu | Ile | Gln | Leu | Met | His | Asn | Leu | Gly | Lys | His | Leu |
|-----|-----|-----|-----|-----|-----|-----|-----|-----|-----|-----|-----|-----|-----|-----|
| 1   |     |     |     | 5   |     |     |     |     | 10  |     |     |     |     | 15  |
| Ser | Ser | Leu | Glu | Arg | Val | Glu | Trp | Leu | Arg | Lys | Lys | Leu | Gln | Asp |
|     |     |     |     | 20  |     |     |     |     | 25  |     |     |     |     | 30  |
| Val | His | Asn | Phe | (SEQ ID NO:3). |

The primary function of PTH is to elicit the adaptive changes that serve to maintain a constant concentration of $Ca^{2+}$ in the extracellular fluid. PTH acts on the kidneys to increase tubular reabsorption of $Ca^{2+}$ from the urine, as well as stimulating the conversion of calcifediol to calcitriol, which is responsible for absorption of $Ca^{2+}$ from the intestines. One prominent effect is to promote the mobilization of $Ca^{2+}$ from bone. PTH acts on bone to increase the rate of resorption of $Ca^{2+}$ and phosphate. PTH stimulates the rate of bone resorption by osteoclasts, increases the rate of differentiation of mesenchymal cells to osteoclasts, and prolongs the half life of these latter cells. With prolonged action of PTH the number of bone forming osteoblasts is also increased; thus, the rate of bone turnover and remodeling is enhanced. However, individual osteoblasts appear to be less active than normal Rosenblatt, et al. in U.S. Pat. Nos. 4,423,037, 4,968,669 and 5,001,223 have disclosed PTH antagonists obtained by the deletion of the N-terminal (1–6) amino acids and the selective replacement of $Phe^7$, $Met^{8,18}$, and $Gly^{12}$. $Tyr^{34}$-$NH_2$ reportedly increased the activity and stability of these compounds.

Parathyroid hormone-related peptide (PTHrp), a 140+ amino acid protein, and fragments thereof, reproduce the major biological actions of PTH. PTHrp is elaborated by a number of human and animal tumors and other tissues and may play a role in hypercalcemia of malignancy. The sequence of hPTHrp (1–34) is as follows:

| Ala | Val | Ser | Glu | His | Gln | Leu | Leu | His | Asp | Lys | Gly | Lys | Ser | Ile |
|-----|-----|-----|-----|-----|-----|-----|-----|-----|-----|-----|-----|-----|-----|-----|
| 1   |     |     |     | 5   |     |     |     |     | 10  |     |     |     |     | 15  |
| Gln | Asp | Leu | Arg | Arg | Arg | Phe | Phe | Leu | His | His | Leu | Ile | Ala | Glu |
|     |     |     |     | 20  |     |     |     |     | 25  |     |     |     |     | 30  |
| Ile | His | Thr | Ala | (SEQ ID NO:4). |

The sequence homology between hPTH and hPTHrp is largely limited to the 13 N-terminal residues, 8 of which are identical; only 1 of 10 amino acids in the (25–34) receptor binding region of hPTH is conserved in hPTHrp. Conformational similarity may underlie the common activity. Cohen, et al. in *J. Biol. Chem.* 266:3, 1997–2004 (1991) have suggested that much of the sequence of PTH(1–34) and PTHrp(1–34), in particular regions (5–18) and (21–34), assumes an α-helical configuration, while noting that there is some question whether this configuration prevails for the carboxyl terminal end under physiological conditions. Such a secondary structure may be important for lipid interaction, receptor interaction, and/or structural stabilization.

We have synthesized analogs of PTH and of PTHrp with the objective of developing improved therapeutic agents for the restoration of bone mass in mammalian subjects, including those afflicted with osteoporosis.

SUMMARY OF THE INVENTION

This invention provides a method for treating corticosteroid induced osteopenia, which method comprises administering to a subject in need thereof an effective amount of a synthetic polypeptide analog of parathyroid hormone (PTH), parathyroid hormone related peptide (PTHrp), or of a physiologically active truncated homolog or analog of PTH or PTHrp, or salt thereof, in which amino acid residues (22–31) form an amphipathic α-helix, said residues (22–31) selected from hydrophilic amino acids (Haa) and lipophilic amino acids (Laa), ordered in the sequence:

Haa (Laa Laa Haa Haa)$_2$ Laa.

In one embodiment the sequence of amino acid residues (22–31) is selected from (SEQ ID NOS: 85, 86, 26, 27, 28, 29, and 30). The effective amount of polypeptide is from about 0.002 μg of polypeptide/kg of patient body mass/day to about 10 μg of polypeptide/kg of patient body mass/day.

Also provided are pharmaceutical compositions for the prevention or treatment of corticosteroid induced osteopenia comprising an effective amount of a synthetic polypeptide analog of parathyroid hormone (PTH), parathyroid hormone related peptide (PTHrp), or of a physiologically active truncated homolog or analog of PTH or PTHrp, or salt thereof, in which amino acid residues (22–31) form an amphipathic α-helix, said residues (22–31) selected from hydrophilic amino acids (Haa) and lipophilic amino acids (Laa), ordered in the sequence:

Haa (Laa Laa Haa Haa)$_2$ Laa, and a pharmaceutically acceptable carrier.

In one embodiment the pharmaceutical compositions are provided in unit dosage form for treating corticosteroid induced osteopenia comprising from about 1 μg to about 1000 μg of the synthetic polypeptide analog of parathyroid hormone (PTH), parathyroid hormone related peptide (PTHrp), or of a physiologically active truncated homolog or analog of PTH or PTHrp, or salt thereof, in which amino acid residues (22–31) form an amphipathic α-helix, said residues (22–31) selected from hydrophilic amino acids (Haa) and lipophilic amino acids (Laa), ordered in the sequence:

Haa (Laa Laa Haa Haa)$_2$ Laa, and a pharmaceutically acceptable carrier.

When specific illustrative embodiment of this sequence type are inserted into PTH, PTHrp, and the physiologically active truncated analogs and homologs of PTH and PTHrp, the resulting polypeptides are effective bone remodeling agents.

In one aspect, then, this invention provides methods of treating corticosteroid induced osteopenia with analogs of PTH, PTHrp, and the physiologically active truncated analogs and homologs of PTH and PTHrp, or salts thereof, in which amino acid residues (22–31) form an amphipathic α-helix, the sequence of said residues (22–31) selected from: a)

| $Xaa^1$ | $Xaa^2$ | Leu | $Xaa^4$ | $Xaa^5$ | Leu | $Xaa^7$ | $Xaa^8$ | $Xaa^9$ | $Xaa^{10}$ |
|---------|---------|-----|---------|---------|-----|---------|---------|---------|------------|
| 1       |         |     |         | 5       |     |         |         |         | 10         | wherein $Xaa^1$ and $Xaa^4$ are independently Glu, Glu(OCH$_3$), His, or Phe; $Xaa^2$ is Leu or Phe; $Xaa^5$ is Lys or His; $Xaa^7$ and $Xaa^{10}$ are independently Leu or Ile; $Xaa^8$ is Ala, Arg, or Glu; and $Xaa^5$ is Lys or Glu (SEQ ID NO:85); preferably Glu Leu Leu Glu Lys Leu Leu Xaa Lys Leu
1                5                  10 wherein Xaa is Glu or Arg (SEQ ID NO:26); b)

Xaa¹ Xaa² Leu Xaa⁴ Arg Leu Leu Xaa⁸ Arg Leu
1                5                       10 wherein Xaa¹ and Xaa⁴ are independently Glu, Glu(OCH₃), His, or Phe; Xaa² is Leu or Phe; Xaa⁸ is Glu, Lys, or Lys(COCH₂PEGX) and PEGX is a poly-(ethylene glycol methyl ether) radical of molecular weight 100 to 10,000 (SEQ ID NO:86); preferably, Glu Leu Leu Glu Arg Leu Leu Xaa Arg Leu
1                5                  10 wherein Xaa is Glu, Lys, or Lys(COCH₂PEGX) and PEGX is a poly-(ethylene glycol methyl ether) radical of molecular weight 100 to 10,000 (SEQ ID NO:27); c)

Ala Leu Ala Glu Ala Leu Ala Glu Ala Leu (SEQ ID NO:28);
1                5                  10 d)

Ser Leu Leu Ser Ser Leu Leu Ser Ser Leu (SEQ ID NO:29);
1                5                  10 e)

Ala Phe Tyr Asp Lys Val Ala Glu Lys Leu (SEQ ID NO:30).
1                5                  10

In another aspect, this invention provides pharmaceutical compositions of analogs of PTH, PTHrp, and of the physiologically active truncated homologs and analogs of PTH and PTHrp, or salts thereof, in which amino acid residues (22–31) form an amphipathic α-helix, the sequence of said residues (22–31) selected from: a)

Glu Leu Leu Glu Lys Leu Leu Xaa Lys Leu
1                5                  10 wherein Xaa is Glu or Arg (SEQ ID NO:26); b)

Glu Leu Leu Glu Arg Leu Leu Xaa Arg Leu
1                5                  10 wherein Xaa is Glu, Lys, or Lys(COCH₂PEGX) and PEGX is a poly-(ethylene glycol methyl ether) radical of molecular weight, 100 to 10,000 (SEQ ID NO:27); c)

Ala Leu Ala Glu Ala Leu Ala Glu Ala Leu (SEQ ID NO:28);
1                5                  10 d)

Ser Leu Leu Ser Ser Leu Leu Ser Ser Leu (SEQ ID NO:29);
1                5                  10 e)

Ala Phe Tyr Asp Lys Val Ala Glu Lys Leu (SEQ ID NO:30).
1                5                  10

Also provided are processes for preparing pharmaceutical compositions which comprise mixing the above described compounds with a pharmaceutically acceptable carrier.

DETAILED DESCRIPTION OF THE INVENTION

Abbreviations and Definitions

Figure 1:
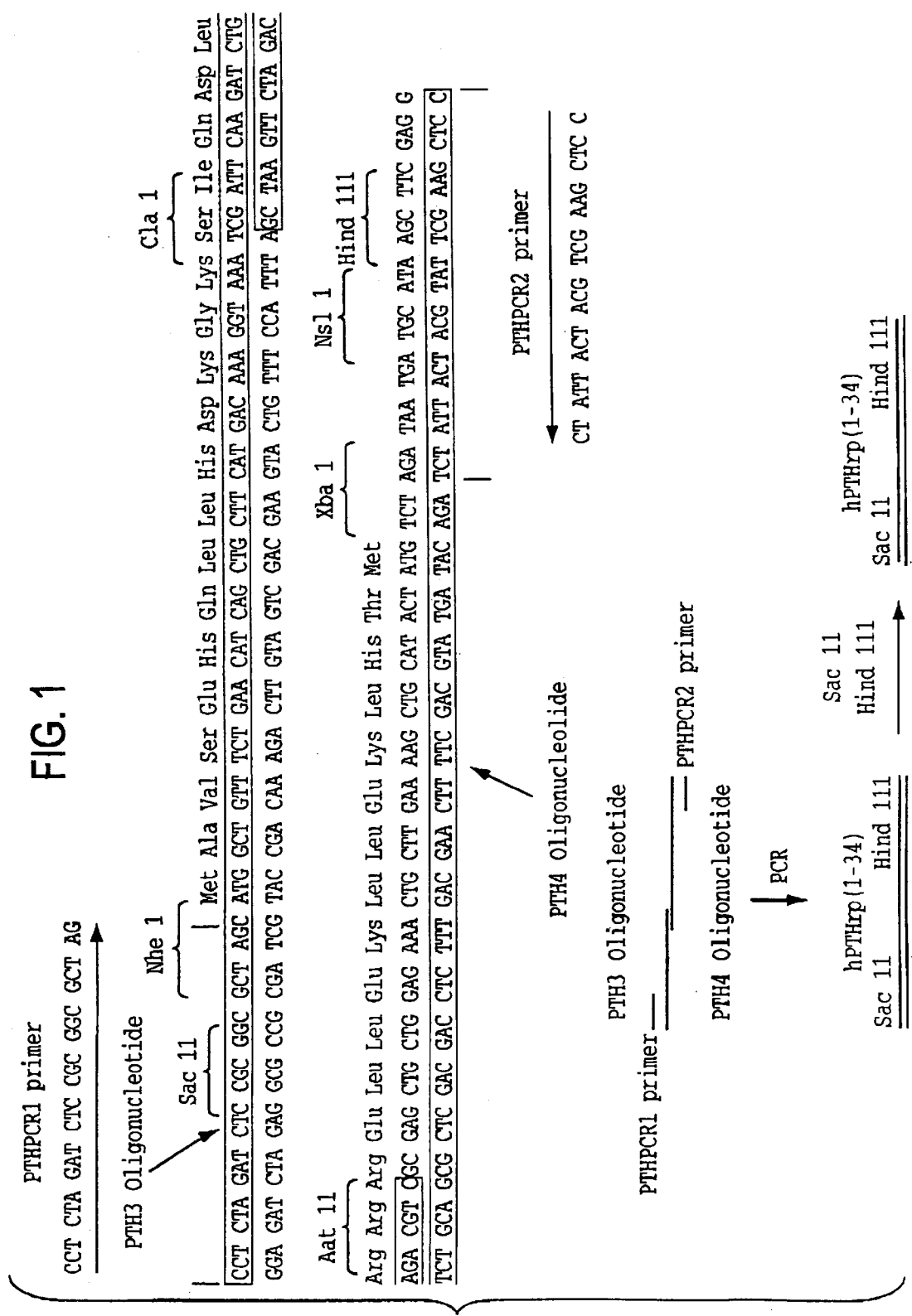
FIG. 1 presents the DNA sequence and enzyme restriction sites of a synthetic gene coding for a PTHrp(1–34) analog of this invention (SEQ ID NO:9).

The one- and three-letter abbreviations for the various common nucleotide bases and amino acids are as recommended in *Pure Appl. Chem.* 31, 639–645 (1972) and 40, 277–290 (1974) and the IUPAC-IUB Biochemical Nomenclature Commission and comply with 37 CFR §1.822 (55 FR 18245, May 1, 1990). The one- and three-letter abbreviations are as follows:

| Amino Acid Abbreviations | | |
|---|---|---|
| Amino Acid | Three-letter Symbol | One-letter Symbol |
| Alanine | Ala | A |
| Arginine | Arg | R |
| Asparagine | Asn | N |
| Aspartic Acid | Asp | D |
| Asn + Asp | Asx | B |
| Cysteine | Cys | C |
| Glutamine | Gln | Q |
| Glutamic Acid | Glu | E |
| Gln + Glu | Glx | Z |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |
| Other amino acid | Xaa | X |

The abbreviations represent L-amino acids unless otherwise designated as D- or D,L- Certain amino acids, both natural and non-natural, are achiral, e.g. glycine. All peptide sequences are presented with the N-terminal amino acid on the left and the C-terminal amino acid on the right.

Further abbreviations for other amino acids and compounds used herein are:

| | |
|---|---|
| hSer | homoserine |
| hSerlac | homoserine lactone |
| Nle | norleucine |
| PEG2 | radical of diethylene glycol methyl ether, a.k.a. methoxydi (ethyleneoxy), $CH_3O(CH_2CH_2O)_2$-, (MW = 119) |
| PEG5000 | radical of poly(ethylene glycol methyl ether), a.k.a. methoxypoly(ethyleneoxy), $CH_3O(CH_2CH_2O)_{110}$-, (avg. MW = 5000) |
| PEGX | radical of poly(ethylene glycol methyl ether), $CH_3O(CH_2CH_2O)_n$-, = 2 – 225, (avg. MW = 100 to 10,000) |

"Hydrophilic amino acid (Haa)" refers to an amino acid having at least one hydrophilic functional group in addition to those required for peptide bond formation, such as arginine, asparagine, aspartic acid, glutamic acid, glutamine, histidine, lysine, serine, threonine, and their homologs.

"Lipophilic amino acid (Laa)" refers to an uncharged, aliphatic or aromatic amino acid, such as isoleucine, leucine, methionine, phenylalanine, tryptophan, tyrosine, valine, and their homologs.

For the purposes of this invention, alanine is classified as "amphiphilic" i.e., capable of acting as either hydrophilic or lipophilic.

"Physiologically active truncated homolog or analog of PTH or PTHrp" refers to a polypeptide having a sequence comprising less than the full complement of amino acids found in PTH or PTHrp which, however, elicits a similar physiological response. The truncated PTH or PTHrp need not be fully homologous with PTH or PTHrp to elicit a similar physiological response. PTH(1–34) and PTHrp (1–34) are preferred, but not exclusive, representatives of this group.

"Amphipathic α-helix" refers to the secondary structure exhibited by certain polypeptides in which the amino acids assume an α-helical configuration having opposing polar and nonpolar faces oriented along the long axis of the helix. The possibility of α-helical structure in the polypeptide of interest may be explored to some extent by the construction of a "Schiffer-Edmundson wheel" (M. Schiffer and A. B. Edmundson, *Biophys. J.* 7, 121 (1967)), of the appropriate pitch and noting the segregation of the hydrophilic and lipophilic residues on opposite faces of the cylinder circumscribing the helix. Alternatively, empirical evidence, such as circular dichroism or x-ray diffraction data, may be available indicating the presence of an α-helical region in a given polypeptide. An ideal α-helix has 3.6 amino acid residues per turn with adjacent side chains separated by 100° of arc. Eisenberg et al. in *Nature* 299:371–374 (1982) and *Proc. Nat. Acad. Sci. USA* 81:140–144 (1984) have combined a hydrophobicity scale with the helical wheel to quantify the concept of amphipathic helices. The mean hydrophobic moment is defined as the vector sum of the hydrophobicities of the component amino acids making up the helix. The following hydrophobicities for the amino acids are those reported by Eisenberg (1984) as the "consensus" scale:

Ile 0.73; Phe 0.61; Val 0.54; Leu 0.53; Trp 0.37;
Met 0.26 Ala 0.25; Gly 0.16; Cys 0.04; Tyr 0.02;
Pro –0.07; Thr –0.18; Ser –0.26; His –0.40; Glu –0.62;
Asn –0.64; Gln –0.69; Asp –0.72; Lys –1.10; Arg –1.76.

The hydrophobic moment, $\mu_H$, for an ideal α-helix having 3.6 residues per turn (or a 100° arc (=360°/3.6) between side chains), may be calculated from:

$$\mu_H = [(\Sigma H_N \sin\delta(N-1))^2 + (\Sigma H_N \cos\delta(N-1))^2]^{1/2},$$

where $H_N$ is the hydrophobicity value of the $N^{th}$ amino acid and the sums are taken over the N amino acids in the sequence with periodicity δ=100°. The hydrophobic moment may be expressed as the mean hydrophobic moment per residue by dividing $\mu_H$ by N to obtain $<\mu_H>$. A value of $<\mu_H>$ at 100°±20° of about 0.20 or greater is suggestive of amphipathic helix formation. The $<\mu_H>$ values at 100° for hPTHrp (22–31) and hPTH (22–31) are 0.19 and 0.37, respectively.

Cornett, et al., in *J. Mol. Biol.*, 195:659–685 (1987) have further extended the study of amphiphathic α-helices by introducing the "amphipathic index" as a predictor of amphipathicity. They concluded that approximately half of all known α-helices are amphipathic, and that the dominant frequency is 97.5° rather than 100°, with the number of residues per turn being closer to 3.7 than 3.6. While such refinements are scientifically interesting, the basic approach of Eisenberg, et al. is sufficient to classify a given sequence as amphipathic, particularly when one is designing a sequence ab initio to form an amphipathic α-helix.

A substitute amphipathic α-helical amino acid sequence may lack homology with the sequence of a given segment of a naturally occurring polypeptide but elicits a similar secondary structure, i. e. an α-helix having opposing polar and nonpolar faces, in the physiological environment. Replacement of the naturally occurring amino acid sequence with an alternative sequence may beneficially affect the physiological activity, stability, or other properties of the altered parent polypeptide. Guidance as to the design and selection of such sequences is provided in J. L. Krstenansky, et al., *FEBS Letters* 242:2, 409–413 (1989), and J. P. Segrest, et al. *Proteins: Structure, Function, and Genetics* 8:103–117 (1990) among others.

The ten amino acid amphipathic α-helix of this invention has the formula:

Haa (Laa Laa Haa Haa)$_2$ Laa wherein the Haa's are selected from the group of hydrophilic amino acids and the Laa's are selected from the group of lipophilic amino acids, as defined above. Assuming an idealized α-helix, residues 1, 4, 5, 8, and 9 are distributed along one face (A) of the helix within about a 140° arc of each other, while residues 2, 3, 6, 7, and 10 occupy an opposing 1400 arc on the other face (B) of the helix. Preferably, all the residues on one face are of the same polarity while all those on the other face are of the opposite polarity, i.e., if face A is all hydrophilic, face B is all lipophilic and vice versa. The skilled artisan will recognize that while the helices of this invention are described by Haa(Laa Laa Haa Haa)$_2$ Laa, the reverse sequence, Laa (Haa Haa Laa Laa)$_2$ Haa will also meet the residue distribution criteria and is an equivalent descriptor of the helices of this invention.

Alanine may be substituted for either hydrophilic or lipophilic amino acids, since Ala can reside readily on either face of an amphipathic α-helix, although Ala$_{10}$ does not form an amphipathic α-helix. Generally, proline, cysteine, and tyrosine are not used; however, their presence and other random errors in the sequence may be tolerated, e.g. a hydrophilic residue on the lipophilic face, as long as the remaining amino acids in the segment substantially conform to the hydrophilic face—lipophilic face division. A convenient method for determining if a sequence is sufficiently amphipathic to be a sequence of this invention is to calculate the mean hydrophobic moment, as defined above. If the peak mean moment per residue at 100°±20° exceeds about 0.20, then the sequence will form an amphipathic helix and is a sequence of this invention.

For example, the mean hydrophobic moment per residue at 100° for (SEQ ID NO: 26), Xaa=Glu, is calculated as follows:

| A.A. | $H_N$ | $\delta (N-1)$ | $H \sin \delta (N-1)$ | $H \cos \delta (N-1)$ |
|---|---|---|---|---|
| E | −.62 | 0 | 0 | −.62 |
| L | .53 | 100 | .52 | −.17 |
| L | .53 | 200 | −.18 | −.50 |
| E | −.62 | 300 | .34 | −.31 |
| K | −1.1 | 400 | −.70 | −.85 |
| L | .53 | 500 | .34 | −.41 |
| L | .53 | 600 | −.46 | −.27 |
| E | −.62 | 700 | .21 | −.58 |
| K | −1.1 | 800 | −1.08 | −.19 |
| L | .53 | 900 | 0 | −.53 |

$$\Sigma = 0.81 \qquad \Sigma = -4.43$$
$$\mu_H = [(0.81)^2 + (-4.43)^2]^{1/2} = 4.50$$
$$<\mu_H> = 4.50/10 = 0.45$$

For this sequence, the mean peak hydrophobic moment occurs at 92° and has a value of 0.48.

In applying this concept to parathyroid hormone and parathyroid hormone related peptide, it was hypothesized that either or both regions (7–16) and (22–31) may exhibit α-helical secondary structure and could be replaced with a non-homologous sequence having similar structural tendencies, without loss of biological activity or induction of immunoreaction.

Preferred Embodiments

In one aspect, this invention provides analogs of PTH, PTHrp, and the physiologically active truncated analogs and homologs of PTH and PTHrp, or salts thereof, in which amino acid residues (22–31) form an amphipathic α-helix, the sequence of said residues (22–31) selected from: a)

$Xaa^1\ Xaa^2\ Leu\ Xaa^4\ Xaa^5\ Leu\ Xaa^7\ Xaa^8\ Xaa^9\ Xaa^{10}$
1                5                           10 wherein $Xaa^1$ and $Xaa^4$ are independently Glu, Glu(OCH$_3$), His, or Phe; $Xaa^2$ is Leu or Phe; $Xaa^5$ is Lys or His; $Xaa^7$ and $Xaa^{10}$ are independently Leu or Ile; $Xaa^8$ is Ala, Arg, or Glu; and $Xaa^9$ is Lys or Glu (SEQ ID NO: 85); preferably Glu Leu Leu Glu Lys Leu Leu Xaa Lys Leu
1                5                           10 wherein Xaa is Glu or Arg (SEQ ID NO:26); b)

$Xaa^1\ Xaa^2\ Leu\ Xaa^4\ Arg\ Leu\ Leu\ Xaa^8\ Arg\ Leu$
1                5                           10 wherein $Xaa^1$ and $Xaa^4$ are independently Glu, Glu(OCH$_3$), His, or Phe; $Xaa^2$ is Leu or Phe; $Xaa^8$ is Glu, Lys, or Lys(COCH$_2$PEGX) and PEGX is a poly-(ethylene glycol methyl ether) radical of molecular weight 100 to 10,000 (SEQ ID NO:86); preferably, Glu Leu Leu Glu Arg Leu Leu Xaa Arg Leu
1                5                           10 wherein Xaa is Glu, Lys, or Lys(COCH$_2$PEGX) and PEGX is a poly(ethylene glycol methyl ether) radical of molecular weight; 100 to 10,000 (SEQ ID NO:27); c)

Ala Leu Ala Glu Ala Leu Ala Glu Ala Leu (SEQ ID NO:28);
1                5                           10 d)

Ser Leu Leu Ser Ser Leu Leu Ser Ser Leu (SEQ ID NO:29);
1                5                           10 e)

Ala Phe Tyr Asp Lys Val Ala Glu Lys Leu (SEQ ID NO:30).
1                5                           10

In another aspect, this invention provides analogs of PTH, PTHrp, and the physiologically active truncated analogs and homologs of PTH and PTHrp, or salts thereof, of the formula:

$Xaa^1\ Xaa^2\ Xaa^3\ Xaa^4\ Xaa^5\ Xaa^6\ Xaa^7\ Leu\ His\ Xaa^{10}\ Xaa^{11}$ Gly $Xaa^{13}$
Ser Ile Gln $Xaa^{17}$ Leu $Xaa^{19}\ Xaa^{20}\ Xaa^{21}\ Xaa^{22-31}\ Xaa^{32}\ Xaa^{33}\ Xaa^{34}$
$Xaa^{35}\ Xaa^{36}\ Xaa^{37}\ Xaa^{38}$ Term, wherein:

$Xaa^1$ is absent or is Ala;
$Xaa^2$ is absent or is Val;
$Xaa^3$ is absent or is Ser;
$Xaa^4$ is absent or is Glu or Glu(OCH$_3$);
$Xaa^5$ is absent or is His or Ala;
$Xaa^6$ is absent or is Gln;
$Xaa^7$ is absent or is Leu;
$Xaa^{10}$ and $Xaa^{17}$ are independently Asp or Asp(OCH$_3$);
$Xaa^{11}$ is Lys, Arg, or Leu;
$Xaa^{13}$ is Lys, Arg, Tyr, Cys, Leu, Cys(CH$_2$CONH(CH$_2$)$_2$NH(biotinyl)), Lys(7-dimethylamino-2-oxo-2H-1-benxopyran-4-acetyl), or Lys(dihydrocinnamoyl);
$Xaa^{20}$ is Arg or Leu;
$Xaa^{19}$ and $Xaa^{21}$ are independently Lys, Ala, or Arg;
$Xaa^{22-31}$ is selected from (SEQ ID NOS:26, 27, 28, 29, or 30);
$Xaa^{32}$ is His, Pro, or Lys;
$Xaa^{33}$ is absent, or is Pro, Thr, Glu, or Ala;
$Xaa^{34}$ is absent, or is Pro, Arg, Met, Ala, hSer, hser lactone, Tyr, Leu, or 1,4-diaminobutyryl lactam;
$Xaa^{35}$ is absent or is Pro, Glu, Ser, Ala, or Gly;
$Xaa^{36}$ is absent or is Ala, Arg, or Ile;
$Xaa^{37}$ is absent or is Arg, Trp, or 3-(-2-naphthyl)-L-alanine;
$Xaa^{38}$ is absent or is Ala or hSer or $Xaa^{38-42}$ is Thr Arg Ser Ala Trp;
and Term is OR or NR$_2$ where each R is independently H, (C$_1$–C$_4$)alkyl or phenyl(Cl-C$_4$)alkyl; and the pharmaceutically acceptable salts thereof.

In yet another aspect this invention includes polypeptide analogs of the physiologically active truncated homolog hPTHrp(1–34), as shown in Formula (I):

Ala Val Ser Glu $Xaa^5$ Gln Leu Leu His Asp $Xaa^{11}$ Gly $Xaa^{13}$ Ser
Ile Gln Asp Leu $Xaa^{19}$ Arg $Xaa^{21}$ $Xaa^{22-31}$ $Xaa^{32}$ $Xaa^{33}$ $Xaa^{34}$ Term, wherein:

$Xaa^5$ is His or Ala;
$Xaa^{11}$ and $Xaa^{13}$ are independently Lys, Arg, or Leu;
$Xaa^{19}$ and $Xaa^{21}$ are independently Ala or Arg;

Xaa$^{22\text{-}31}$ is selected from: a)

Glu Leu Leu Glu Lys Leu Leu Xaa Lys Leu
1               5                   10 wherein Xaa is Glu or Arg (SEQ ID NO:26); b)

Glu Leu Leu Glu Arg Leu Leu Xaa Arg Leu
1               5                   10 wherein Xaa is Glu, Lys, or Lys(COCH$_2$PEGX) and PEGX is a poly(ethylene glycol methyl ether) radical of molecular weight 100 to 10,000 (SEQ ID NO:27); c)

Ala Leu Ala Glu Ala Leu Ala Glu Ala Leu (SEQ ID NO:28);
1               5               10 d)

Ser Leu Leu Ser Ser Leu Leu Ser Ser Leu (SEQ ID NO:29);
1               5               10 e)

Ala Phe Tyr Asp Lys Val Ala Glu Lys Leu (SEQ ID NO:30);
1               5               10

Xaa$^{32}$ is His or Lys;
Xaa$^{33}$ is Thr, Glu, or Ala;
Xaa$^{34}$ is Ala, hSer, Tyr, or Leu;
and Term is Gly Arg Arg, lactone, OH or NR$_2$, where each R is H or (C$_1$–C$_4$) alkyl; and their pharmaceutically acceptable salts. (Formula I)

A more specific aspect of the invention includes those polypeptides of Formula (I) wherein Xaa$^{22\text{-}31}$ is (SEQ ID NO:26), for which $\langle\mu_H\rangle$ at 100° exceeds 0.45. A still more specific aspect of the invention includes those Formula (I) polypeptides wherein Xaa$^{22\text{-}31}$ is (SEQ ID NO:26); Xaa$^{11}$ and Xaa$^{13}$ are both Lys; and Xaa$^{19}$ and Xaa$^{21}$ are both Arg. Representative polypeptides include, but are not limited to:

Ala Val Ser Glu His Gln Leu Leu His Asp Lys Gly Lys Ser Ile
1               5                   10                  15
Gln Asp Leu Arg Arg Arg Glu Leu Leu Glu Lys Leu Leu Arg Lys
                20                  25                  30
Leu His Thr Ala OH (SEQ ID NO:5);

Ala Val Ser Glu His Gln Leu Leu His Asp Lys Gly Lys Ser Ile
1               5                   10                  15
Gln Asp Leu Arg Arg Arg Glu Leu Leu Glu Lys Leu Leu Glu Lys
                20                  25                  30
Leu His Thr Ala OH (SEQ ID NO:6);

Ala Val Ser Glu His Gln Leu Leu His Asp Lys Gly Lys Ser Ile
1               5                   10                  15
Gln Asp Leu Arg Arg Arg Glu Leu Leu Glu Lys Leu Leu Glu Lys
                20                  25                  30
Leu His Thr Ala NH$_2$ (SEQ ID NO:7);

Ala Val Ser Glu His Gln Leu Leu His Asp Lys Gly Lys Ser Ile
1               5                   10                  15
Gln Asp Leu Arg Arg Arg Glu Leu Leu Glu Lys Leu Leu Glu Lys
                20                  25                  30
Leu His Thr hSer NH$_2$ (SEQ ID NO:8);

Ala Val Ser Glu His Gln Leu Leu His Asp Lys Gly Lys Ser Ile
1               5                   10                  15
Gln Asp Leu Arg Arg Arg Glu Leu Leu Glu Lys Leu Leu Glu Lys
                20                  25                  30
Leu His Thr hSerlac (SEQ ID NO:9);

Ala Val Ser Glu His Gln Leu Leu His Asp Lys Gly Lys Ser Ile
1               5                   10                  15
Gln Asp Leu Arg Arg Arg Glu Leu Leu Glu Lys Leu Leu Glu Lys
                20                  25                  30
Leu His Thr Ala Gly Arg Arg OH (SEQ ID NO:10); and
                35

Ala Val Ser Glu His Gln Leu Leu His Asp Lys Gly Lys Ser Ile
1               5                   10                  15
Gln Asp Leu Arg Arg Arg Glu Leu Leu Glu Lys Leu Leu Glu Lys
                20                  25                  30
Leu Lys Glu Leu NH$_2$ (SEQ ID NO:11).

Another aspect of this invention includes those polypeptides of Formula (I) wherein Xaa$^{22\text{-}31}$ is (SEQ ID NO:26); Xaa$^{11}$ and Xaa$^{13}$ are both Lys; and one of Xaa$^{19}$ and Xaa$^{21}$ is Arg and the other is Ala. Representative polypeptides of this subgenus include, but are not limited to:

Ala Val Ser Glu His Gln Leu Leu His Asp Lys Gly Lys Ser Ile
1               5                   10                  15
Gln Asp Leu Ala Arg Arg Glu Leu Leu Glu Lys Leu Leu Glu Lys
                20                  25                  30
Leu His Thr Ala NH$_2$ (SEQ ID NO:12) and Ala Val Ser Glu His Gln Leu Leu His Asp Lys Gly Lys Ser Ile
1               5                   10                  15
Gln Asp Leu Arg Arg Ala Glu Leu Leu Glu Lys Leu Leu Glu Lys
                20                  25                  30
Leu His Thr Ala NH$_2$ (SEQ ID NO:13).

In another aspect this invention includes those polypeptides of Formula (I) wherein Xaa$^{22\text{-}31}$ is (SEQ ID NO:26); one of Xaa$^{11}$ and Xaa$^{13}$ is Leu and the other is Lys; and Xaa$^{19}$ and Xaa$^{21}$ are both Arg. Representative polypeptides of this subgenus include, but are not limited to:

Ala Val Ser Glu Ala Gln Leu Leu His Asp Leu Gly Lys Ser Ile
1               5                   10                  15
Gln Asp Leu Arg Arg Arg Glu Leu Leu Glu Lys Leu Leu Glu Lys
                20                  25                  30
Leu His Ala Leu OH (SEQ ID NO:14).

In another aspect this invention includes those polypeptides of Formula (I) wherein Xaa$^{22\text{-}31}$ is (SEQ ID NO:27), for which $\langle\mu_H\rangle$ at 100° exceeds 0.50. A further aspect of this invention includes those Formula (I) polypeptides wherein Xaa$^{22\text{-}31}$ is (SEQ ID NO:27); Xaa$^{11}$ and Xaa$^{13}$ are both Lys or both Arg; and Xaa$^{19}$ and Xaa$^{21}$ are both Arg. Representative polypeptides of this subgenus include, but are not limited to:

Ala Val Ser Glu His Gln Leu Leu His Asp Lys Gly Lys Ser Ile
1                   5                        10                      15

Gln Asp Leu Arg Arg Arg Glu Leu Leu Glu Arg Leu Leu Glu Arg
                    20                      25                       30

Leu His Thr Ala OH (SEQ ID NO:15);

Ala Val Ser Glu His Gln Leu Leu His Asp Arg Gly Arg Ser Ile
1                   5                        10                      15

Gln Asp Leu Arg Arg Arg Glu Leu Leu Glu Arg Leu Leu Glu Arg
                    20                      25                       30

Leu His Thr Ala OH (SEQ ID NO:16);

Ala Val Ser Glu His Gln Leu Leu His Asp Arg Gly Arg Ser Ile
1                   5                        10                      15

Gln Asp Leu Arg Arg Arg Glu Leu Leu Glu Arg Leu Leu Lys Arg
                    20                      25                       30

Leu His Thr Ala OH (SEQ ID NO:17);

Ala Val Ser Glu His Gln Leu Leu His Asp Arg Gly Arg Ser Ile
1                   5                        10                      15

Gln Asp Leu Arg Arg Arg Glu Leu Leu Glu Arg Leu Leu
                    20                      25

Lys(COCH₂PEG2) Arg Leu His Thr Ala OH (SEQ ID NO:18)
                          30 and

Ala Val Ser Glu His Gln Leu Leu His Asp Arg Gly Arg Ser Ile
1                   5                        10                      15

Gln Asp Leu Arg Arg Arg Glu Leu Leu Glu Arg Leu Leu
                    20                      25

Lys(COCH₂PEG5000) Arg Leu His Thr Ala OH (SEQ ID NO:19).
                            30

In another aspect this invention includes polypeptides of Formula (I) wherein $Xaa^{22-31}$ is (SEQ ID NO:28), for which $<\mu_H>$ at 100° is about 0.25. Representative polypeptides of this subgenus include, but are not limited to:

Ala Val Ser Glu His Gln Leu Leu His Asp Lys Gly Lys Ser Ile
1                   5                        10                      15

Gln Asp Leu Arg Arg Ala Leu Ala Glu Ala Leu Ala Glu Ala
                    20                      25                       30

Leu His Thr Ala NH₂ (SEQ ID NO:20).

In another aspect this invention includes polypeptides of Formula (I) wherein $Xaa^{22-31}$ is (SEQ ID NO:29), for which $<\mu_H>$ at 100° is about 0.28. Representative polypeptides of this subgenus include, but are not limited to:

Ala Val Ser Glu His Gln Leu Leu His Asp Lys Gly Lys Ser Ile
1                   5                        10                      15

Gln Asp Leu Arg Arg Arg Ser Leu Leu Ser Ser Leu Leu Ser Ser
                    20                      25                       30

Leu His Thr Ala NH₂ (SEQ ID NO:21).

In another aspect this invention includes polypeptides of Formula (I) wherein $Xaa^{22-31}$ is (SEQ ID NO:30), for which $<\mu_H>$ at 100° is about 0.29. Representative polypeptides of this subgenus include, but are not limited to:

Ala Val Ser Glu His Gln Leu Leu His Asp Lys Gly Lys Ser Ile
1                   5                        10                      15

Gln Asp Leu Arg Arg Arg Ala Phe Tyr Asp Lys Val Ala Glu Lys
                    20                      25                       30

Leu His Thr Ala NH₂ (SEQ ID NO:22).

Still another aspect of this invention includes polypeptide analogs of the physiologically active truncated homolog bPTH(1–34), as shown in Formula (II):

$Xaa^1$ Val Ser Glu Ile Gln $Xaa^7$ $Xaa^8$ His Asn Leu Gly Lys His Leu $Xaa^{16}$ Ser Xaa18 $Xaa^{19}$ Arg $Xaa^{21}$ $Xaa^{22-31}$ His Asn $Xaa^{34}$ Term, wherein:

$Xaa^1$ is Ser or Ala;
$Xaa^7$ is Leu or Phe;
$Xaa^8$ is Met or Nle;
$Xaa^{16}$ is Asn or Ser;
$Xaa^{18}$ is Leu, Met, or Nle;
$Xaa^{19}$ is Glu or Arg;
$Xaa^{21}$ is Val or Arg;
$Xaa^{22-31}$ is selected from (SEQ ID NO:26, 27, 28, 29, and 30);
$Xaa^{34}$ is Phe or Tyr;
Term is OH or $NR_2$, where each R is H or $(C_1-C_4)$alkyl;
and the pharmaceutically acceptable salts thereof. (Formula II) Representative polypeptides include, but are not limited to:

Ala Val Ser Glu Ile  Gln Phe Nle His Asn Leu Gly Lys His Leu
1                    5                        10                      15

Ser Ser Nle Glu Arg Val Glu Leu Leu Glu Lys Leu Leu Glu Lys
                    20                      25                       30

Leu His Asn Tyr NH₂ (SEQ ID NO:23) and

Ala Val Ser Glu Ile  Gln Phe Nle His Asn Leu Gly Lys His Leu
1                    5                        10                      15

Ser Ser Nle Arg Arg Glu Leu Leu Glu Lys Leu Leu Glu Lys
                    20                      25                       30

Leu His Asn Tyr NH₂ (SEQ ID NO:24).

In still another aspect of this invention, it has surprisingly been found that homologs and analogs of PTH and PTHrP having less than 34 amino acids are also potent bone remodeling agents. These compounds are of general formula: Ala Val Ser Glu $Xaa^5$ Gln Leu Leu His Asp $Xaa^{11}$ Gly $Xaa^{13}$ Ser Ile Gln Asp Leu $Xaa^{19}$ Arg $Xaa^{21}$ $Xaa^{22-31}$ $Xaa^{32}$ $Xaa^{33}$ $Xaa^{34}$ Term Representative polypeptides include, but are not limited to:

Compound 41: AVSEHQLLHD KGKSIQDLRR RELLE-KLLEK LHP-NH₂ (SEQ ID NO:55)

Ala Val Ser Glu His Gln Leu Leu His Asp Lys Gly Lys Ser Ile
1                   5                        10                      15

Gln Asp Leu Arg Arg Arg Glu Leu Leu Glu Lys Leu Leu Glu Lys
                    20                      25                       30

Leu His Pro NH₂ (SEQ ID NO:55).

Physical Data
m.p. 142.8°–166.1° C. $[\alpha]_D^{25}$ –53.80 (c 0.38, H₂O)
FAB $(C_{173}H_{295}N_{55}O_{49})$: [M+H]⁺3929
AAA: Asx 2.0 (2) Glx 5.7 (6) Ser 1.8 (2) His 3.0 (3) Gly 1.1 (1) Ala 0.9 (1) Arg 2.8 (3) Val 1.2 (1) Ile 0.9 (1) Leu 7.4 (8) Lys 4.4 (4) Pro 0.9 (1)

Compound 42: AVSEHQLLHD KGKSIQDLRR RELLE-KLLEK LP-NH$_2$ (SEQ ID NO:56)

Ala Val Ser Glu His Gln Leu Leu His Asp Lys Gly Lys Ser Ile
1             5                    10                   15

Gln Asp Leu Arg Arg Arg Glu Leu Leu Glu Lys Leu Leu Glu Lys
            20                    25                   30

Leu Pro NH$_2$ (SEQ ID NO:56).

Physical Data
m.p. 161.0°–177.0° C. $[\alpha]_D^{25}$–61.97 (c 0.19, H$_2$O)
FAB (C$_{167}$H$_{288}$N$_{52}$O$_{48}$): [M+H]$^+$3792.0
AAA: Asx 2.2 (2) Glx 5.9 (6) Ser 1.9 (2) His 2.1 (2) Gly 1.1 (1) Ala 1.0 (1) Arg 3.0 (3) Val 1.1 (1) Ile 1.0 (1) Leu 7.9 (8) Lys 4.3 (4) Pro 0.9 (1)

The skilled artisan will appreciate that numerous permutations of the polypeptide analogs may be synthesized which will possess the desirable attributes of those described herein provided that an amino acid sequence having a mean hydrophobic moment per residue at 100°±20° greater than about 0.20 is inserted at positions (22–31).

Classical Synthesis of the Polypeptides

The polypeptides of the instant invention may be synthesized by methods such as those set forth in J. M. Stewart and J. D. Young, *Solid Phase Peptide Synthesis*, 2nd ed., Pierce Chemical Co., Rockford, Ill. (1984) and J. Meienhofer, *Hormonal Proteins and Peptides*, Vol. 2, Academic Press, New York, (1973) for solid phase synthesis and E. Schroder and K. Lubke, The Peptides, Vol. 1, Academic Press, New York, (1965) for solution synthesis.

In general, these methods involve the sequential addition of protected amino acids to a growing peptide chain. Normally, either the amino or carboxyl group of the first amino acid and any reactive side chain group are protected. This protected amino acid is then either attached to an inert solid support, or utilized in solution, and the next amino acid in the sequence, also suitably protected, is added under conditions amenable to formation of the amide linkage. After all the desired amino acids have been linked in the proper sequence, protecting groups and any solid support are removed to afford the crude polypeptide. The polypeptide is desalted and purified, preferably chromatographically, to yield the final product.

A preferred method of preparing the analogs of the physiologically active truncated polypeptides, having fewer than about forty amino acids, involves solid phase peptide synthesis. In this method the α-amino (N$^\alpha$) functions and any reactive side chains are protected by acid- or base-sensitive groups. The protecting group should be stable to the conditions of peptide linkage formation, while being readily removable without affecting the extant polypeptide chain. Suitable α-amino protecting groups include, but are not limited to t-butoxycarbonyl (Boc), benzyloxycarbonyl (Cbz), o-chlorobenzyloxycarbonyl, biphenylisopropyloxycarbonyl, t-amyloxycarbonyl (Amoc), isobornyloxycarbonyl, α,α-dimethyl-3,5-dimethoxybenzyloxycarbonyl, o-nitrophenylsulfenyl, 2-cyano-t-butoxycarbonyl, 9-fluorenylmethoxycarbonyl (Fmoc) and the like, preferably t-butoxycarbonyl (Boc). Suitable side chain protecting groups include, but are not limited to: acetyl, benzyl (Bzl), benzyloxymethyl (Bom), o-bromobenzyloxycarbonyl, t-butyl, t-butyldimethylsilyl, 2-chlorobenzyl (Cl-z), 2,6-dichlorobenzyl, cyclohexyl, cyclopentyl, isopropyl, pivalyl, tetrahydropyran-2-yl, tosyl (Tos), trimethylsilyl, and trityl.

In solid phase synthesis, the C-terminal amino acid is first attached to a suitable resin support. Suitable resin supports are those materials which are inert to the reagents and reaction conditions of the stepwise condensation and deprotection reactions, as well as being insoluble in the media used. Examples of commercially available resins include styrene/divinylbenzene resins modified with a reactive group, e.g., chloromethylated co-poly-(styrene-divinylbenzene), hydroxymethylated co-poly-(styrene-divinylbenzene), and the like. Benzylated, hydroxymethylated phenylacetamidomethyl (PAM) resin is preferred. When the C-terminus of the compound is an amide, a preferred resin is p-methylbenzhydrylamino-co-poly (styrene-divinylbenzene) resin.

Attachment to the PAM resin may be accomplished by reaction of the N$^\alpha$-protected amino acid, preferably the Boc-amino acid, as its ammonium, cesium, triethylammonium, 1,5-diazabicyclo-[5.4.0]undec-5-ene, tetramethylammonium, or similar salt in ethanol, acetonitrile, N,N-dimethylformamide (DMF), and the like, preferably the cesium salt in DMF, with the resin at an elevated temperature, for example between about 40° and 60° C., preferably about 50° C., for from about 12 to 72 hours, preferably about 48 hours.

The N$^\alpha$-Boc-amino acid may be attached to the benzhydrylamine resin by means of, for example, an N,N'-diisopropylcarbodiimide (DIC)/1-hydroxybenzotriazole (HOBt) mediated coupling for from about 2 to about 24 hours, preferably about 2 hours at a temperature of between about 10° and 50° C., preferably 25° C. in a solvent such as dichloromethane or dimethylformamide, preferably dichloromethane.

The successive coupling of protected amino acids may be carried out by methods well known in the art, typically in an automated peptide synthesizer. Following neutralization with triethylamine or similar base, each protected amino acid is preferably introduced in approximately 1.5 to 2.5 fold molar excess and the coupling carried out in an inert, nonaqueous, polar solvent such as dichloromethane, DMF, or mixtures thereof, preferably in dichloromethane at ambient temperature. Representative coupling agents are N,N'-dicyclohexylcarbodiimide (DCC), N,N'-diisopropylcarbodiimide (DIC) or other carbodiimide, either alone or in the presence of 1-hydroxybenzotriazole (HOBt), O-acyl ureas, benzotriazol-1-yl-oxytris(pyrrolidino) phosphonium hexafluorophosphate (PyBop), N-hydroxysuccinimide, other N-hydroxyimides, or oximes. Alternatively, protected amino acid active esters (e.g. p-nitrophenyl, pentafluorophenyl and the like) or symmetrical anhydrides may be used.

At the end of the solid phase synthesis the fully protected peptide is removed from the resin. When the linkage to the resin support is of the benzyl ester type, cleavage may be effected by means of aminolysis with an alkylamine or fluoroalkylamine for peptides with an alkylamide C-terminus, or by aminolysis with, for example, ammonia/methanol or ammonia/ethanol for peptides with an unsubstituted amide C-terminus, at a temperature between about –10° and 50° C., preferably about 25° C, for between about 12 and 24 hours, preferably about 18 hours. Peptides with a hydroxy C-terminus may be cleaved by HF or other strongly acidic deprotection regimen or by saponification. Alternatively, the peptide may be removed from the resin by transesterification, e.g., with methanol, followed by aminolysis or saponification. The protected peptide may be purified by silica gel chromatography.

The side chain protecting groups may be removed from the peptide by treating the aminolysis product with, for example, anhydrous liquid hydrogen fluoride in the presence of anisole or other carbonium ion scavenger, treatment with hydrogen fluoride/pyridine complex, treatment with tris(trifluoroacetyl)boron and trifluoroacetic acid, by reduction with hydrogen and palladium on carbon or polyvinylpyrrolidone, or by reduction with sodium in liquid ammonia, preferably with liquid hydrogen fluoride and anisole at a temperature between about −10° and +10° C., preferably at about 0° C., for between about 15 minutes and 2 hours, preferably about 1.5 hours. For peptides on the benzhydrylamine resin, the resin cleavage and deprotection steps may be combined in a single step utilizing liquid hydrogen fluoride and anisole as described above.

The solution may be desalted (e.g. with BioRad AG-3® anion exchange resin) and the peptide purified by a sequence of chromatographic steps employing any or all of the following types: ion exchange on a weakly basic resin in the acetate form; hydrophobic adsorption chromatography on underivatized co-poly(styrene-divinylbenzene), e.g. Amberlite® XAD; silica gel adsorption chromatography; ion exchange chromatography on carboxymethylcellulose; partition chromatography, e.g. on Sephadex® G-25; countercurrent distribution; or high performance liquid chromatography (HPLC), especially reversed-phase HPLC on octyl- or octadecylsilylsilica (ODS) bonded phase column packing.

Thus, another aspect of the present invention relates to processes for preparing polypeptides and pharmaceutically acceptable salts thereof which processes comprise sequentially condensing protected amino acids on a suitable resin support, removing the protecting groups and resin support, and purifying the product, to afford analogs of the physiologically active truncated homologs and analogs of PTH and PTHrp, preferably of PTH(1–34) and PTHrp(1–34), in which the amino acids at positions (22–31) form an amphipathic α-helical peptide sequence, as defined above.

Recombinant Synthesis of the Polypeptides

Alternatively, the polypeptides of this invention may be prepared by cloning and expression of a gene encoding for the desired polypeptide. In this process, a plasmid containing the desired DNA sequence is prepared and inserted into an appropriate host microorganism, typically a bacteria, such as *E. coli*, or a yeast, such as *Saccharomyces cerevisiae*, inducing the host microorganism to produce multiple copies of the plasmid, and so of the cDNA encoding for the polypeptide analogs of this invention.

First, a synthetic gene coding for the selected PTH or PTHrp analog is designed with convenient restriction enzyme cleavage sites to facilitate subsequent alterations. Polymerase chain reaction (PCR), as taught by Mullis in U.S. Pat. Nos. 4,683,195 and 4,683,202, may be used to amplify the sequence.

The amplified synthetic gene may be isolated and ligated to a suitable plasmid, such as a Trp LE plasmid, into which four copies of the gene may be inserted in tandem. Preparation of Trp LE plasmids is described in U.S. Pat. No. 4,738,921 and European Patent Publication No. 0212532. Trp LE plasmids generally produce 8–10 times more protein than Trp E plasmids. The multi-copy gene may then be expressed in an appropriate host, such as *E. coli* or *S. cerevisiae*.

The specific expression vector used herein was Trp LE 18 Prot (Ile$^3$, Pro$^5$) containing the following elements: a pBR322 fragment (EcoRI-BamHI) containing the ampicillin resistant gene and the plasmid origin of replication; an EcoRI-SacII fragment containing the trp promoter and the trpE gene; an HIV protease (Ile$^3$,Pro$^5$) gene fragment (SacII-HindIII); a bGRF gene fragment (HindIII-BamHI); and a transcription terminator from *E. coli* rpoc gene. The HIV protease and bGRF gene fragments are not critical and may be replaced with other coding sequences, if desired.

The expressed multimeric fusion proteins accumulate intracellularly into stable inclusion bodies and may be separated by centrifugation from the rest of the cellular protein. The isolated fusion protein is converted to the monomeric PTH or PTHrp analog and may be purified by cation exchange and/or reverse phase HPLC.

Alternative methods of cloning, amplification, expression, and purification will be apparent to the skilled artisan. Representative methods are disclosed in Maniatis, et al., *Molecular Cloning*, a Laboratory Manual, 2nd Ed., Cold Spring Harbor Laboratory (1989).

Utility and Administration

The polypeptides of this invention are useful for the prevention and treatment of a variety of mammalian conditions manifested by loss of bone mass. In particular, the compounds of this invention are indicated for the prophylaxis and therapeutic treatment of osteoporosis and osteopenia in humans.

In general, the polypeptides of this invention, or salts thereof, are administered in amounts between about 0.002 and 10 μg/kg body weight per day, preferably from about 0.04 to about 0.2 μg/kg body weight per day. For a 50 kg human female subject, the daily dose of active ingredient is from about 0.1 to about 500 μgs, preferably from about 2.0 to about 100 μgs. In other mammals, such as horses, dogs, and cattle, higher doses may be required. This dosage may be delivered in a conventional pharmaceutical composition by a single administration, by multiple applications, or via controlled release, as needed to achieve the most effective results, preferably one or more times daily by injection.

The selection of the exact dose and composition and the most appropriate delivery regimen will be influenced by, inter alia, the pharmacological properties of the selected polypeptide, the nature and severity of the condition being treated, and the physical condition and mental acuity of the recipient.

In the treatment of corticosteroid induced osteopenia, it is expected that the requisite dose of polypeptide will be greater for higher doses of corticosteroids.

Representative delivery regimens include oral, parenteral (including subcutaneous, intramuscular and intravenous), rectal, buccal (including sublingual), pulmonary, transdermal, and intranasal.

Pharmaceutically acceptable salts retain the desired biological activity of the parent polypeptide without toxic side effects. Examples of such salts are (a) acid addition salts formed with inorganic acids, for example hydrochloric acid, hydrobromic acid, sulfuric acid, phosphoric acid, nitric acid and the like; and salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, pamoic acid, alginic acid, polyglutamic acid, naphthalenesulfonic acids, naphthalene disulfonic acids, polygalacturonic acid and the like; (b) base addition salts formed with polyvalent metal cations such as zinc, calcium, bismuth, barium, magnesium, aluminum, copper, cobalt, nickel, cadmium, and the like; or with an organic cation formed from N,N'-dibenzylethylenediamine or ethylenediamine; or (c) combinations of (a) and (b), e.g., a zinc tannate salt and the like.

A further aspect of the present invention relates to pharmaceutical compositions comprising as an active ingredient a polypeptide of the present invention, or pharmaceutically acceptable salt thereof, in admixture with a pharmaceutically acceptable, non-toxic carrier. As mentioned above, such compositions may be prepared for parenteral (subcutaneous, intramuscular or intravenous)

administration, particularly in the form of liquid solutions or suspensions; for oral or buccal administration, particularly in the form of tablets or capsules; for pulmonary or intranasal administration, particularly in the form of powders, nasal drops or aerosols; and for rectal or transdermal administration.

The compositions may conveniently be administered in unit dosage form and may be prepared by any of the methods well-known in the pharmaceutical art, for example as described in *Remington's Pharmaceutical Sciences*, 17th ed., Mack Publishing Company, Easton, Pa., (1985). Formulations for parenteral administration may contain as excipients sterile water or saline, alkylene glycols such as propylene glycol, polyalkylene glycols such as polyethylene glycol, oils of vegetable origin, hydrogenated naphthalenes and the like. For oral administration, the formulation can be enhanced by the addition of bile salts or acylcarnitines. Formulations for nasal administration may be solid and may contain excipients, for example, lactose or dextran, or may be aqueous or oily solutions for use in the form of nasal drops or metered spray. For buccal administration typical excipients include sugars, calcium stearate, magnesium stearate, pregelatinated starch, and the like.

When formulated for nasal administration, the absorption across the nasal mucous membrane may be enhanced by surfactant acids, such as for example, glycocholic acid, cholic acid, taurocholic acid, ethocholic acid, deoxycholic acid, chenodeoxycholic acid, dehydrocholic acid, glycodeoxycholic acid, cyclodextrins and the like in an amount in the range between about 0.2 and 15 weight percent, preferably between about 0.5 and 4 weight percent, most preferably about 2 weight percent.

Delivery of the compounds of the present invention to the subject over prolonged periods of time, for example, for periods of one week to one year, may be accomplished by a single administration of a controlled release system containing sufficient active ingredient for the desired release period. Various controlled release systems, such as monolithic or reservoir-type microcapsules, depot implants, osmotic pumps, vesicles, micelles, liposomes, transdermal patches, iontophoretic devices and alternative injectable dosage forms may be utilized for this purpose. Localization at the site to which delivery of the active ingredient is desired is an additional feature of some controlled release devices, which may prove beneficial in the treatment of certain disorders.

One form of controlled release formulation contains the polypeptide or its salt dispersed or encapsulated in a slowly degrading, non-toxic, non-antigenic polymer such as copoly (lactic/glycolic) acid, as described in the pioneering work of Kent, Lewis, Sanders, and Tice, U.S. Pat. No. 4,675,189. The compounds or, preferably, their relatively insoluble salts, may also be formulated in cholesterol or other lipid matrix pellets, or silastomer matrix implants. Additional slow release, depot implant or injectable formulations will be apparent to the skilled artisan. See, for example, *Sustained and Controlled Release Drug Delivery Systems*, J. R. Robinson ed., Marcel Dekker, Inc., New York, 1978, and R. W. Baker, *Controlled Release of Biologically Active Agents*, John Wiley & Sons, New York, 1987.

The following specific Examples are intended to illustrate the synthesis and testing of representative compounds of the invention and should not be construed as limiting the scope of the claims. In the Examples, "m.p." is melting point, "$[\alpha]_D^{25}$" is the optical activity at 25° C. at the given concentration in the indicated solvent, "FAB" is fast atom bombardment mass spectrometry, and "AAA" is amino acid analysis, with expected values in parentheses following the observed values. The amino acid analyses were conducted on a Hewlett-Packard AminoQuant Analyzer following the manufacturer's recommended protocols. Primary amino acids were derivatized with o-phthalaldehyde; secondary amino acids with Fmoc. Fluorescent detection of the derivatized amino acids was used for quantification. The protected amino acids were obtained from Applied Biosystems Inc. (Foster City, Calif.).

EXAMPLE I

Compound 1 (SEQ ID NO:7) was prepared on 0.5 mmol scale by the solid phase method on 4-methylbenzhydrylamine resin, using an automated Applied Biosystems Model 430A peptide synthesizer. The α-amino groups were protected with t-butoxycarbonyl (Boc). The side chain protecting groups were: benzyl (Bzl) for Asp, Glu, and Ser; tosyl (Tos) for Arg; benzyloxymethyl (Bom) for His; and 2-chlorobenzyl (Cl-z) for Lys. The amino acids were coupled sequentially using N,N-dicyclohexylcarbodiimide/1-hydroxybenzotriazole (DCC/HOBt) following Stewart and Young (supra). After each amino acid coupling, the peptide was acetylated using a mixture of acetic anhydride and diisopropylethylamine in N-methylpyrrolidone. The completed peptide was cleaved from the resin with simultaneous deprotection of the side chain protecting groups using anhydrous HF (25 mL) in the presence of anisole (2.5 mL) at −10° C. for 30 minutes and at 0° C. for 60 minutes. After evaporation of the HF in vacuo, the residue was washed with anhydrous ether, and the crude peptide extracted with 10% acetic acid. Lyophilization of the 10% acetic acid extract gave 900 mgs of crude product. The peptide was purified by medium pressure ODS reversed phase column chromatography using a gradient of 22–45% $CH_3CN$ in 0.1%. TFA. The product eluted in three fractions, which were concentrated and lyophilized to give 130 mgs of white solid of >98% purity.

Compound 1

AVSEHOLLHDKGKSIODLRRRELLEKLLEKLHTA-NH$_2$ (SEO ID NO:7)

Ala Val Ser Glu His Gln Leu Leu His Asp Lys Gly Lys Ser Ile
1              5                    10                15
Gln Asp Leu Arg Arg Arg Glu Leu Leu Glu Lys Leu Leu Glu Lys
              20                    25                30
Leu His Thr Ala NH$_2$  (SEQ ID NO:7)

Physical Data: m.p. 150°–159° C. $[\alpha]_D^{25}$ −34.880 (c 0.16, $H_2O$)

FAB ($C_{175}H_{300}N_{56}O_{51}$) [M+H]$^+$4005.5

AAA: Asp, 1.9(2); Glu, 5.6(6); Ser, 1.6(2); His, 2.7(3); Gly, 1.0(1); Thr, 0.9(1); Ala, 1.9(2); Arg, 2.8(3); Val, 1.0(1); Ile, 0.9(1); Leu, 7.3(8); Lys, 4.0(4).

Similarly, Compounds 2, 5–18, 21–27, 29–36, 38–48, 50–54, 58–64 and 66–70 were prepared and characterized, substituting PAM resin as needed for the synthesis of hydroxy-terminal polypeptides.

Compound 2

AVSEHOLLHDKGKSIODLRRRELLEKLLEKLHTA-OH (SEQ ID NO:6)

Ala Val Ser Glu His Gln Leu Leu His Asp Lys Gly Lys Ser Ile
1           5                    10                   15
Gln Asp Leu Arg Arg Arg Glu Leu Leu Glu Lys Leu Leu Glu Lys
              20                    25                   30
Leu His Thr Ala OH (SEQ ID NO:6)

Physical Data: m.p. 154°–170° C. $[\alpha]_D^{25}$ –49.350 (c 0.46, H$_2$O)

FAB (C$_{175}$H$_{301}$N$_{57}$O$_{50}$): [M+H]$^+$4005.0

AAA: Asp, 2.1(2); Glu, 5.9(6); Ser, 1.7(2); His, 2.9(3); Gly 1.1(1); Thr, 1.0(1); Ala, 1.9(2); Arg, 3.0(3); Val, 1.2(1); Ile, 1.0(1); Leu, 7.8(8); Lys, 4.2(4).

Compound 5

AVSEHOLLHDKGKSIODLRRRELLERLLERLHTA-OH (SEQ ID NO:15)

Ala Val Ser Glu His Gln Leu Leu His Asp Lys Gly Lys Ser Ile
1           5                    10                   15
Gln Asp Leu Arg Arg Arg Glu Leu Leu Glu Arg Leu Leu Glu Arg
              20                    25                   30
Leu His Thr Ala OH (SEQ ID NO:15)

Physical Data: m.p. 147°–165° C. $[\alpha]_D^{25}$ –49.170 (c 0.66, H$_2$O)

FAB (C$_{175}$H$_{299}$N59O$_{52}$) : [M+H]$^+$4061

AAA: Asp, 2.1(2); Gly, 6.1(6); Ser, 1.8(2); His, 3.1(3); Gly, 1.1(1); Thr, 1.0(1); Ala, 2.0(2); Arg, 5.0(5); Val, 1.0(1); Ile, 0.9(1); Leu, 7.7(8); Lys, 1.9(2).

Compound 6

AVSEHOLLHDRGRSIODLRRRELLERLLERLHTA-OH (SEQ ID NO:16)

Ala Val Ser Glu His Gln Leu Leu His Asp Arg Gly Arg Ser Ile
1           5                    10                   15
Gln Asp Leu Arg Arg Arg Glu Leu Leu Glu Arg Leu Leu Glu Arg
              20                    25                   30
Leu His Thr Ala OH (SEQ ID NO:16)

Physical Data: m.p. 150°–170° C. $[\alpha]_D^{25}$ –48.65° (c 0.54, H$_2$O)

FAB (C$_{175}$H$_{299}$N$_{63}$O$_{52}$): [M+H]$^+$4118.0

AAA: Asp, 2.1(2); Glu, 6.1(6); Ser, 1.8(2); His, 3.2(3); Gly, 1.2(1); Thr, 1.0(1); Ala, 2.0(2); Arg, 6.9(7); Val, 1.0(1); Ile, 1.0(1); Leu, 7.8(8).

Compound 7

AVSEHOLLHDRGRSIODLRRRELLERLLKRLHTA-OH (SEQ ID NO:17)

Ala Val Ser Glu His Gln Leu Leu His Asp Arg Gly Arg Ser Ile
1           5                    10                   15
Gln Asp Leu Arg Arg Arg Glu Leu Leu Glu Arg Leu Leu Lys Arg
              20                    25                   30
Leu His Thr Ala OH (SEQ ID NO:17)

Physical Data: m.p. 177°–182° C. $[\alpha]_D^{25}$ –46.170 (c 0.14, H$_2$O)

FAB (C$_{176}$H$_{304}$N$_{64}$O$_{50}$): [M+H]$^+$4117

AAA: Asp, 2.0(2); Glu, 4.8(5); Ser, 1.8(2); His, 3.2(3); Gly, 1.1(1); Thr, 0.9(1); Ala, 1.9(2); Arg, 6.7(7); Val, 1.0(1); Ile, 1.0(1); Lys, 7.7(8); Lys, 0.9(1).

Compound 8

AVSEHOLLHDKGKSIODLRRRELLEKLLRKLHTA-OH (SEQ ID NO:5)

Ala Val Ser Glu His Gln Leu Leu His Asp Lys Gly Lys Ser Ile
1           5                    10                   15
Gln Asp Leu Arg Arg Arg Glu Leu Leu Glu Lys Leu Leu Arg Lys
              20                    25                   30
Leu His Thr Ala OH (SEQ ID NO:5)

Physical Data: m.p. 147°–165° C. $[\alpha]_D^{25}$ –49.170 (c 0.66, H$_2$O)

FAB (C$_{176}$H$_{305}$N$_{59}$O$_{49}$) : [M+H]$^+$4033.0

AAA: Asp, 2.0(2); Glu, 4.8(5); Ser, 1.8(2); His, 2.7(3); Gly, 1.1(1); Thr, 0.9(1); Ala, 2.0(2); Arg, 3.9(4); Val, 1.0(1); Ile, 1.0(1); Leu, 7.9(8); Lys, 4.0(4).

Compound 9

AVSEHOLLHDKGKSIODLRRRELLEKLLEKLHTA-GRR-OH (SEQ ID NO:10)

Ala Val Ser Glu His Gln Leu Leu His Asp Lys Gly Lys Ser Ile
1           5                    10                   15
Gln Asp Leu Arg Arg Arg Glu Leu Leu Glu Lys Leu Leu Glu Lys
              20                    25                   30
Leu His Thr Ala Gly Arg Arg OH (SEQ ID NO:10)
              35

Physical Data: m.p. 158°–160° C. $[\alpha]_D^{25}$ –44.76° (c 0.1, H$_2$O)

FAB (C$_{189}$H$_{326}$N$_{64}$O$_{55}$): [M]$^+$4375.0

AAA: Asp, 2.0(2); Glu, 5.9(6); Ser, 1.7(2); His, 2.9(3); Gly, 2.3(2); Thr, 1.0(1); Ala, 1.9(2); Arg, 5.0(5); Val, 1.2(1); Ile, 1.0(1); Leu, 7.8(8); Lys, 4.3(4).

Compound 10

AVSEAOLLHDLGKSIODLRRRELLEKLLEKLHAL-OH (SEQ ID NO:14)

Ala Val Ser Glu Ala Gln Leu Leu His Asp Leu Gly Lys Ser Ile
1           5                    10                   15
Gln Asp Leu Arg Arg Arg Glu Leu Leu Glu Lys Leu Leu Glu Lys
              20                    25                   30
Leu His Ala Leu OH (SEQ ID NO:14)

Physical Data: m.p. 170°–175° C. $[\alpha]_D^{25}$ –31.590 (c 0.54, H$_2$O)

FAB (C₁₇₄H₃₀₀N₅₂O₅₁) : [M+H]⁺3936.0

AAA: Asp, 2.0(2); Glu, 6.0(6); Ser, 1.8(2); His, 2.0(2); Gly, 1.2(1); Ala, 3.0(3); Arg, 2.8(3); Val, 1.1(1); Ile, 1.0(1); Leu, 9.9(10); Lys, 3.0(3).

Compound 11

AVSEHOLLHDKGKSIODLRRRELLEKLLELLKEL-NH₂ (SEO ID NO:11)

Ala Val Ser Glu His Gln Leu Leu His Asp Lys Gly Lys Ser Ile
1           5                    10              15
Gln Asp Leu Arg Arg Arg Glu Leu Leu Glu Lys Leu Leu Glu Lys
         20                   25                  30
Leu Lys Glu Leu NH₂ (SEQ ID NO:11)

Physical Data: m.p. 172°–174° C. [α]$_D^{25}$-43.29° (c 0.2, H₂O)

FAB (C₁₇₉H₃₁₁N₅₅O₅₂): [M+H]⁺4065.8

AAA: Asp, 2.2(2); Glu, 7.7(7); Ser, 1.7(2); His, 2.0(2); Gly, 1.0(1); Ala, 1.0(1); Arg, 3.0(3); Val, 1.1(1); Ile, 1.0(1); Leu, 9.3(9); Lys, 5.1(5).

Compound 12

AVSEIOFXHNLGKHLSSXERVELLEKLLEKLHNY-NH₂ (X=Nle, SEO ID NO:23)

Ala Val Ser Glu Ile Gln Phe Nle His Asn Leu Gly Lys His Leu
1           5                    10              15
Ser Ser Nle Glu Arg Val Glu Leu Leu Glu Lys Leu Leu Glu Lys
         20                   25                  30
Leu His Asn Tyr NH₂ (SEQ ID NO:23)

Physical Data: m.p. 178° C. [α]$_D^{25}$-36.880 (C 0.4, H₂O)

FAB (C₁₈₂H₂₉₅N₅₀O₅₁): [M+H]⁺4001.6

AAA: Asp, 2.1(2); Glu, 6.5(6); Ser, 2.7(3); His, 3.1(3); Gly, 1.1(1); Ala, 1.0(1); Arg, 1.0(1); Tyr, 0.8(1); Val, 2.0(2); Phe, 1.0(1); Ile, 0.9(1); Leu+Nle, 8.5(7+2); Lys, 3.1(3).

Compound 13

AVSEIOFXHNLGKHLSSXRRRELLEKLLEKLHNY-NH₂ (X=Nle. SEO ID NO:24)

Ala Val Ser Glu Ile Gln Phe Nle His Asn Leu Gly Lys His Leu
1           5                    10              15
Ser Ser Nle Arg Arg Arg Glu Leu Leu Glu Lys Leu Leu Glu Lys
         20                   25                  30
Leu His Asn Tyr NH₂ (SEQ ID NO:24)

Physical Data: m.p. 260° C. [α]$_D^{25}$-37.020 (c 0.2, H₂O)

FAB (C₁₈₄H₃₀₄N₅₆O₄₉): [M+H]⁺4084

AAA: Asp, 2.1(2); Glu, 5.5(5); Ser, 2.6(3); His, 3.1(3); Ala, 1.0(1); Gly, 1.1(1); Arg, 3.2(3); Tyr, 1.0(1); Val, 1.0(1); Phe, 1.0(1); Ile, 1.0(1); Leu, 9.0(9); Lys, 3.0(3).

Compound 14

AVSEHOLLHDKGKSIODLRRRALAEALAEALHTA-NH₂ (SEO ID NO:20)

Ala Val Ser Glu His Gln Leu Leu His Asp Lys Gly Lys Ser Ile
1           5                    10              15
Gln Asp Leu Arg Arg Arg Ala Leu Ala Glu Ala Leu Ala Glu Ala
         20                   25                  30
Leu His Thr Ala NH₂ (SEQ ID NO:20)

Physical Data: m.p. 190°–225° C. [α]$_D^{25}$-56.580 (c 0.36, H₂O)

FAB (C₁₆₁H₂₇₂N₅₄O₄₉): [M+H]⁺3747.0

AAA: Asp, 2.1(2); Glu, 4.9(5); Ser, 1.7(2); His, 2.6(3); Gly, 1.1(1); Thr, 1.0(1); Ala, 7.6(7); Arg, 2.8(3); Val, 1.2(1); Ile, 1.0(1); Leu, 6.6(6); Lys, 1.9(2).

Compound 15

AVSEHOLLHDKGKSIODLARRELLEKLLEKLHTA-NH₂ (SEO ID NO:12)

Ala Val Ser Glu His Gln Leu Leu His Asp Lys Gly Lys Ser Ile
1           5                    10              15
Gln Asp Leu Ala Arg Arg Glu Leu Leu Glu Lys Leu Leu Glu Lys
         20                   25                  30
Leu His Thr Ala NH₂ (SEQ ID NO:12)

Physical Data: m.p. 170°–180° C. [α]$_D^{25}$-48.190 (c 0.2, H₂O)

FAB (C₁₇₂H₂₉₃N₅₃O₅₁): [M+H]⁺3919.0

AAA: Asp, 2.1(2); Glu, 6.1(6); Ser, 1.7(2); His, 3.1(3); Gly, 1.1(1); Thr, 1.0(1); Ala, 3.0(3); Arg, 2.1(2); Val, 1.1(1); Ile, 1.0(1); Leu, 8.0(8); Lys, 4.4(4).

Compound 16

AVSEHQLLHDKGKSIODLRRAELLEKLLEKLHTA-NH₂ (SEO ID NO:13)

Ala Val Ser Glu His Gln Leu Leu His Asp Lys Gly Lys Ser Ile
1           5                    10              15
Gln Asp Leu Arg Arg Ala Glu Leu Leu Glu Lys Leu Leu Glu Lys
         20                   25                  30
Leu His Thr Ala NH₂ (SEQ ID NO:13)

Physical Data: m.p. 190°–195° C. [α]$_D^{25}$-50.50° (c 0.4, H₂O)

FAB (C₁₇₂H₂₉₃N₅₃O₅₁): [M+H]⁺3919.0

AAA: Asp, 2.1(2); Glu, 6.0(6); Ser, 1.8(2); His, 3.1(3); Gly, 1.1(1); Thr, 1.0(1); Ala, 3.0(3); Arg, 2.1(2); Val, 1.1(1); Ile, 1.0(1); Leu, 7.5(8); Lys, 4.2(4).

Compound 17

AVSEHOLLHDKGKSIODLRRRSLLSSLLSSLHTA-NH₂ (SEQ ID NO:21)

Ala Val Ser Glu His Gln Leu Leu His Asp Lys Gly Lys Ser Ile
1           5                    10              15

-continued

Gln Asp Leu Arg Arg Arg Ser Leu Leu Ser Ser Leu Leu Ser Ser
                    20                  25                  30

Leu His Thr Ala NH$_2$ (SEQ ID NO:21)

Physical Data: m.p. 195°–204° C. $[\alpha]_D^{25}$ –67.11° (c 0.3, H$_2$O)

FAB (C$_{163}$H$_{280}$N$_{54}$O$_{50}$) : [M+H]$^+$3796.0

AAA: Asp, 2.1(2); Glu, 2.9(3); Ser, 6.8(7); His, 3.1(3); Gly, 1.2(1); Thr, 1.0(1); Ala, 2.0(2); Arg, 3.0(3); Val, 1.0(1); Ile, 1.0(1); Leu, 8.2(8); Lys, 2.0(2).

Compound 18

AVSEHOLLHDKGKSIODLRRRAFYDKVAEKLHTA-NH$_2$ (SEO ID NO:22)

Ala Val Ser Glu His Gln Leu Leu His Asp Lys Gly Lys Ser Ile
 1               5                  10                  15

Gln Asp Leu Arg Arg Arg Ala Phe Tyr Asp Lys Val Ala Glu Lys
                    20                  25                  30

Leu His Thr Ala NH$_2$ (SEQ ID NO:22)

Physical Data: m.p. 200°–207° C. $[\alpha]_D^{25}$ –60.260 (c 0.6, H$_2$O)

FAB (C$_{174}$H$_{284}$N$_{56}$O$_{50}$): [M+H]$^+$3960.0

AAA: Asp, 2.9(3); Glu, 3.5(4); Ser, 1.4(2); His, 2.6(3); Gly, 0.9(1); Thr, 1.0(1); Ala, 4.0(4); Arg, 3.0(3); Tyr, 0.9(1); Val, 1.9(2); Phe, 1.1(1); Ile, 0.9(1); Leu, 3.6(4); Lys, 4.1(4).

Compound 21

AVSEIOFLHN LGKHLSSLRR RELLEKLLEK LHNY-NH$_2$ (SEO ID NO:35)

Ala Val Ser Glu Ile Gln Phe Leu His Asn Leu Gly Lys His Leu
 1               5                  10                  15

Ser Ser Leu Arg Arg Arg Glu Leu Leu Glu Lys Leu Leu Glu Lys
                    20                  25                  30

Leu His Asn Tyr NH$_2$ (SEQ ID NO:35)

Physical Data: m.p. 148°–155° C. $[\alpha]_D^{25}$ –45.97 (c 0.26, H$_2$O)

FAB(C$_{184}$H$_{304}$N$_{56}$O$_{49}$) : [M+H]$^+$4084

AAA: Asx, 2.1(2); Glx, 5.0(5); Ser, 2.7(3); His, 3.0(3); Gly, 1.0(1); Ala, 0.9(1); Arg, 3.1(3); Tyr, 0.9(1); Val, 1.0(1); Phe, 0.9(1); Ile, 0.9(1); Leu 9.3(9); Lys, 3.2(3).

Compound 24

AVSEHOLLHD KGKSIODLKL KELLEKLLEK LHTA-NH$_2$ (SEO ID NO:38)

Ala Val Ser Glu His Gln Leu Leu His Asp Lys Gly Lys Ser Ile
 1               5                  10                  15

Gln Asp Leu Lys Leu Lys Glu Leu Leu Glu Lys Leu Leu Glu Lys
                    20                  25                  30

Leu His Thr Ala NH$_2$ (SEQ ID NO:38)

Physical Data: m.p. 175°–182° C. $[\alpha]_D^{25}$ –49.99(c 0.47, H$_2$O)

FAB (C$_{175}$H$_{299}$N$_{49}$O$_{51}$): [M+H]$^+$3906.5

AAA: Asx, 2.1(2); Glx, 6.5(6); Ser, 1.8(2); His, 3.1(3); Gly, 1.1(1); Thr, 1.0(1); Ala, 2.1(2); Val, 1.1(1); Ile, 1.0(1); Leu, 9.1(9); Lys, 6.5(6).

Compound 25

AVSEHOLLHD KGKSIODLRR RELLERLLER LHTA-NH$_2$ (SEO ID NO:39)

Ala Val Ser Glu His Gln Leu Leu His Asp Lys Gly Lys Ser Ile
 1               5                  10                  15

Gln Asp Leu Arg Arg Arg Glu Leu Leu Glu Arg Leu Leu Glu Arg
                    20                  25                  30

Leu His Thr Ala- NH$_2$ (SEQ ID NO:39)

Physical Data: m.p. 136.5°–153.5° C. $[\alpha]_D^{25}$ –32.57(c 0.13, H$_2$O)

FAB (C$_{175}$H$_{300}$N$_{60}$O$_{51}$) : [M+H]$^{30}$ 4060.8

AAA: Asx, 2.2(2); Glx, 6.2(6); Ser, 1.8(2); His, 3.2(3); Gly, 1.1(1); Thr, 1.0(1); Ala, 2.1(2); Arg, 5.2(5); Val, 1.1(1); Ile, 1.1(1); Leu, 8.4(8); Lys, 2.2(2).

Compound 26

AVSEHOLLHD KGKSIODLRR RELLERLLER LHTAP-OH (SEO ID NO:40)

Ala Val Ser Glu His Gln Leu Leu His Asp Lys Gly Lys Ser Ile
 1               5                  10                  15

Gln Asp Leu Arg Arg Arg Glu Leu Leu Glu Arg Leu Leu Glu Arg
                    20                  25                  30

Leu His Thr Ala Pro OH (SEQ ID NO:40)

Physical Data: m.p. 125.8°–127.2° C. $[\alpha]_D^{25}$ –54.62(c 0.23, H$_2$O)

FAB (C$_{180}$H$_{306}$N$_{60}$O$_{53}$) : [M+H]$^+$4158.0

AAA: Asx, 2.1(2); Glx, 6.2(6); Ser, 1.8(2); His, 2.9(3); Gly, 1.1(1); Thr, 1.0(1); Ala, 2.0(2); Arg, 5.1(5); Val, 1.0(1); Ile, 1.0(1); Leu, 8.0(8); Lys, 2.1(2); Pro, 1.1(1).

Compound 27

AVSEHOLLHD KGKSIODLRR RELLERLLER LHTAGRR-OH (SEO ID NO:41)

Ala Val Ser Glu His Gln Leu Leu His Asp Lys Gly Lys Ser Ile
 1               5                  10                  15

Gln Asp Leu Arg Arg Arg Glu Leu Leu Glu Arg Leu Leu Glu Arg
                    20                  25                  30

Leu His Thr Ala Gly Arg Arg OH (SEQ ID NO:41)
                35

Physical Data: m.p. 106°–137.3° C. $[\alpha]_D^{25}$ –39.55(c 0.67, H$_2$O)

FAB (C$_{189}$H$_{326}$N$_{60}$O$_{53}$): [M+H]$^+$4430.5

AAA: Asx, 2.1(2); Glx, 5.9(6); Ser, 1.6(2); His, 2.7(3); Gly, 2.2(2); Thr, 1.0(1); Ala, 1.8(2); Arg, 7.3(7); Val, 0.8(1); Ile, 1.0(1); Leu, 8.1(8); Lys, 2.1(2).

Compound 29

AVSEHOLLHD KGKSIODLRR RELLEKLLEK LHTY-NH$_2$ (SEQ ID NO:43)

Ala Val Ser Glu His Gln Leu Leu His Asp Lys Gly Lys Ser Ile
1               5                   10                  15

Gln Asp Leu Arg Arg Arg Glu Leu Leu Glu Lys Leu Leu Glu Lys
                20                  25                  30

Leu His Thr Tyr NH$_2$ (SEQ ID NO:43)

Physical Data: m.p. 160°–172° C. $[\alpha]_D^{25}$ –49.85(c 0.34, H$_2$O)

FAB(C$_{181}$H$_{304}$N$_{56}$O$_{52}$): [M+H]$^+$4096.9

AAA: Asx, 2.0(2); Glx, 5.6(6); Ser, 1.7(2); His, 3.1(3); Gly, 1.1(1); Thr, 0.9(1); Ala, 0.9(1); Arg, 3.0(3); Tyr, 0.9(1); Val, 1.0(1); Ile, 1.0(1); Leu, 7.7(8); Lys, 4.4(4).

Compound 30

AVSEHOLLHD KGYSIODLRR RELLEKLLEK LHTA-NH$_2$ (SEQ ID NO:44)

Ala Val Ser Glu His Gln Leu Leu His Asp Lys Gly Tyr Ser Ile
1               5                   10                  15

Gln Asp Leu Arg Arg Arg Glu Leu Leu Glu Lys Leu Leu Glu Lys
                20                  25                  30

Leu His Thr Ala NH$_2$ (SEQ ID NO:44)

Physical Data: m.p. 130°–171° C. $[\alpha]D_{25}$ –40.65 (c 0.34 H$_2$O)

FAB(C$_{178}$H$_{297}$N$_{55}$O$_{52}$): [M+H]$^+$4039.4

AAA: Asx, 2.0(2); Glx, 5.5(6); Ser, 1.8(2); His, 3.4(3); Gly, 1.1(1); Thr, 1.0(1); Ala, 2.0(2); Arg, 2.9(3); Tyr, 0.8(1); Val, 1.0(1); Ile, 0.9(1); Leu, 7.9(8); Lys, 3.4(3).

Compound 31

AVSEHOLLHD KGCSIODLRR RELLEKLLEK LHTA-NH$_2$ (SEQ ID NO:45)

Ala Val Ser Glu His Gln Leu Leu His Asp Lys Gly Cys Ser Ile
1               5                   10                  15

Gln Asp Leu Arg Arg Arg Glu Leu Leu Glu Lys Leu Leu Glu Lys
                20                  25                  30

Leu His Thr Ala NH$_2$ (SEQ ID NO:45)

Physical Data: m.p. 140°–160° C. $[\alpha]_D^{25}$ –44.48 (c 0.25, H$_2$O)

FAB (C$_{172}$H$_{293}$N$_{55}$O$_{51}$S$_1$): [M+H]$^+$3979

AAA: Asx+Cys, 3.0(2+1); Glx, 5.6(6); Ser, 1.7(2); His, 3.0(3); Gly, 1.0(1); Thr, 0.9(1); Ala, 1.9(2); Arg, 2.5(3); Val, 1.0(1); Ile, 0.9(1); Leu, 7.5(8); Lys, 50 3.3(3).

Compound 32

AVSEHOLLHD KGXSIODLRR RELLEKLLEK LHTA-NH$_2$ (SEQ ID NO:46)

Ala Val Ser Glu His Gln Leu Leu His Asp Lys Gly Xaa Ser Ile
1               5                   10                  15

Gln Asp Leu Arg Arg Arg Glu Leu Leu Glu Lys Leu Leu Glu Lys
                20                  25                  30

Leu His Thr Ala NH$_2$, (Xaa = Cys(CH$_2$CONH(CH$_2$)$_2$NH(biotinyl))), (SEQ ID NO:46)

Physical Data: m.p. (not determined) $[\alpha]_D^{25}$ (not determined)

FAB(C$_{186}$H$_{316}$N$_{59}$O$_{54}$S$_2$): [M+H]$^+$4306.6

AAA: Asx, 2.2(2); Glx, 6.1(6); Ser, 1.8(2); His, 3.8(3); Gly, 1.0(1); Thr, 1.0(1); Ala, 2.0(2); Arg, 3.1(3); Val, 1.1(1); Ile, 0.9(1); Leu, 8.3(3); Lys, 3.3(3).

Compound 33

AVSEHOLLHD KGXSIODLRR RELLEKLLEK LHTA-NH$_2$ (SEQ ID NO:47) (X=Lys(7-dimethylamino-2-oxo-2H-1-benxopyran-4-acetyl)

Ala Val Ser Glu His Gln Leu Leu His Asp Lys Gly Xaa Ser Ile
1               5                   10                  15

Gln Asp Leu Arg Arg Arg Glu Leu Leu Glu Lys Leu Leu Glu Lys
                20                  25                  30

Leu His Thr Ala NH$_2$, (Xaa = Lys(7-dimethylamino-2-oxo-2H-1-benxopyran-4-acetyl), (SEQ ID NO:47)

Physical Data: m.p. 135°–205° C. $[\alpha]_D^{25}$ –26.92 (c 0.104, 50% aq. HOAc)

FAB (C$_{188}$H$_{311}$N$_{57}$O$_{54}$): [M+H]$^+$4233

AAA: Asx, 1.9(2); Glx, 6.3(6); Ser, 1.7(2); His, 3.2(3); Gly, 1.0(1); Thr, 1.1(1); Ala, 2.0(2); Arg, 3.2(3); Val, 1.1(1); Ile, 0.9(1); Leu, 8.2(8); Lys, 4.5(4).

Compound 34

AVSEHOLLHD KGKSIODLRR RELLEKLLEK LHTAG-OH (SEQ ID NO:48)

Ala Val Ser Glu His Gln Leu Leu His Asp Lys Gly Lys Ser Ile
1               5                   10                  15

Gln Asp Leu Arg Arg Arg Glu Leu Leu Glu Lys Leu Leu Glu Lys
                20                  25                  30

Leu His Thr Ala Gly OH (SEQ ID NO:48)
                35

Physical Data: m.p. 92.1°–146.6° C. $[\alpha]_D^{25}$ –40.76 (c 0.34, H$_2$O)

FAB (C$_{177}$H$_{302}$N$_{56}$O$_{53}$): [M+H]$^+$4062.0

AAA: Asx, 2.0(2); Glx, 5.7(6); Ser, 1.8(2); His, 3.0(3); Gly, 2.2(2); Thr, 0.9(1); Ala, 1.9(2); Arg, 2.8(3); Val, 1.2(1); Ile, 0.9(1); Leu, 7.5(8); Lys, 4.2(4).

Compound 35

AVSX$_1$HOLLHX$_2$ KGKSIOX$_2$LRR RX$_1$LLXKLLX$_1$K LHA-OH (SEQ ID NO:49) (X$_1$=Glu(OCH$_3$); X$_2$=Asp (OCH$_3$))

Ala Val Ser Xaa$_1$ His Gln Leu Leu His Xaa$_2$ Lys Gly Lys Ser Ile
1                 5                       10                  15

Gln Xaa$_2$ Leu Arg Arg Arg Xaa$_1$ Leu Leu Xaa$_1$ Lys Leu Leu Xaa$_1$ Lys
                          20                  25                  30

Leu His Ala OH (Xaa₁ = Glu(OCH₃); Xaa₂ = Asp(OCH₃))
(SEQ ID NO:49)

Physical Data: m.p. (not determined) $[\alpha]_D^{25}$ –21.96 (c 0.132, H₂O)

FAB($C_{181}H_{311}N_{55}O_{52}$): [M+H]⁺4089.0

AAA: Asx, 2.1(2); Glx, 6.3(6); Ser, 1.8(2); His, 3.3(3); Gly, 1.1(1); Thr, 1.0(1); Ala, 2.0(2); Arg, 3.1(3); Val, 1.1(1); Ile, 0.9(1); Leu, 8.0(8); Lys, 4.2(4).

Compound 36

AVSX₁HOLLHX₂ KGKSIOX₂LRR RX₁LLX₁KLLX₁K LHA-OCH₃ (SEQ ID NO:50) (X₁=Glu(OCH₃); X₂=Asp(OCH₃))

```
Ala Val Ser Xaa₁His Gln Leu Leu His Xaa₂Lys Gly Lys Ser Ile
 1           5                   10              15
Gln Xaa₂Leu Arg Arg Arg Xaa₁Leu Leu Xaa₁Lys Leu Leu Xaa₁Lys
       20                25              30
Leu His Ala OCH₃ (Xaa₁ = Glu(OCH₃); Xaa₂ = Asp(OCH₃))
(SEQ ID NO:50)
```

Physical Data: m.p. (not determined) $[\alpha]_D^{25}$ –46.80 (c 0.07, H₂O)

FAB ($C_{182}H_{313}N_{55}O_{52}$): [M+H]⁺4103

AAA: Asx, 2.1(2); Glx, 6.2(6); Ser, 1.4(2); His, 3.0(3); Gly, 1.1(1); Thr, 1.1(1); Ala, 1.7(2); Arg, 3.2(3); Val, 0.6(1); Ile, 0.9(1); Leu, 8.0(8); Lys, 4.1(4).

Compound 38

AVSEHOLLHD KGKSIODLRR RELLEKLLEK LHTAP-OH (SEQ ID NO:52)

```
Ala Val Ser Glu His Gln Leu Leu His Asp Lys Gly Lys Ser Ile
 1           5                   10              15
Gln Asp Leu Arg Arg Arg Glu Leu Leu Glu Lys Leu Leu Glu Lys
              20                  25              30
Leu His Thr Ala Pro OH (SEQ ID NO:52)
        35
```

Physical Data: m.p. 152.1°–186.5° C. $[\alpha]_D^{25}$ –55.91 (c 0.33, H₂O)

FAB ($C_{180}H_{306}N_{56}O_{53}$): [M+H]⁺4102.6

AAA: Asx, 2.0(2); Glx, 5.6(6); Ser, 1.7(2); His, 2.9(3); Gly, 1.1(1); Thr, 0.9(1); Ala, 1.9(2); Arg, 2.9(3); Val, 1.2(1); Ile, 1.0(1); Leu, 7.7(8); Lys, 4.3(4).

Compound 39

AVSEHOLLHD KGKSIODLRR RELLEKLLEK LHTP-OH (SEQ ID NO:53)

```
Ala Val Ser Glu His Gln Leu Leu His Asp Lys Gly Lys Ser Ile
 1           5                   10              15
Gln Asp Leu Arg Arg Arg Glu Leu Leu Glu Lys Leu Leu Glu Lys
              20                  25              30
Leu His Thr Pro OH (SEQ ID NO:53)
```

Physical Data: m.p. 120°–148.2° C. $[\alpha]_D^{25}$ –52.78 (c 0.47, H₂O)

FAB($C_{177}H_{301}N_{55}O_{52}$): [M+H]⁺4031.0

AAA: Asx, 2.0(2); Glx, 5.5(6); Ser, 1.8(2); His, 2.9(3); Gly, 1.0(1); Thr, 1.0(1); Ala, 0.9(1); Arg, 2.9(3); Val, 1.2(1); Ile, 0.9(1); Leu, 7.5(8); Lys, 3.6(3); Pro, 0.9(1).

Compound 40

AVSEHOLLHD KGKSIODLRR RELLEKLLEK LHTP-NH₂ (SEQ ID NO:54)

```
Ala Val Ser Glu His Gln Leu Leu His Asp Lys Gly Lys Ser Ile
 1           5                   10              15
Gln Asp Leu Arg Arg Arg Glu Leu Leu Glu Lys Leu Leu Glu Lys
              20                  25              30
Leu His Thr Pro NH₂ (SEQ ID NO:54)
```

Physical Data: m.p. 133.9°–155.1° C. $[\alpha]_D^{25}$ –54.22 (c 0.37, H₂O)

FAB($C_{177}H_{302}N_{56}O_{51}$): [M+H]⁺4030.7

AAA: Asx, 2.0(2); Glx, 5.6(6); Ser, 1.9(2); His, 2.9(3); Gly, 1.1(1); Thr, 0.9(1); Ala, 0.9(1); Arg, 2.8(3); Val, 1.2(1); Ile, 1.1(1); Leu, 7.8(8); Lys, 4.2(4); Pro, 0.9(1).

Compound 41

AVSEHOLLHD KGKSIODLRR RELLEKLLEK LHP-NH₂ (SEQ ID NO:55)

```
Ala Val Ser Glu His Gln Leu Leu His Asp Lys Gly Lys Ser Ile
 1           5                   10              15
Gln Asp Leu Arg Arg Arg Glu Leu Leu Glu Lys Leu Leu Glu Lys
              20                  25              30
Leu His Pro NH₂ (SEQ ID NO:55)
```

Physical Data: m.p. 142.8°–166.1° C. $[\alpha]_D^{25}$ –53.80 (c 0.38, H₂O)

FAB ($C_{173}H_{295}N_{55}O_{49}$): [M+H]⁺3929

AAA: Asx, 2.0(2); Glx, 5.7(6); Ser, 1.8(2); His, 3.0(3); Gly, 1.1(1); Ala, 0.9(1); Arg, 2.8(3); Val, 1.2(1); Ile, 0.9(1); Leu, 7.4(8); Lys, 4.4(4); Pro, 0.9(1).

Compound 42

AVSEHOLLHD KGKSIODLRR RELLEKLLEK LP-NH₂ (SEQ ID NO:56)

| Ala | Val | Ser | Glu | His | Gln | Leu | Leu | His | Asp | Lys | Gly | Lys | Ser | Ile |
|-----|-----|-----|-----|-----|-----|-----|-----|-----|-----|-----|-----|-----|-----|-----|
| 1   |     |     |     | 5   |     |     |     |     | 10  |     |     |     |     | 15  |

| Gln | Asp | Leu | Arg | Arg | Arg | Glu | Leu | Leu | Glu | Lys | Leu | Leu | Glu | Lys |
|-----|-----|-----|-----|-----|-----|-----|-----|-----|-----|-----|-----|-----|-----|-----|
|     |     |     |     | 20  |     |     |     |     | 25  |     |     |     |     | 30  |

| Leu | Pro | NH₂ | (SEQ ID NO:56) |

Physical Data: m.p. 161.0°–177.0° C. $[\alpha]_D^{25}$ –61.97 (c 0.19, H₂O)

FAB($C_{167}H_{288}N_{52}O_{48}$): [M+H]⁺3792.0

AAA: Asx, 2.2(2); Glx, 5.9(6); Ser, 1.9(2); His, 2.1(2); Gly, 1.1(1); Ala, 1.0(3); Arg, 3.0(3); Val, 1.1(1); Ile, 1.0(1); Leu, 7.9(8); Lys, 4.3(4); Pro, 0.9(1).

Compound 43

AVSEHOLLHD KGKSIODLRR RELLEKLLEK LHTRSAW-OH (SEQ ID NO:57)

| Ala | Val | Ser | Glu | His | Gln | Leu | Leu | His | Asp | Lys | Gly | Lys | Ser | Ile |
|-----|-----|-----|-----|-----|-----|-----|-----|-----|-----|-----|-----|-----|-----|-----|
| 1   |     |     |     | 5   |     |     |     |     | 10  |     |     |     |     | 15  |

| Gln | Asp | Leu | Arg | Arg | Arg | Glu | Leu | Leu | Glu | Lys | Leu | Leu | Glu | Lys |
|-----|-----|-----|-----|-----|-----|-----|-----|-----|-----|-----|-----|-----|-----|-----|
|     |     |     |     | 20  |     |     |     |     | 25  |     |     |     |     | 30  |

| Leu | His | Thr | Arg | Ser | Ala | Trp | OH | (SEQ ID NO:57) |
|-----|-----|-----|-----|-----|-----|-----|-----|----|
|     |     |     |     | 35  |     |     |    |    |

Physical Data: m.p. 181°–202° C. $[\alpha]_D^{25}$ –45.14 (c 0.19, H₂O)

FAB ($C_{195}H_{326}N_{62}O_{56}$): [M+H]⁺4435.2

AAA: Asx, 2.0(2); Glx, 5.8(6); Ser, 2.8(3); His, 2.8(3); Gly, 1.1(1); Thr, 0.9(1); Ala, 1.9(2); Arg, 3.7(4); Ile, 0.9(1); Leu, 7.5(8); Lys, 4.3(4); Trp, 0.9(1).

Compound 44

AVSEHOLLHD RGRSIODLRR RELLERLLER LHTAGRRTRSAW-OH (SEQ ID NO:58)

| Ala | Val | Ser | Glu | His | Gln | Leu | Leu | His | Asp | Arg | Gly | Arg | Ser | Ile |
|-----|-----|-----|-----|-----|-----|-----|-----|-----|-----|-----|-----|-----|-----|-----|
| 1   |     |     |     | 5   |     |     |     |     | 10  |     |     |     |     | 15  |

| Gln | Asp | Leu | Arg | Arg | Arg | Glu | Leu | Leu | Glu | Arg | Leu | Leu | Glu | Arg |
|-----|-----|-----|-----|-----|-----|-----|-----|-----|-----|-----|-----|-----|-----|-----|
|     |     |     |     | 20  |     |     |     |     | 25  |     |     |     |     | 30  |

| Leu | His | Thr | Arg | Gly | Arg | Arg | Thr | Arg | Ser | Ala | Trp | OH | (SEQ ID NO:58) |
|-----|-----|-----|-----|-----|-----|-----|-----|-----|-----|-----|-----|----|
|     |     |     |     | 35  |     |     |     |     | 40  |     |     |    |

Physical Data: m.p. 130°–132.2° C. $[\alpha]_D^{25}$ –46.66 (c 0.195, H₂O)

FAB($C_{216}H_{365}N_{81}O_{62}$): [M+H]⁺5088.8

AAA: Asx, 2.2(2); Glx, 6.0(6); Ser, 2.7(3); His, 3.0(3); Gly, 2.2(2); Thr, 2.1(2); Ala, 3.0(3); Arg, 10.5(10); Val, 0.9(1); Ile, 1.0(1); Leu, 8.2(8); Trp, 1.0(1).

Compound 45

AVSEHOLLHD RGRSIODLRR RELLERLLER LHTAGRRTRSAW-NH₂ (SEQ ID NO:59)

| Ala | Val | Ser | Glu | His | Gln | Leu | Leu | His | Asp | Arg | Gly | Arg | Ser | Ile |
|-----|-----|-----|-----|-----|-----|-----|-----|-----|-----|-----|-----|-----|-----|-----|
| 1   |     |     |     | 5   |     |     |     |     | 10  |     |     |     |     | 15  |

| Gln | Asp | Leu | Arg | Arg | Arg | Glu | Leu | Leu | Glu | Arg | Leu | Leu | Glu | Arg |
|-----|-----|-----|-----|-----|-----|-----|-----|-----|-----|-----|-----|-----|-----|-----|
|     |     |     |     | 20  |     |     |     |     | 25  |     |     |     |     | 30  |

| Leu | His | Thr | Arg | Gly | Arg | Arg | Thr | Arg | Ser | Ala | Trp | NH₂ | (SEQ ID NO:59) |
|-----|-----|-----|-----|-----|-----|-----|-----|-----|-----|-----|-----|-----|
|     |     |     |     | 35  |     |     |     |     | 40  |     |     |     |

Physical Data: m.p. 158°–174° C. $[\alpha]_D^{25}$ –43.57 (c 0.53, $H_2O$)

FAB ($C_{216}H_{366}N_{82}O_{61}$) : $[M+H]^+$ 5087.4

AAA: Asx, 1.9(2); Glx, 5.6(6); Ser, 2.6(3); His, 3.3(3); Gly, 2.1(2); Thr, 2.0(2); Ala, 2.9(3); Arg, 10.1(10); Val, 0.9(1); Ile, 1.0(1); Leu, 8.3(8); Trp 1.1(1).

Compound 46

AVSEHOLLHD RGXSIODLRR RELLERLLER LHTAGRRTRSAW-OH (SEQ ID NO:60) (X=Lys (dihydrocinnamoyl))

| Ala | Val | Ser | Glu | His | Gln | Leu | Leu | His | Asp | Arg | Gly | Xaa | Ser | Ile |
|-----|-----|-----|-----|-----|-----|-----|-----|-----|-----|-----|-----|-----|-----|-----|
| 1   |     |     |     | 5   |     |     |     |     | 10  |     |     |     |     | 15  |
| Gln | Asp | Leu | Arg | Arg | Arg | Glu | Leu | Leu | Glu | Arg | Leu | Leu | Glu | Arg |
|     |     |     |     | 20  |     |     |     |     | 25  |     |     |     |     | 30  |
| Leu | His | Thr | Arg | Gly | Arg | Arg | Thr | Arg | Ser | Ala | Trp | OH | (Xaa = | |
|     |     |     |     | 35  |     |     |     |     | 40  |     |     |    |        | |

Lys (dihydrocinnamoyl), (SEQ ID NO:60)

Lys (dihydrocinnamoyl), (SEQ ID NO:60)

Physical Data: m.p. 165.4°–175.2° C. $[\alpha]_D^{25}$ –40.43 (c 0.20, $H_2O$)

FAB ($C_{225}H_{374}N_{80}O_{62}$): $[M+H]^+$ 5191

AAA: Asx, 2.1(2), Glx, 6.3(6); Ser, 2.8(3); His, 3.2(3); Gly, 2.1(2), Thr, 2.0(2); Ala, 3.2(3); Arg, 9.9(9); Val, 1.0(1), Ile, 0.9(1); Leu, 8.6(8); Lys, 1.1(1); Trp, 1.1(1).

Compound 47

AVSEIOFXHN LGKHLSSXTR SAWLRKKLOD VHNY-$NH_2$ (SEQ ID NO:61)

| Ala | Val | Ser | Glu | Ile | Gln | Phe | Nle | His | Asn | Leu | Gly | Lys | His | Leu |
|-----|-----|-----|-----|-----|-----|-----|-----|-----|-----|-----|-----|-----|-----|-----|
| 1   |     |     |     | 5   |     |     |     |     | 10  |     |     |     |     | 15  |
| Ser | Ser | Nle | Thr | Arg | Ser | Ala | Trp | Leu | Arg | Lys | Lys | Leu | Gln | Asp |
|     |     |     |     | 20  |     |     |     |     | 25  |     |     |     |     | 30  |
| Val | His | Asn | Tyr | $NH_2$ (SEQ ID NO:61) | | | | | | | | | | |

Physical Data: m.p. 140°–160° C. $[\alpha]_D^{25}$ –56.88 (c 0.16, $H_2O$)

FAB ($C_{180}H_{287}N_{55}O_{58}$): $[M+H]^+$ 3989.8

AAA: Asx, 3.0(3); Glx, 2.9(3); Ser, 3.7(4); His, 2.8(3); Gly, 1.1(1); Thr, 0.9(1); Ala, 1.9(2); Arg, 2.0(2); Tyr, 1.0(1); Val, 1.7(2); Phe, 0.9(1); Ile, 0.9(1); Leu+Nle 5.8(2+4); Lys, 3.4(3); Trp, 1.1(1).

Compound 48

AVSEHOLLHD KGKSIODLRR RELLEKLLEK LHTMA-$NH_2$ (SEQ ID NO: 62)

| Ala | Val | Ser | Glu | His | Gln | Leu | Leu | His | Asp | Lys | Gly | Lys | Ser | Ile |
|-----|-----|-----|-----|-----|-----|-----|-----|-----|-----|-----|-----|-----|-----|-----|
| 1   |     |     |     | 5   |     |     |     |     | 10  |     |     |     |     | 15  |
| Gln | Asp | Leu | Arg | Arg | Arg | Glu | Leu | Leu | Glu | Lys | Leu | Leu | Glu | Lys |
|     |     |     |     | 20  |     |     |     |     | 25  |     |     |     |     | 30  |
| Leu | His | Thr | Met | Ala | $NH_2$ (SEQ ID NO:62) | | | | | | | | | |
|     |     |     |     | 35  |     | | | | | | | | | |

Physical Data: m.p. 140°–210° C. $[\alpha]_D^{25}$ –47.75(c 0.178, $H_2O$)

FAB ($C_{180}H_{309}N_{57}O_{52}S_1$): $[M+H]^+$ 4135.0

AAA: Asx, 2.3(2); Glx, 6.6(6); Ser, 1.4(2); His, 3.2(3); Gly, 1.1(1); Thr, 1.0(1); Ala, 2.0(2); Arg, 3.1(3); Val, 0.9(1); Met, 1.1(1); Ile, 1.0(1); Leu, 8.8(8); Lys, 4.4(4).

Compound 50

AVSEHOLLHD KGKSIODLRR RFFLEKLLEK LHTA-NH₂ (SEO ID NO:64)

```
Ala  Val  Ser  Glu  His  Gln  Leu  Leu  His  Asp  Lys  Gly  Lys  Ser  Ile
1              5                        10                       15

Gln  Asp  Leu  Arg  Arg  Arg  Phe  Phe  Leu  Glu  Lys  Leu  Leu  Glu  Lys
                    20                  25                       30

Leu  His  Thr  Ala  NH₂  (SEQ ID NO:64)
                    35
```

Physical Data: m.p. 136.5°–156.8° C. $[\alpha]_D^{25}$-49.89 (c 0.24, H₂O)

FAB ($C_{182}H_{300}N_{56}O_{49}$): [M+H]⁺4056.0

AAA: Asx, 2.2(2); Glx, 5.0(5); Ser, 1.9(2); His, 3.3(3); Gly, 1.0(1); Thr, 1.0(1); Ala, 2.1(2); Arg, 3.1(3); Val, 1.0(1); Phe, 2.0(2); Ile, 0.9(1); Leu, 7.2(7); Lys, 3.5(4).

Compound 51

AVSEHOLLHD KGKSIODLRR RELLHKLLEK LHTA-NH₂ (SEO ID NO: 65)

```
Ala  Val  Ser  Glu  His  Gln  Leu  Leu  His  Asp  Lys  Gly  Lys  Ser  Ile
1              5                        15                       20

Gln  Asp  Leu  Arg  Arg  Arg  Glu  Leu  Leu  His  Lys  Leu  Leu  Glu  Lys
                    20                  25                       30

Leu  His  Thr  Ala  NH₂  (SEQ ID NO:65)
```

Physical Data: m.p. 80.7°–141.0° C. $[\alpha]_D^{25}$-55.38 (c 0.23, H₂O)

FAB ($C_{176}H_{300}N_{58}O_{49}$): [M+H]⁺4012.8

AAA: Asx, 2.2(2); Glx, 4.9(5); Ser, 1.8(2); His, 4.3(4); Gly, 1.1(1); Thr, 1.0(1); Ala, 2.0(2); Arg, 3.1(3); Val, 1.1(1); Ile, 1.0(1); Leu, 8.1(8); Lys, 3.9(4).

Compound 52

AVSEHOLLHD KGKSIODLRR RELLEHLLEK LHTA-NH₂ (SEO ID NO:66)

```
Ala  Val  Ser  Glu  His  Gln  Leu  Leu  His  Asp  Lys  Gly  Lys  Ser  Ile
1              5                        10                       15

Gln  Asp  Leu  Arg  Arg  Arg  Glu  Leu  Leu  Glu  His  Leu  Leu  Glu  Lys
                    20                  25                       30

Leu  His  Thr  Ala  NH₂  (SEQ ID NO:66)
```

Physical Data: m.p. 134.3°–157.9° C. $[\alpha]_D^{25}$-50.72 (c 0.45, H₂O)

FAB ($CC_{175}H_{295}N_{57}O_{51}$): [M+H]⁺4012.8

AAA: Asx, 2.1(2); Glx, 5.9(6); Ser, 1.8(2); His, 4.2(4); Gly, 1.1(1); Thr, 1.0(1); Ala, 2.0(2); Arg, 3.0(3); Val, 1.1(1); Ile, 0.9(1); Leu, 8.1(8); Lys, 3.1(3).

Compound 53

AVSEHOLLHD KGKSIODLRR RELLEKLIAK LHTA-NH₂ (SEO ID NO:67)

```
Ala  Val  Ser  Glu  His  Gln  Leu  Leu  His  Asp  Lys  Gly  Lys  Ser  Ile
1              5                        10                       15

Gln  Asp  Leu  Arg  Arg  Arg  Glu  Leu  Leu  Glu  Lys  Leu  Ile  Ala  Lys
                    20                  25                       30
```

Leu His Thr Ala NH₂ (SEQ ID NO:67)

Physical Data: m.p. 142.7°–159.8° C [α]$_D^{25}$ –54.01 (c 0.21, H₂O)

FAB (C₁₇₃H₂₉₈N₅₆O₄₉): [M+H]⁺3946.0

AAA: Asx, 2.2(2); Glx, 4.9(5); Ser, 1.8(2); His, 3.1(3); Gly, 1.1(1); Thr, 1.0(1); Ala, 3.1(3); Arg, 3.1(3); Val, 1.0(1); Ile, 1.9(2); Leu, 7.0(7); Lys, 4.3(4).

Compound 54

AVSEHOLLHD KGKSIODLRR RELLEKLLEE IHTA-NH₂ (SEQ ID NO:68)

| Ala | Val | Ser | Glu | His | Gln | Leu | Leu | His | Asp | Lys | Gly | Lys | Ser | Ile |
|---|---|---|---|---|---|---|---|---|---|---|---|---|---|---|
| 1 | | | | 5 | | | | | 10 | | | | | 15 |
| Gln | Asp | Leu | Arg | Arg | Arg | Glu | Leu | Leu | Glu | Lys | Leu | Leu | Glu | Glu |
| | | | | 20 | | | | | 25 | | | | | 30 |
| Ile | His | Thr | Ala | NH₂ | (SEQ ID NO:68) | | | | | | | | | |

Physical Data: m.p. 138°–185° C. [α]$_D^{25}$ –50.17 (c 0.1, H₂O)

FAB(C₁₇₄H₂₉₅N₅₅O₅₃): [M+H]⁺4005

AAA: Asx, 2.2(2); Glx, 7.1(7); Ser, 1.7(2); His, 2.8(3); Gly, 1.0(1); Thr, 1.0(1); Ala, 2.1(2); Arg, 3.1(3); Val, 1.1(1); Ile, 1.7(2); Leu, 7.1(7); Lys, 2.7(3).

Compound 58

AVSEHOLLHD KGKSIODLRR RELLEKLLEK LHTRSAW-NH₂ (SEQ ID NO:72)

| Als | Val | Ser | Glu | His | Gln | Leu | Leu | His | Asp | Lys | Gly | Lys | Ser | Ile |
|---|---|---|---|---|---|---|---|---|---|---|---|---|---|---|
| 1 | | | | 5 | | | | | 10 | | | | | 15 |
| Gln | Asp | Leu | Arg | Arg | Arg | Glu | Leu | Leu | Glu | Lys | Leu | Leu | Glu | Lys |
| | | | | 20 | | | | | 25 | | | | | 30 |
| Leu | His | Thr | Arg | Ser | Ala | Trp | NH₂ | (SEQ ID NO:72) | | | | | | |
| | | | | 35 | | | | | | | | | | |

Physical Data: m.p. 158°–163° C. [α]$_D^{25}$ –46.06 (c 0.17, H₂O)

FAB(C₁₉₅H₃₂₇N₆₃O₅₅): [M+H]⁺4434.8

AAA: Asx, 2.0(2); Glx, 5.5(6); Ser, 2.7(3); His, 3.1(3); Gly, 1.0(1); Ala, 1.8(2); Arg, 4.0(4); Thr, 0.9(1); Val, 0.9(1); Ile, 0.9(1); Leu, 7.5(8); Lys, 3.9(4); Trp, 1.0(1).

Compound 59

AVSEHOLLHD KGKSIODLRR RELLEKLLEK LHTRSAX-OH (SEQ ID NO:73) (X=Nal(2)=3-(2-naphthyl)-L-alanine)

| Ala | Val | Ser | Glu | His | Gln | Leu | Leu | His | Asp | Lys | Gly | Lys | Ser | Ile |
|---|---|---|---|---|---|---|---|---|---|---|---|---|---|---|
| 1 | | | | 5 | | | | | 10 | | | | | 15 |
| Gln | Asp | Leu | Arg | Arg | Arg | Glu | Leu | Leu | Glu | Lys | Leu | Leu | Glu | Lys |
| | | | | 20 | | | | | 25 | | | | | 30 |
| Leu | His | Thr | Arg | Ser | Ala | 3-(2naphthly)-L-alanine-OH (SEQ ID NO:73) | | | | | | | | |
| | | | | 35 | | | | | | | | | | |

Physical Data: m.p. 156°–162° C. [α]$_D^{25}$ –44.44 (c 0.189, H₂O)

FAB (C₁₉₇H₃₂₈N₆₂O₅₅): [M+H]⁺4445.6

AAA: Asx, 2.1(2); Glx, 5.5(6); Ser, 2.8(3); His, 2.9(3); Gly, 1.0(1); Ala, 2.0(2); Arg, 4.0(4); Thr, 0.9(1); Val, 1.0(1); Ile, 0.9(1); Leu, 7.5(8); Lys, 4.2(4); Nal, 1.1(1).

Compound 60

AVSEHOLLHD KGKSIODLRR RELLEKLLEK LHTASAW-OH (SEQ ID NO:74)

Ala Val Ser Glu His Gln Leu Leu His Asp Lys Gly Lys Ser Ile
1           5                  10                15

Gln Asp Leu Arg Arg Arg Glu Leu Leu Glu Lys Leu Leu Glu Lys
                20                  25                30

Leu His Thr Ala Ser Ala Trp OH (SEQ ID NO:74)
                35

Physical Data: m.p. 159°–164° C. $[\alpha]_D^{25}$ –50.94 (c 0.29, H$_2$O)

FAB ($C_{192}H_{32}ON_{60}O_{55}$): [M+H]$^+$4349.0

AAA: Asx, 2.0(2); Glx, 5.6(6); Ser, 2.7(3); His, 3.2(3); Gly, 1.0(1); Ala, 3.1(3); Arg, 2.8(3); Thr, 1.0(1); Val, 1.1(1); Ile, 0.9(1); Leu, 7.6(8); Lys, 4.0(4); Trp, 1.0(1).

Compound 61

AVSEHOLLHD KGKSIODLRR RELLEKLLEK LHTAEIRA-OH (SEQ ID NO:74)

Ala Val Ser Glu His Gln Leu Leu His Asp Lys Gly Lys Ser Ile
1           5                  10                15

Gln Asp Leu Arg Arg Arg Glu Leu Leu Glu Lys Leu Leu Glu Lys
                20                  25                30

Leu His Thr Ala Glu Ile Arg Ala OH (SEQ ID NO:75)
                35

Physical Data: m.p. 155°–210° C. $[\alpha]_D^{25}$ –46.15 (c 0.12, H$_2$O)

FAB ($C_{195}H_{334}N_{62}O_{58}$): [M+H]$^+$4475.8

AAA: Asx, 2.2(2); Glx, 6.9(7); Ser, 1.7(2); His, 3.2(3); Gly, 1.1(1); Ala, 3.1(3); Arg, 4.0(4); Thr, 0.9(1); Val, 1.1(1); Ile, 1.9(2); Leu, 8.1(8); Lys, 4.1(4).

Compound 62

AVSEHOLLHD KGKSIODLRR RELLEKLLEK LHTAEIR-OH (SEQ ID NO:76)

Ala Val Ser Glu His Gln Leu Leu His Asp Lys Gly Lys Ser Ile
1           5                  10                15

Gln Asp Leu Arg Arg Arg Glu Leu Leu Glu Lys Leu Leu Glu Lys
                20                  25                30

Leu His Thr Ala Glu Ile Arg OH (SEQ ID NO:76)
                35

Physical Data: m.p. 186°–218° C. $[\alpha]_D^{25}$ –52.73 (c 0.265, H$_2$O)

FAB ($C_{192}H_{329}N_{61}O_{57}$): [M+H]$^+$4404.4

AAA: Asx, 2.0(2); Glx, 6.6(7); Ser, 1.9(2); His, 3.4(3); Gly, 1.1(1); Ala, 2.0(2); Arg, 3.8(4); Thr, 1.0(1); Val, 1.1(1); Ile, 1.7(2); Leu, 7.9(8); Lys, 4.0(4).

Compound 63

AVSEHOLLHD KGKSIODLRR RELLEKLLEK LHTAEI-OH (SEQ ID NO:77)

Ala Val Ser Glu His Gln Leu Leu His Asp Lys Gly Lys Ser Ile
1           5                  10                15

Gln Asp Leu Arg Arg Arg Glu Leu Leu Glu Lys Leu Leu Glu Lys
                20                  25                30

Leu His Thr Ala Glu Ile OH (SEQ ID NO:77)
                35

Physical Data: m.p. 169°–205° C. $[\alpha]_D^{25}$ –50.78 (c 0.51, H$_2$O)

FAB ($C_{186}H_{317}N_{57}O_{56}$): [M+H]$^+$4248.0

AAA: Asx, 2.2(2); Glx, 6.8(7); Ser, 1.8(2); His, 3.3(3); Gly, 1.0(1); Ala, 2.0(2); Arg, 3.0(3); Thr, 1.0(1); Val, 1.0(1); Ile, 1.8(2); Leu, 7.8(8); Lys, 3.6(4).

Compound 64

AVSEHOLLHD KGKSIODLRR RELLEKLLEK LHTAE-OH (SEQ ID NO:78),

Ala Val Ser Glu His Gln Leu Leu His Asp Lys Gly Lys Ser Ile
1           5                  10                15

Gln Asp Leu Arg Arg Arg Glu Leu Leu Glu Lys Leu Leu Glu Lys
                20                  25                30

Leu His Thr Ala Glu OH (SEQ ID NO:78)
                35

Physical Data: m.p. 199°–205° C. $[\alpha]_D^{25}$ –52.47 (c 0.41, H$_2$O)

FAB (C180H$_{306}$N$_{56}$O$_{55}$): [M+H]$^+$4135.0

AAA: Asx, 2.0(2); Glx, 6.6(7); Ser, 1.9(2); His, 3.3(3); Gly, 1.1(1); Ala, 2.0(2); Arg, 2.9(3); Thr, 1.0(1); Val, 1.1(1); Ile, 1.0(1); Leu, 8.2(8); Lys, 3.8(4).

Compound 66

SEHOLLHD KGKSIODLRR RELLEKLLEK LHTA-NH$_2$ (SEQ ID NO:80)

Ser Glu His Gln Leu Leu His Asp Lys Gly Lys Ser Ile Gln Asp
1           5                  10                15

Leu Arg Arg Arg Glu Leu Leu Glu Lys Leu Leu Glu Lys Leu His
                20                  25                30

Thr Ala NH$_2$ (SEQ ID NO:80)

Physical Data: m.p. 134.2° C. $[\alpha]_D^{25}$ –48.12(c 0.36, H$_2$O)

FAB ($C_{167}H_{286}N_{54}O_{49}$): [M+H]$^+$3834.4

AAA: Asx, 2.0(2); Glx, 5.7(6); Ser, 1.7(2); His, 2.9(3); Gly, 1.0(1); Thr, 0.9(1); Ala, 1.0(1); Arg, 2.8(3); Ile, 0.9(1); Leu, 7.4(8); Lys, 4.3(4).

Compound 67

LLHD KGKSIODLRR RELLEKLLEK LHTA-NH$_2$ (SEQ ID NO:81)

Leu Leu His Asp Lys Gly Lys Ser Ile Gln Asp Leu Arg Arg Arg
1               5               10                  15
Glu Leu Leu Glu Lys Leu Leu Glu Lys Leu His Thr Ala NH$_2$
            20                  25

(SEQ ID NO:81)

Physical Data: m.p. 128.5°–184.5° C. $[\alpha]_D^{25}$ –6.53 (c 0.69, MeOH)

FAB (C$_{148}$H$_{259}$N$_{47}$O$_{41}$): [M+H]$^+$3353

AAA: Asx, 2.0(2); Glx, 4.1(4); Ser, 0.9(1); His, 2.1(2); Gly, 1.0(1); Thr, 0.9(1); Ala, 1.0(1); Arg, 3.0(3); Ile, 1.0(1); Leu, 8.1(8); Lys, 4.2(4).

Compound 68

LHD KGKSIODLRR RELLEKLLEK LHTA-NH$_2$ (SEQ ID NO: 82)

Leu His Asp Lys Gly Lys Ser Ile Gln Asp Leu Arg Arg Arg Glu
1               5               10                  15
Leu Leu Glu Lys Leu Leu Glu Lys Leu His Thr Ala NH2 (SEQ
            20                  25

ID NO:82)

Physical Data: m.p. 165°–210° C. $[\alpha]_D^{25}$ –36.05(c 0.12, H$_2$O)

FAB (C$_{142}$H$_{248}$N$_{46}$O$_{40}$): [M+H]$^+$3239.0

AAA: Asx, 2.0(2); Glx, 3.9(4); Ser, 0.9(1); His, 1.9(2); Gly, 1.0(1); Thr, 1.0(1); Ala, 1.0(1); Arg, 2.9(3); Ile, 0.9(1); Leu, 6.8(7); Lys, 4.2(4).

Compound 69

SEHQLLHD RGRSIODLRR RELLERLLER LHAGRRTRSAW-OH (SEQ ID NO:83)

Ser Glu His Gln Leu Leu His Asp Arg Gly Arg Ser Ile Gln Asp
1               5               10                  15
Leu Arg Arg Arg Glu Leu Leu Glu Arg Leu Leu Glu Arg Leu His
            20                  25                  30
Leu His Arg Gly Arg Arg Thr Arg Ser Ala Trp OH (SEQ ID
            35                  40

NO:83)

Physical Data: m.p. 150°–210° C. $[\alpha]_D^{25}$ –18.0 (c 0.64, H$_2$O)

FAB (C$_{208}$H$_{351}$N$_{79}$O$_{60}$): [M+H]$^+$4918.6

AAA: Asx, 2.2(2); Glx, 6.2(6); Ser, 2.8(3); His, 3.1(3); Gly, 2.2(2); Thr, 2.2(2); Ala, 2.2(2); Arg, 10.4(10); Ile, 1.0(1); Leu, 8.0(8); Trp, 1.1(1).

Compound 70

LLHD RGRSIODLRR RELLERLLER LHAGRRTRSAW-OH (SEQ ID NO:84)

Leu Leu His Asp Arg Gly Arg Ser Ile Gln Asp Leu Arg Arg Arg
1               5               10                  15
Glu Leu Leu Glu Arg Leu Leu Glu Arg Leu His Leu His Arg Gly
            20                  25                  30
Arg Arg Thr Arg Ser Ala Trp OH (SEQ ID NO:84)
            35

Physical Data: m.p. 150°614 210° C. $[\alpha]_D^{25}$ –41.70(c 0.36, H$_2$O)

FAB (C$_{189}$H$_{324}$N$_{72}$O$_{52}$): [M+H]$^+$4437.14

AAA: Asx, 2.1(2); Glx, 4.1(4); Ser, 1.9(2); His, 2.0(2); Gly, 2.1(2); Thr, 2.0(2); Ala, 2.1(2); Arg, 9.7(10); Ile, 0.9(1); Leu, 7.4(8).

The side chain cyclized analog (Compound 57) was synthesized as above except the N$^\alpha$-Boc-N$^\epsilon$-Fmoc-Lys and N$^\alpha$-Boc-N$^\gamma$-Fmoc-Asp were placed in positions 13 and 17, respectively. Upon completion of the Boc amino acid synthesis, the resin was traated with 20% piperidine in DMF at room termperature for 30 minutes. The resin was filtered and washed with DMF, MeOH and CH$_2$Cl$_2$. The resin (1.1 g) was suspended in 10 ml DMF containing 250 mg PyBOP. The pH was adjusted to 8–9 with DIEA and the resin stirred for 1 hour. The resin was filtered, washed with DMF and CH$_2$Cl$_{21}$ then resuspended in DMF. The coupling was repeated using 125 mg of PyBOP. The resin was filtered, washed with DMF, MeOH, and CH$_2$Cl$_2$ and dried. The resin was then treated with HF and the peptide purified as mentioned above.

Compound 57

AVSEHQLLHD KGKSIODLRR RELLEKLLEK LHTA-NH$_2$ (SEQ ID NO:71)

```
                    ┌─────────────────┐
AVSEHQLLHD KGKSIODLRR RELLEKLLEK LHTA—NH2
              (SEQ ID NO:71)
```

Ala Val Ser Glu His Gln Leu Leu His Asp Lys Gly Lys Ser Ile
1               5               10                  15
Gln Asp Leu Arg Arg Arg Glu Leu Leu Glu Lys Leu Leu Glu Lys
            20                  25                  30
Leu His Thr Ala —NH$_2$ (SEQ ID NO:71)

Physical Data: m.p. 142.5°–163.5° C. $[\alpha]_D^{25}$ –34.31 (c 0.17, H$_2$O)

FAB(C$_{175}$H$_{295}$N$_{56}$O$_{50}$): [M+H]$^+$3986.4

AAA: Asx, 1.9(2); Glx, 5.9(6); Ser, 1.8(2); His, 3.2(3); Gly, 1.1(1); Ala, 2.0(2); Arg, 3.0(3); Thr, 1.0(1); Val, 1.1(1); Ile, 0.9(1); Leu, 8.0(8); Lys, 4.0(4).

EXAMPLE II

[Met$^{34}$, Ala$^{35}$] Compound 1, AVSEHQLLHD-KGKSIQDLRRRELLEKLLEKLHTMA-NH$_2$, (SEQ ID NO:25), was prepared and purified following the procedures of Example I. This polypeptide was converted to the homoserine lactone as follows. The purified peptide (160 mgs) was dissolved in 44% formic acid (4 mL). This solution was combined with a premixed solution of cyanogen bromide (700 mgs) and phenol (1.6 mgs) in 44% formic acid (4 mL) at 0° C. The solution was stirred at 0° C. for 2 hr and at room temperature for 2 hrs. The formation of the product was monitored by HPLC (Vydac® C-18, 300 Å, 4.6×250 mm, flow of 1.2 mL/min, gradient 25–45% acetonitrile in 0.1% TFA over 10 min). The reaction was complete within 4 hr. Half of the sample was concentrated and purified by preparative RP-HPLC (Vydace C-18, gradient 25–45% acetonitrile in 0.1% TFA). The homoserine lactone peptide fractions were pooled and lyophilized to give 28 mgs of white solid of >95% purity, Compound 4.

Compound 4

AVSEHOLLHDKGKSIODLRRRELLEKLLEKLHTX (X=hSerlac. SEQ ID NO:9)

Ala Val Ser Glu His Gln Leu Leu His Asp Lys Gly Lys Ser Ile
1           5                   10              15

Gln Asp Leu Arg Arg Arg Glu Leu Leu Glu Lys Leu Leu Glu Lys
            20                  25              30

Leu His Thr hSerlac (SEQ ID NO:9)

Physical Data: m.p. 138°–142° C. $[\alpha]_D^{25}$ –50.66° (c 0.1, H$_2$O)

FAB ($C_{176}H_{299}N_{55}O_{52}$): [M+H]$^+$4017.61

AAA: Asp, 2.1(2); Glu, 6.1(6); Ser, 1.8(2); His, 3.0(3); Thi, 1.1(1); Ala, 1.1(1); Arg, 2.7(3); Val, 1.0(1); Ile, 1.0(1); Leu, 8.2(8); Lys, 3.8(4); Gly 1.09(1); hSer, 1.09(1).

Similarly, Compound 65 was prepared in accordance with this procedure.

Compound 65

AVSEIOFX$_1$HN KGKHLSSX$_1$ER VEWLRKKLOD VHNX2 (SEQ ID NO:79)

Ala Val Ser Glu Ile Gln Phe Nle His Asn Lys Gly Lys His Leu
1           5                   10              15

Ser Ser Nle Glu Arg Val Glu Trp Leu Arg Lys Lys Leu Gln Asp
            20                  25              30

Val His Asn hSerlac (SEQ ID NO:79)

Physical Data: m.p. 166°–176° C. $[\alpha]_D^{25}$ –52.22 (c 0.25, H$_2$O)

FAB ($C_{180}H288N_{54}O_{50}$): [M+H]$^+$4008.6

AAA: Asx, 3.1(3); Glx, 4.8(5); Ser, 2.9(3); His, 2.9(3); Gly, 1.1(1); Ala, 1.1(1); Arg, 2.0(2); Val, 2.7(3); Phe, 1.0(1); Ile, 1.0(1); Leu +Nle 5.9 (4+2); Lys, 2.8(3).

EXAMPLE III

To prepare the homoserine amide, the crude hSerlactone analog, Compound 4, was concentrated and treated with 25 mL saturated NH$_3$ in methanol. The solution was stirred at 0° C. for 2 hr and at room temperature for 16 hr. The reaction was monitored by HPLC (Vydac® C-18, 300 Å, 4.6×250 mm, flow of 1.2 mL/min, gradient 20–45% acetonitrile in 0.1% TFA) and was complete within 18 hr. The solution was concentrated and purified by preparative RP-HPLC (Vydace® C-18, gradient of 25–45% acetonitrile in 0.1% TFA). The homoserine amide peptide fractions were pooled and lyophilized to give 30 mgs of white solid of >98% purity, Compound 3.

Compound 3

AVSEHOLLHDKGKSIODLRRRELLEKLLEKLHTX-NH$_2$ (X=hSer, SEQ ID NO:8)

Ala Val Ser Glu His Gln Leu Leu His Asp Lys Gly Lys Ser Ile
1           5                   10              15

Gln Asp Leu Arg Arg Arg Glu Leu Leu Glu Lys Leu Leu Glu Lys
            20                  25              30

Leu His Thr hSer NH$_2$ (SEQ ID NO:8).

Physical Data:

m.p. 138°–142° C. $[\alpha]_D^{25}$ –45.970 (c 0.25, H$_2$O)

FAB ($C_{176}H_{302}N_{56}O_{52}$): [M+H] +4033.9

AAA: Asp, 2.1(2); Glu, 6.1(6); Ser, 1.6(2); His, 2.8(3); Gly, 0.97(1); hSer, 0.97(1); Thi, 1.0(1); Ala, 1.0(1); Arg, 2.9(3); Val, 1.0(1); Ile, 1.0(1); Leu, 7.6(8); Lys, 3.9(4).

Similarly, Compounds 22, 23 and 28 were prepared following this procedure.

Compound 22

AVSEIOFLHN LGKHLSSLRR RELLEKLLEK LHNX-NH$_2$ (SEQ ID NO:36) (X=homoserine)

Ala Val Ser Glu Ile Gln Phe Leu His Asn Leu Gly Lys His Leu
1           5                   10              15

Ser Ser Leu Arg Arg Arg Glu Leu Leu Glu Lys Leu Leu Glu Lys
            20                  25              30

Leu His Asn hSer NH$_2$ (SEQ ID NO:36)

Physical Data: m.p. 69.4°–128° C. $[\alpha]_D^{25}$ –43.93 (c 0.15, H$_2$O)

FAB ($C_{179}H_{302}N_{56}O_{49}$): [M+H]$^+$4022.9

AAA: Asx, 2.0(2); Glx, 4.9(5); Ser, 2.6(3); His, 2.8(3); Gly, 1.0(1); Ala, 1.0(1); Arg, 3.0(3); Val, 1.0(1); Phe, 1.0(1); Ile, 0.9(1); Leu, 8.8(9); Lys, 3.4(3);

Compound 23

AVSEIOFLHN KGKHLSSLRR RELLEKLLEK LHNX-NH$_2$ (SEQ ID NO:37) (X=homoserine)

Ala Val Ser Glu Ile Gln Phe Leu His Asn Leu Gly Lys His Leu
1           5                   10              15

Ser Ser Leu Arg Arg Arg Glu Leu Leu Glu Lys Leu Leu Glu Lys
            20                  25              30

Leu His Asn hSer NH$_2$ (SEQ ID NO:37)

Physical Data: m.p. 87.1°–142.1° C. $[\alpha]_D$ –52.14 (c 0.41, H$_2$O)

FAB ($C_{179}H_{303}N_{57}O_{49}$): [M+H]$^+$4038

AAA: Asx, 2.1(2); Glx, 4.9(5); Ser, 2.7(3); His, 2.8(3); Gly, 1.0(1); hser, 1.0(1); Ala, 1.0(1); Arg, 3.0(3); Val, 1.1(1); Phe, 0.9(1); Ile, 0.9(1); Leu, 7.9(8); Lys, 3.7(4).

Compound 28

AVSEHOLLHD KGKSIODLRR RELLERLLER LHTAGRRX-NH₂ (SEQ ID NO:42) (X=homoserine)

Ala Val Ser Glu His Gln Leu Leu His Asp Lys Gly Lys Ser Ile
1         5                   10              15

Gln Asp Leu Arg Arg Arg Glu Leu Leu Glu Arg Leu Leu Glu Arg
              20                  25                  30

Leu His Thr Ala Gly Arg Arg hSer NH₂ (SEQ ID NO:42)
            35

Physical Data: m.p. 80° C. $[\alpha]_D^{25}$ −48.64 (c 0.09, H₂O)
FAB (C₁₉₃H₃₃₄N₇₀O₅₆): [M+H]⁺4530.0
AAA: Asx, 2.2(2); Glx, 6.1(6); Ser, 1.7(2); His, 3.0(3); Gly, 1.9(2); hSer, 1.0(1); Thr, 1.0(1); Ala, 2.1(2); Arg, 7.2(7); Val, 0.8(1); Ile, 1.0(1); Leu, 8.4(8); Lys, 2.1(2).

The homoserine alkylamides were similarly prepared from the homoserine lactone by dissolving it in DMF containing an excess of the corresponding alkylamine. After stirring at room temperature for several days (the reaction was monitored by analytical HPLC) the mixture was evaporated to dryness and the peptide purified by preparative HPLC. Representative homoserine alkylamides are Compounds 55 and 56.

Compound 55

AVSEHOLLHD KGKSIODLRR RELLEKLLEK LHTX-NHCH₂CH₃ (SEQ ID NO:69) (X=homoserine)

Ala Val Ser Glu His Gln Leu Leu His Asp Lys Gly Lys Ser Ile
1         5                   10              15

Gln Asp Leu Arg Arg Arg Glu Leu Leu Glu Lys Leu Leu Glu Lys
              20                  25                  30

Leu His Thr hSer NHCH₂CH₃ (SEQ ID NO:69)

Physical Data: m.p. (not determined) $[\alpha]_D^{25}$ (not determined)
FAB(C₁₇₈H₃₀₆N₅₆O₅₂): [M+H]⁺4063.0
AAA: Asx, 2.1(2); Glx, 5.8(6); Ser, 1.7(2); His, 3.1(3); Gly, 0.9(1); Thr, 1.0(1); Ala, 0.9(1); Arg, 3.0(3); Val, 1.1(1); Ile, 1.0(1); Leu, 8.4(8); Lys, 3.7(4); hSer, 0.9(1).

Compound 56

AVSEHOLLHD KGKSIODLRR RELLEKLLEK LHTX-NHCH₂CH₂C₆H₅ (SEQ ID NO:70) (X=homoserine)

Ala Val Ser Glu His Gln Leu Leu His Asp Lys Gly Lys Ser Ile
1         5                   10              15

Gln Asp Leu Arg Arg Arg Glu Leu Leu Glu Lys Leu Leu Glu Lys
              20                  25                  30

Leu His Thr hSer NHCH₂CH₂C₆H₅ (SEQ ID NO:70)

Physical Data: m.p. (not determined) $[\alpha]_D^{25}$ (not determined)
FAB(C₁₈₄H₃₁₀N₅₆O₅₂): [M+H]⁺4138.8
AAA: Asx, 2.0(2); Glx, 5.9(6); Ser, 1.7(2); His, 2.9(3); Gly, 0.9(1); Thr, 1.0(1); Ala, 0.9(1); Arg, 3.0(3); Val, 1.0(1); Ile, 0.9(1); Leu, 8.0(8); Lys, 4.1(4); hSer, 0.9(1).

EXAMPLE IV

The cesium salt of N$^\alpha$-Boc-N$^\gamma$-Fmoc-L-2,4-diaminobutyric acid was attached to Merrifield resin (DMF, 50° C., 48 hrs) and used in a solid-phase synthesis in place of the Boc-Ala resin as in Example I. Upon completion of the synthesis the peptide was treated with 20% piperidine in DMF at room temperature for 30 minutes to remove the side chain Fmoc protecting group. The protected peptide spontaneously cyclized to the lactam thereby cleaving itself from the resin. The solution was filtered from the resin and evaporated under vacuum to leave on oil. The residue was treated with liquid HF as in Example I to yield the crude unprotected peptide. The peptide was treated and purified as in Example I.

Compound 49

AVSEHOLLHD KGKSIODLRR RELLEKLLEK LHTX (SEQ ID NO:63) (X=L-2,4-diaminobutyryl lactam)

Ala Val Ser Glu His Gln Leu Leu His Asp Lys Gly Lys Ser Ile
1         5                   10              15

Gln Asp Leu Arg Arg Arg Glu Leu Leu Glu Lys Leu Leu Glu Lys
              20                  25                  30

Leu His Thr L-2,4-diaminobutyryl lactam (SEQ ID NO:63)

Physical Data: m.p. 161°–181° C. $[\alpha]_D^{25}$ −48.38 (c 0.2), H₂O)
FAB (C₁₇₆H₃₀₀N₅₆O₅₁) [M+H]⁺4016.8
AAA: Asx, 2.1 (2); Glx, 6.3 (6); Ser, 1.7 (2) ; His, 3.3 (3); Gly, 1.1(1); Thr, 1.0(1); Ala, 2.1(2); Arg, 2.9(3); Val, 0.9(1); Ile, 0.9(1); Leu, 8.0(8); Lys, 3.8(4).

EXAMPLE V

An aqueous solution of the homoserine lactone analog from Example II was treated with porcine liver esterase (Sigma Chemical Company, St. Louis, Mo.). The hydrolysis of the lactone to the C-terminal homoserine was monitroed by analytical HPLC. When the hydrolysis was judged to be complete the material was pruified by preparative HPLC as in Example I.

Compound 37

AVSEHOLLHD KGKSIODLRR RELLEKLLEK LHTX-OH (SEQ ID NO:51) (X=homoserine)

Ala Val Ser Glu His Gln Leu Leu His Asp Lys Gly Lys Ser Ile
1         5                   10              15

Gln Asp Leu Arg Arg Arg Glu Leu Leu Glu Lys Leu Leu Glu Lys
              20                  25                  30

Leu His Thr hSer OH (SEQ ID NO:51)

Physical Data: m.p. (not determined) $[\alpha]_D^{25}$ (not determined)
FAB (C₁₇₆H₃₀₁N₅₅O₅₃): [M+H]⁺4035.1
AAA: Asx, 2.1(2); Glx, 5.9(6); Ser, 2.0(2); His, 3.1(3); Gly, 0.8(1); hSer, 0.8(1); Thr, 1.0(1); Ala, 1.0(1); Arg, 3.0(3); Val, 1.3(1); Ile, 1.0(1); Leu, 8.1(8); Lys, 3.8(4).

EXAMPLE VI

Following Example I, the protected peptide-resin BocAVS(Bzl)E(OBz)H(Bom)QLLHD(OBzl)R(Ts)GR(Ts)S (Bzl)IQD(OBz)LR(Ts)R(Ts)E(OBz) LLE(OBzl)R(Ts)LLK (Fmoc)R(Ts)LH(Bom)T(Bzl))A-O-PAM was synthesized on a 0.35 mmol scale. All N$^\alpha$ groups were protected with t-butoxycarbonyl (Boc); side chain protecting groups were as indicated. After completion of the synthesis, the peptide resin was treated with 50 mL of 20% piperidine in dimethylformamide (DMF) at room temperature for 30 minutes to remove the fluorenylmethoxycarbonyl (Fmoc) protecting group on lysine. The resin was washed successively with DMF, MeOH, $CH_2Cl_2$ and dried to give 1.6 g partially protected peptide. 0.8 g (0.175 mmol) of the partially protected peptide was acylated on lysine with 0.44 g (0.3 mmol) of methoxydi(ethyleneoxy) acetic acid [PEG(2) $CH_2COOH$] in the presence of 0.16 g (0.3 mmol) benzotriazolyloxy-tris(pyrrolidino)phosphonium hexafluorophosphate (PyBop) and 0.067 g (0.525 mmol) of diisopropylethyl amine (DIEA) in 20 mL DMF at room temperature for 5 hrs. After 5 hrs., the resin was filtered and washed successively with DMF, MeOH and $CH_2Cl_2$. The acylation step was repeated twice until negative ninhydrin result on the resin was obtained. The final peptide was cleaved from the resin with removal of the side chain protecting groups and purification as in Example I; 100 mgs of Compound 19 were obtained.

Compound 19

AVSEHOLLHDRGRSIODLRRRELLERLLKRLHTA-OH (SEO ID NO:18) $CH_3O$ $(CH_2CH_2O)_2CH_2C=O$

Ala Val Ser Glu His Gln Leu Leu His Asp Arg Gly Arg Ser Ile
1             5                  10                15
Gln Asp Leu Arg Arg Arg Glu Leu Leu Glu Arg Leu Leu
                        20                  25
Lys (COCH₂PEG2) Arg Leu His Thr Ala OH (SEQ ID NO:18)
30

Physical Data: m.p. 145°–195° C. $[\alpha]_D^{25}$–44.600 (c 0.2, $H_2O$)

FAB ($C_{193}H_{316}N_{64}O_{54}$): [M+H]⁺4276.2

AAA: Asp, 2.1(2); Glu, 5.0(5); Ser, 1.6(2); His, 2.9(3); Gly, 0.9(1); Thr, 1.9(2); Arg, 7.1(7); Val, 1.1(1); Ile, 1.0(1); Leu, 8.0(8); Lys, 0.9(1).

EXAMPLE VII

Peptide was synthesized, cleaved and purified in the same manner as in Example IV except 2-methoxypoly (ethyleneoxy) acetic acid [PEG(5000)$CH_2CO_2H$] was used as the acylating agent. 0.8 g (0.175 mmol) of partially protected peptide yielded 300 mgs of pure Compound 20.

Compound 20

AVSEHOLLHDRGRSIODLRRRELLERLLKRLHTA-OH (SEO ID NO:19) $CH_3O(CH_2CH_2O)_{110}CH_2C=O$

Ala Val Ser Glu His Gln Leu Leu His Asp Arg Gly Arg Ser Ile
1             5                  10                15
Gln Asp Leu Arg Arg Arg Glu Leu Leu Glu Arg Leu Leu
                        20                  25
Lys (COCH₂PEG5000) Arg Leu His Thr Ala OH (SEQ ID NO:19).
30

Physical Data: m.p. 105° C $[\alpha]_D^{25}$–22.950 (c 0.11, 50% aq. HOAC)

AAA: Asp, 2.0(2); Glu, 4.8(5); Ser, 1.6(2); His, 2.6(3); Gly, 1.1(1); Thr, 1.1(1); Arg, 7.3(7); Val, 0.8(1); Ile, 0.9(1); Leu, 8.3(8); Lys, 1.1(1); Ala, 1.8(2).

EXAMPLE VIII

Synthesis of hPTHrp(1–34) analog gene

A synthetic gene coding for the hPTHrp(1–34) analog Compound 4 (SEQ ID NO:9) was designed having the nucleotide sequence and enzyme restriction sites shown in FIG. 1. The requisite oligodeoxynucleotides were prepared with a DNA synthesizer (Milligen/Biosearch) using the phosphoramidite process of Sinha, et al., *Nucleic Acid Research* 12, 4539–4557 (1984). After deprotection, the crude oligonucleotides were purified by gel electrophoresis on preparative 15% polyacrylamide gels. The oligonucleotides were located with UV, excised from the gel, desalted over Waters c18 Sep-pak® cartridges, and lyophilized.

Amplification via polymerase chain reaction (PCR) was carried out on a Perkin-Elmer Cetus thermal cycler, with 25 cycles of: 94° C. for 1 minute, 50° C. for 2 minutes, and 72° C. for 3 minutes, using reagents, including Taq polymerase, from the "GeneAmp" DNA amplification kit (Perkin-Elmer Cetus).

Two overlapping oligonucleotides, an 88mer (2 µg), PTH3, (SEQ ID NO:31):

CCTCTAGATC TCCGCGGCGC TAGC ATG GCT GTT TCT GAA CAT CAG 45
                              Met Ala Val Ser Glu
His Gln
                                          1             5
CTG CTT CAT GAC AAA GGT AAA TCG ATT CAA GAT CTG AGA CGT C 88
Leu Leu His Asp Lys Gly Lys Ser Ile Gln Asp Leu Arg Arg
         10                  15                  20 and an anti-sense 90mer (2 µg), PTH4 (SEQ ID NO:32):

CCTCGAAGCT TATGCATCAT TATCTAGA CAT AGT ATG CAG CTT TTC 46
                                Met Thr His Leu Lys Glu
                                                   30
AAG CAG TTT CTC CAG CAG CTC GCG ACG TCT CAG ATC TTG AAT 88
Leu Leu Lys Glu Leu Leu Glu Arg Arg Arg Leu Asp Gln Ile
            25              20              15
CG 90, were prepared as the template DNA sequence for the hPTHrp (1–34) analog gene. Utilizing the two flanking primers, PTHPCR1: CCTCTAGATC TCCGCGGCGC TAG (SEQ ID NO:33) and PTHPCR2: CCTCGAAGCT TATGCATCAT TATC (SEQ ID NO:34), the entire gene was amplified by PCR. The amplified DNA products were purified by gel electrophoresis on 4% NuSieve® agarose gel. The band containing the synthetic hPTHrp(1–4) analog gene, approximately 150 bases in length, was excised from the gel and approximately 200 ng of DNA isolated by Elu-Quik® glass gel DNA extraction (Schleicher & Schuell, Keene, N.H.).

EXAMPLE IX

Molecular Cloning of an hPTHrp(1–34)1 Analog Gene

Figure 2:
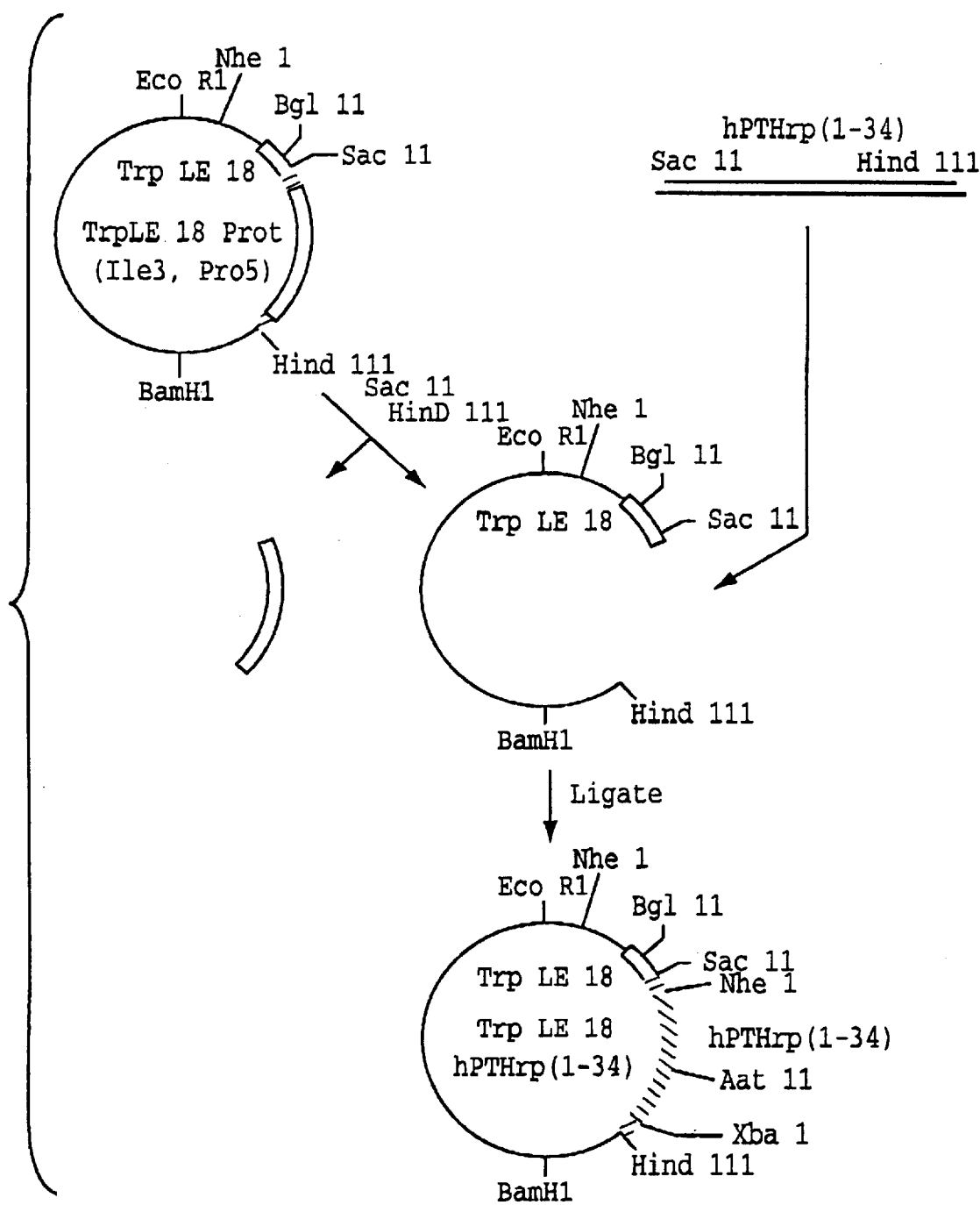
FIG. 2 outlines the preparation of a plasmid incorporating a PTHrp(1–34) analog gene.

To subclone the hPTHrp(1–34) analog gene of Example VI, 200 ng of the amplified DNA was isolated and cut by restriction enzymes HinD III and Sac II. As shown in FIG. 2, the DNA was ligated to 2 µg TrpLE 18 Prot (Ile$^3$,Pro$^5$) plasmid previously cleaved with Hind III and Sac II.

The resulting plasmid, TrpLE 18 hPTHrp(1–34)1, containing one copy of the hPTHrp(1–34) analog gene was then transformed into competent E. coli HB 101 cells (CLONTECH, Palo Alto, Calif.). Transformants were subjected to PCR analysis to verify insertion. Transformed cell colonies were selected and boiled in 200 µL of water for 5 minutes; 2 µL were subjected to PCR with two primers flanking the insert. The PCR product was then analyzed on 1% agarose gel to confirm the presence of one copy of the hPTHrp(1–34) gene insert. TrpLE 18 hPTHrp(1–34)1 construct was then verified by DNA sequencing on an automated DNA sequencer (Applied Biosystems Model 373A, Foster City, Calif.) using the vendor's Dye Deoxy Terminator Sequencing kit.

EXAMPLE X

Construction of a Trp LE 18 vector containing multiple copies of the hPTHrp(1–34) analog gene Unique Nhe I and Xba I restriction sites are located near the beginning and end of the hPTHrp(1–34) analog gene sequence. These two sites, which recognize different sequences, but produce identical single strand cohesive termini, allow the construction of multiple copy hPTHrp (1–34) genes within the Trp LE 18 vector.

Figure 3:
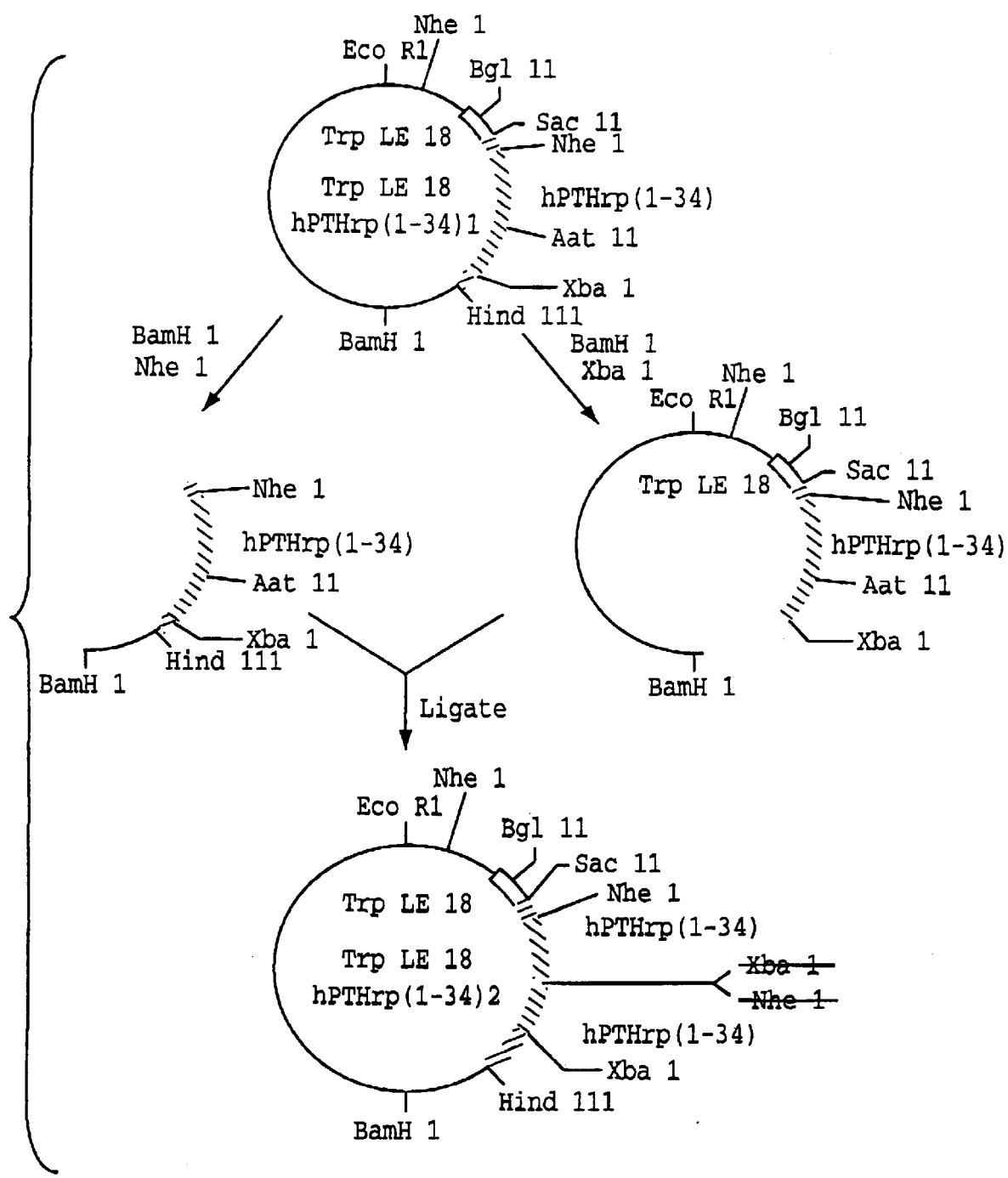
FIG. 3 outlines the preparation of a plasmid incorporating two copies of a PTHrp(1–34) analog gene.

The strategy for constructing repeated hPTHrp(1–34) sequences in tandem is outlined in FIG. 3. In separate reactions, 5 µg of plasmid Trp LE 18 hPTHrp(1–34)1 containing a single copy of the gene was cleaved with Bam HI +Nhe I and Xba I+Bam HI. From each digest, about 300 ng of the fragment containing the hPTHrp(1–34) analog gene was isolated. These two fragments were mixed and ligated to form the Trp LE 18 hPTHrp(1–34)2 plasmid. This plasmid was used to transform competent E. coli HB 101 cells. Sizing of the transformed PCR products on 1% agarose gel was used to determine the presence of two copies of the hPTHrp(1–34) gene insert. TrpLE 18 hPTHrp(1–34)2 containing two copies of the gene was then confirmed by DNA sequencing. The correct fusion of the two hPTHrp (1–34) genes results in the elimination of Nhe I and Xba I sites at the junction. This makes the remaining Xba I and Nhe I sites flanking the tandem genes unique.

Figure 4:
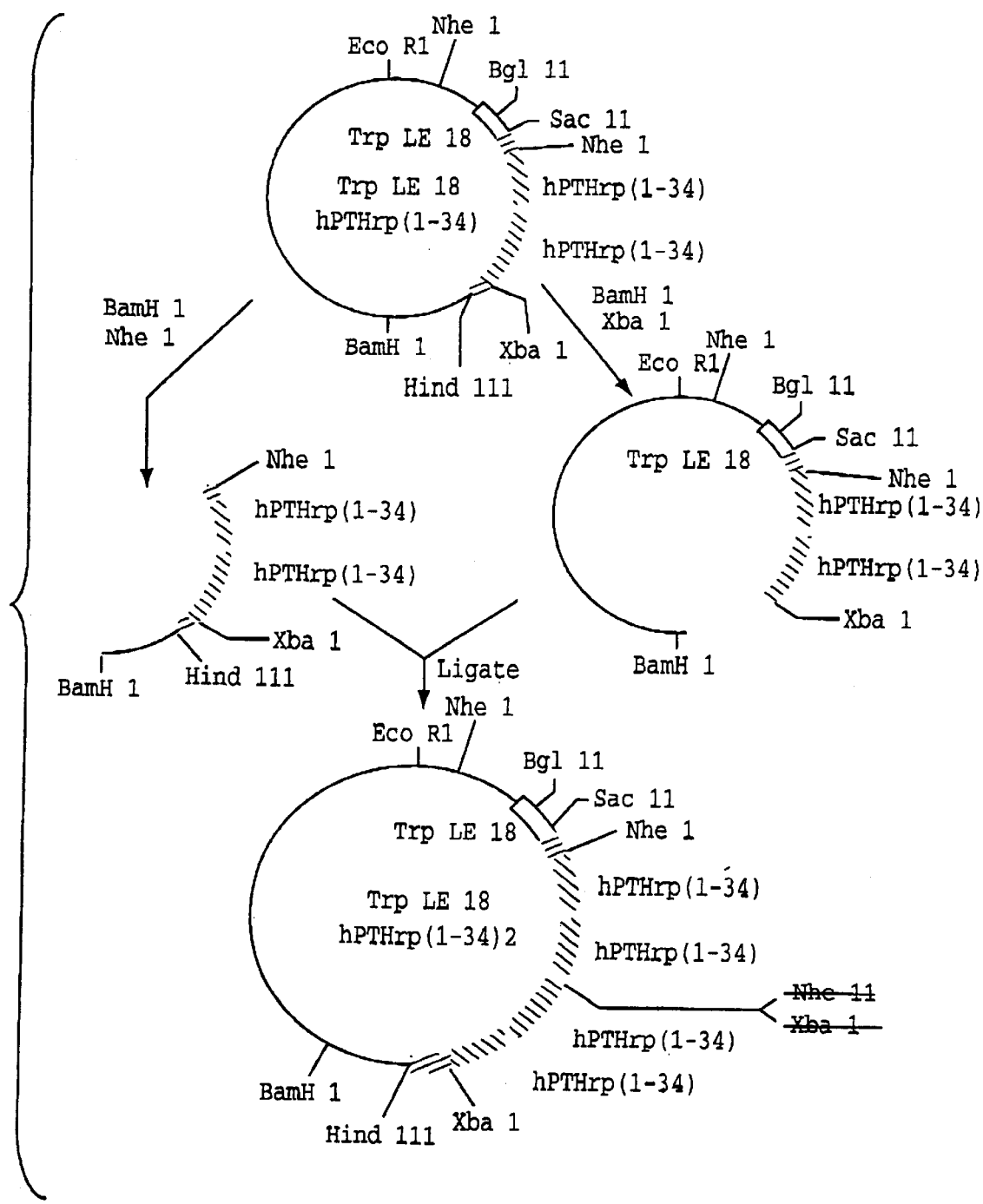
FIG. 4 outlines the preparation of a plasmid incorporating four copies of a PTHrp(1–34) analog gene.

By repeating this process the final plasmid Trp LE 18 hPTHrp(1–34)4 containing four copies of the hPTHrp(1–34) gene was constructed, as shown in FIG. 4. The sequence of Trp LE 18 hPTHrp(1–34)4 was found to be correct by DNA sequence analysis.

EXAMPLE XI

Expression and Purification of Trp LE 18 hPTHrp (1–34)4

Induction of the Trp LE 18 hPTHrp(1–34)4.

A starter culture of 50 mL of LB culture media, J. H. Miller, "Experiments in Molecular Genetics," p.431 (1972), incorporated herein by reference, containing 50 µg/mL ampicillin and 100 µg/mL tryptophan, was inoculated with E. coli cells containing Trp LE 18 hPTHrp(1–34)4 plasmid, and grown overnight at 37° C. with vigorous shaking to an $A_{550}$ of about 6. Two liters of LB culture media for production were pre-warmed to 37° C. and seeded with 20 mL of the starter culture to give an $A_{550}$ of about 0.06. The culture was then grown with vigorous shaking to an $A_{550}$ of between 0.6 and 0.8, whereupon 2 mL of a 10 mg/mL solution of indole acrylic acid (IAA) was added. Growth was continued with good aeration for about 16 hr to a final $A_{550}$ of about 6 (typically, between 4 and 10). The cells were concentrated by centrifugation and resuspended in 500 mL of 50 mM Tris-HCl, pH 7.5, 0.1 mM EDTA buffer solution (Tris buffer).

The suspension was sonicated using a Heat Systems-Ultrasonics, Inc. model 220F sonicator (equipped with a ¾" horn) operated at 50% of full capacity to avoid overheating.

To determine the extent of induction, the whole cells were analyzed by SDS-PAGE. The gene products derived from the TrpLE 18 hPTHrp(1–34)4 construct were seen as a major band of the predicted MW of approximately 17,000. This accounts for as much as 10% of the total cellular protein.

Isolation of the Fusion Protein.

The cell lysate was centrifuged for 15 min. at about 3600 x g to pellet the Trp LE 18 hPTHrp(1–34)4 fusion protein; the supernatant was discarded. The pellet was resuspended in 200 mL Tris buffer. (typically 40–80 $A_{550}$/mL).

EXAMPLE XII

Processing of the Fusion Protein and Purification of homo-Serlactone hPTHrp(1–34) peptide Cleavage of the methionine residues flanking the hPTHrp (1–34) multimeric fusion protein with CNBr releases the desired homo-Serlactone hPTHrp(1–34) polypeptide, which was purified as described below.

CNBr Treatment of Fusion Protein.

The washed pellet of TrpLE 18 hPTHrp(1–34)4 fusion protein was resuspended by gently stirring in 60 mL of 70%, formic acid (about 20 mg/mL total protein; typically material from 1000 $A_{550}$ units of cells is dissolved in 3 mL). A few drops of octanol were added and $N_2$ bubbled through the solution for 20 minutes before adding 5.5 g CNBr. This reaction was allowed to proceed for 6 hours at 25° C. before an equal volume of 50:50 MeOH:$H_2O$ was mixed with the sample and subsequently removed by rotary evaporation. After 2 to 4 repetitions of this process, the bulk of the formic acid and CNBr were essentially removed. The sample was then evaporated to dryness, redissolved in 200 mL water and lyophilized for storage.

Purification of homo-Serlactone hPTHrp(1–34)

The CNBr cleaved supernatant was dialyzed against 50 mM $KH_2PO_4$ pH 6.5 for 24 hours with multiple changes. During dialysis, pH was maintained at 6.5. After dialysis, the precipitates were removed by high speed centrifugation. The supernatant was clarified through a Gelman 0.45$\mu$ filter device (Acrodisc 4184).

Cation Exchange Chromatography

Initial purification was accomplished by cation exchange chromatography on a Bio-Gel TSK-SP-5PW HPLC column (21.5×150 mm). Chromatographic conditions for a flow rate of 8 mL/min and a yield of approximately 12 mg of highly purified homo-Serlactone hPTHrp(1–34) peptide were:

1. Column equilibration in 50 nM $KH_2PO_4$, pH 6.5
2. Load 10 mL clarified supernatant (approximately 1.5 L culture broth or 2.4 g inclusion).
3. Wash column with 50 mM $KH_2PO_4$ pH 6.5 containing 50 nM NaCl until baseline is stabilized.
4. Elute column with 50 nM $KH2PO_4$ pH 6.5 containing 90 mM NaCl. Collect fractions for about 45 minutes.
5. Analyze the 90 mM NaCl fractions for homo-Serlactone hPTHrp(1–34) content by C18 HPLC before pooling and storage.

Reverse Phase HPLC Chromatography

A reverse phase Poros R/H 4.6×100 mm column (Perseptive Biosystems, Cambridge, Mass.) was used for the final purification step. The chromatographic conditions were as follows:

Mobile phase A: 0.1% trifluoroacetic acid (TFA)/water B: 0.1% trifluoroacetic acid (TFA)/$CH_3CN$

| TIME | FLOW | % B |
| --- | --- | --- |
| 0 min | 4 ml/min | 15 |
| 5.0 min | 4 ml/min | 40 |
| 5.2 min | 4 ml/min | 100 |
| 6.8 min | 4 ml/min | 100 |
| 7.0 min | 4 ml/min | 15 |

Retention time of the homo-Serlactone hPTHrp(1–34), Compound 4, was approximately 2.943 minutes. The purified peptide was approximately 98% pure as determined by mass spectroscopy.

EXAMPLE XIII

The compounds of this invention were evaluated for their effect on bone mass in ovariectomized rats, generally in accord with the procedures of Gunness-Hey and Hock, *Metab. Bone Dis.* 5:177 181 (1984).

Adult Sprague-Dawley female rats were acclimatized, weight grouped (n=9, 10 or 12), and subjected to bilateral ovariectomy (OVX) or sham surgery. Dosing was initiated 17 days after surgery and continued for 20 days. Test compound was administered subcutaneously once a day in 2% rat serum/saline vehicle.

After 20 days of dosing, the rats were sacrificed and the right femurs excised. The femurs were cut in half and the distal half femurs (DHF) were further separated into trabecular bone (TB) and cortical bone (CB) by drilling out the trabeculae. Calcium was extracted and measured by Calcette calcium analyzer and expressed as mean bone Ca in mg/DHF/100 g body weight.

The two sample t-test was used to compare OVX and sham groups. One-way ANOVA was used to compare OVX groups, followed by Fisher's LSD multiple comparison to compare each treatment group to vehicle.

Ovariectomy induced substantial total bone loss, primarily from trabecular bone. Total bone calcium was 47 to 54% lower than for sham-operated controls. bPTH(1–34) and hPTHrp(1–34) at 80 $\mu$g/kg/day provided statistically significant increases in total bone calcium for treated OVX rats, ranging from 53 to 95% and 18 to 40%, respectively; however, there was no significant increase in cortical bone calcium.

Compounds of this invention, dosed at 80 $\mu$g/kg/day, increased total bone calcium by from 66 to 138% and trabecular calcium by from 87 to 128%. Cortical bone calcium, trabecular thickness, and bone volume were also significantly increased over untreated OVX controls.

In this assay, the following compounds were tested:

| Compound Number | n (# of tests) | Trabecular Bone Calcium (% increase over OVX) | Total Bone Calcium (% increase over OVX) |
| --- | --- | --- | --- |
| Compound 1 (SEQ ID NO: 7) | 6 | 101–128% | 88–138% |
| Compound 2 (SEQ ID NO: 6) | 3 | 87–102% | 66–114% |
| Compound 4 (SEQ ID NO: 9) | 3 | — | 88–114% |

In similar studies, ovariectomized rats were dosed for 5, 10 and 20 days, at 40 ug/kg/day, with the following results:

| Compound Number | n (# of tests) | # of Days (d) of dosing | Total Bone Calcium (% increase over OVX) |
| --- | --- | --- | --- |
| Compound 1 (SEQ ID NO: 7) | 3 | 20 d | 73–109% |
| Compound 4 (SEQ ID NO: 9) | 5 | 20 d | 79–105% |
| Compound 4 (SEQ ID NO: 9) | 1 | 10 d | 79% |
| Compound 49 (SEQ ID NO: 63) | 1 | 10 d | 93% |
| Compound 4 (SEQ ID NO: 9) | 1 | 5 d | 55% |
| Compound 42 (SEQ ID NO: 56) | 1 | 5 d | 60% |

EXAMPLE XIV

Mature New Zealand White female rabbits (Hazelton Research Products, Inc., 3.6 kg, n=9–11/treatment group) were injected daily with vehicle or 0.15 mg/kg of prednisone for 13 months. Bone mineral density (BMD) was measured by dual energy x-ray absorptiometry (Hologic Model QDR-1500W, Hologic, Inc., Waltham, Mass.) and biochemical markers of bone metabolism were followed. After 9 months, subgroups received in addition 0.05, 0.15 or 0.5 ug/kg/day sc of Compound 1 (Seq. ID No. 7). Two months later the doses were raised to 0.5, 3 and 10 ug/kg/day. Prednisone treatment resulted in rapid initial loss (2–4 months) followed by stable BMD for the remainder of the study. Final losses in BMD from baseline of 12.4±1.3%, 18.1±1.9%, and 11.8±2.5% were observed in the lumbar spine A/P view, lateral view, and distal femur. Less decrease (7.8±2.2%) was observed in the femoral diaphysis. The lower, early doses did not change these figures. After 30–60 days 10 ug/kg of Compound 1 in animals continuing on prednisone restored BMD at all sites to values not significantly different from those seen in control rabbits treated with the vehicle alone for the 12 months. Serum osteocalcin fell 6.4 fold from a baseline of 50±8 ng/ml in prednisone treated rabbits, but was returned to normal by concomitant 10 ug/kg of Compound 1.

I claim:

1. A method for treating corticosteroid induced osteopenia, which method comprises administering to a subject in need thereof an effective amount of a modified PTH or PTHrP having bone mass restoring activity which differs from naturally occurring PTH or PTHrP by changes comprising substitutions at one or more of positions (22–31), wherein the substitutions are selected from the group consisting of SEQ ID Nos. (26, 27, 28, 29, 30, 85 and 86).

2. A method of claim 1 in which the effective amount of polypeptide is from about 0.002 μg of polypeptide/kg of patient body mass/day to about 10 μg of polypeptide/kg of patient body mass/day.

3. A method for treating corticosteroid induced osteopenia, which method comprises administering to a subject in need thereof an effective amount of a modified parathyroid hormone (PTH) or parathyroid hormone related peptide (PTHrP) having bone mass restoring activity which differs from naturally occurring PTH or PTHrP by changes comprising substitutions at one or more of positions (22–31), wherein the substitution consists of SEQ ID No. 26.

4. A method for treating corticosteroid induced osteopenia, which method comprises administering to a subject in need thereof an effective amount of a modified PTH or PTHrP having bone mass restoring activity which differs from naturally occurring PTH or PTHrP by changes comprising substitutions at one or more of positions (22–31), wherein the substitution consists of SEQ ID No. 27.

5. A method for treating corticosteroid induced osteopenia, which method comprises administering to a subject in need thereof an effective amount of a modified PTH or PTHrP having bone mass restoring activity which differs from naturally occurring PTH or PTHrP by changes comprising substitutions at one or more of positions (22–31), wherein the substitution consists of SEQ ID No. 28.

6. A method for treating corticosteroid induced osteopenia, which method comprises administering to a subject in need thereof an effective amount of a modified PTH or PTHrP having bone mass restoring activity which differs from naturally occurring PTH or PTHrP by changes comprising substitutions at one or more of positions (22–31), wherein the substitution consists of SEQ ID No. 29.

7. A method for treating corticosteroid induced osteopenia, which method comprises administering to a subject in need thereof an effective amount of a modified PTH or PTHrP having bone mass restoring activity which differs from naturally occurring PTH or PTHrP by changes comprising substitutions at one or more of positions (22–31), wherein the substitution consists of SEQ ID No. 30.

8. A method for treating corticosteroid induced osteopenia, which method comprises administering to a subject in need thereof an effective amount of a modified PTH or PTHrP having bone mass restoring activity which differs from naturally occurring PTH or PTHrP by changes comprising substitutions at one or more of positions (22–31), wherein the substitution consists of SEQ ID No. 85.

9. A method for treating corticosteroid induced osteopenia, which method comprises administering to a subject in need thereof an effective amount of a modified PTH or PTHrP having bone mass restoring activity which differs from naturally occurring PTH or PTHrP by changes comprising substitutions at one or more of positions (22–31), wherein the substitution consists of SEQ ID No. 86.

* * * * *

SEQUENCE LISTING ( 1 ) GENERAL INFORMATION:

( i i i ) NUMBER OF SEQUENCES: 86

( 2 ) INFORMATION FOR SEQ ID NO:1:

( i ) SEQUENCE CHARACTERISTICS:
        ( A ) LENGTH: 34 amino acids
        ( B ) TYPE: amino acid
        ( D ) TOPOLOGY: linear ( i i ) MOLECULE TYPE: peptide ( i i i ) HYPOTHETICAL: NO ( v ) FRAGMENT TYPE: N-terminal ( x i ) SEQUENCE DESCRIPTION: SEQ ID NO:1:

```
Ser  Val  Ser  Glu  Ile  Gln  Leu  Met  His  Asn  Leu  Gly  Lys  His  Leu  Asn
 1              5                        10                       15
Ser  Met  Glu  Arg  Val  Glu  Trp  Leu  Arg  Lys  Lys  Leu  Gln  Asp  Val  His
               20                        25                       30
Asn  Phe
```

( 2 ) INFORMATION FOR SEQ ID NO:2:

( i ) SEQUENCE CHARACTERISTICS:
        ( A ) LENGTH: 34 amino acids
        ( B ) TYPE: amino acid
        ( D ) TOPOLOGY: linear ( i i ) MOLECULE TYPE: peptide ( i i i ) HYPOTHETICAL: NO ( v ) FRAGMENT TYPE: N-terminal ( x i ) SEQUENCE DESCRIPTION: SEQ ID NO:2:

```
Ala  Val  Ser  Glu  Ile  Gln  Phe  Met  His  Asn  Leu  Gly  Lys  His  Leu  Ser
 1              5                        10                       15
Ser  Met  Glu  Arg  Val  Glu  Trp  Leu  Arg  Lys  Lys  Leu  Gln  Asp  Val  His
               20                        25                       30
Asn  Phe
```

( 2 ) INFORMATION FOR SEQ ID NO:3:

( i ) SEQUENCE CHARACTERISTICS:
        ( A ) LENGTH: 34 amino acids
        ( B ) TYPE: amino acid
        ( D ) TOPOLOGY: linear ( i i ) MOLECULE TYPE: peptide ( i i i ) HYPOTHETICAL: NO ( v ) FRAGMENT TYPE: N-terminal ( x i ) SEQUENCE DESCRIPTION: SEQ ID NO:3:

```
         Ser  Val  Ser  Glu  Ile  Gln  Leu  Met  His  Asn  Leu  Gly  Lys  His  Leu  Ser
         1              5                        10                       15

Ser  Leu  Glu  Arg  Val  Glu  Trp  Leu  Arg  Lys  Lys  Leu  Gln  Asp  Val  His
                        20                       25                       30

Asn  Phe
```

( 2 ) INFORMATION FOR SEQ ID NO:4:

( i ) SEQUENCE CHARACTERISTICS:
        ( A ) LENGTH: 34 amino acids
        ( B ) TYPE: amino acid
        ( D ) TOPOLOGY: linear ( i i ) MOLECULE TYPE: peptide ( i i i ) HYPOTHETICAL: NO ( v ) FRAGMENT TYPE: N-terminal ( x i ) SEQUENCE DESCRIPTION: SEQ ID NO:4:

```
         Ala  Val  Ser  Glu  His  Gln  Leu  Leu  His  Asp  Lys  Gly  Lys  Ser  Ile  Gln
         1              5                        10                       15

Asp  Leu  Arg  Arg  Arg  Phe  Phe  Leu  His  His  Leu  Ile  Ala  Glu  Ile  His
                        20                       25                       30

Thr  Ala
```

( 2 ) INFORMATION FOR SEQ ID NO:5:

( i ) SEQUENCE CHARACTERISTICS:
        ( A ) LENGTH: 34 amino acids
        ( B ) TYPE: amino acid
        ( D ) TOPOLOGY: linear ( i i ) MOLECULE TYPE: peptide ( i i i ) HYPOTHETICAL: NO ( v ) FRAGMENT TYPE: N-terminal ( x i ) SEQUENCE DESCRIPTION: SEQ ID NO:5:

```
         Ala  Val  Ser  Glu  His  Gln  Leu  Leu  His  Asp  Lys  Gly  Lys  Ser  Ile  Gln
         1              5                        10                       15

Asp  Leu  Arg  Arg  Arg  Glu  Leu  Leu  Glu  Lys  Leu  Leu  Arg  Lys  Leu  His
                        20                       25                       30

Thr  Ala
```

( 2 ) INFORMATION FOR SEQ ID NO:6:

( i ) SEQUENCE CHARACTERISTICS:
        ( A ) LENGTH: 34 amino acids
        ( B ) TYPE: amino acid
        ( D ) TOPOLOGY: linear ( i i ) MOLECULE TYPE: peptide ( i i i ) HYPOTHETICAL: NO ( v ) FRAGMENT TYPE: N-terminal ( x i ) SEQUENCE DESCRIPTION: SEQ ID NO:6:

```
         Ala  Val  Ser  Glu  His  Gln  Leu  Leu  His  Asp  Lys  Gly  Lys  Ser  Ile  Gln
         1              5                        10                       15

Asp  Leu  Arg  Arg  Arg  Glu  Leu  Leu  Glu  Lys  Leu  Leu  Glu  Lys  Leu  His
                        20                       25                       30

Thr  Ala
```

( 2 ) INFORMATION FOR SEQ ID NO:7:

( i ) SEQUENCE CHARACTERISTICS:
        ( A ) LENGTH: 34 amino acids
        ( B ) TYPE: amino acid
        ( D ) TOPOLOGY: linear ( i i ) MOLECULE TYPE: peptide ( i i i ) HYPOTHETICAL: NO ( v ) FRAGMENT TYPE: N-terminal ( x i ) SEQUENCE DESCRIPTION: SEQ ID NO:7:

```
Ala Val Ser Glu His Gln Leu Leu His Asp Lys Gly Lys Ser Ile Gln
 1               5                  10                  15
Asp Leu Arg Arg Arg Glu Leu Leu Glu Lys Leu Leu Glu Lys Leu His
            20                  25                  30
Thr Ala
```

( 2 ) INFORMATION FOR SEQ ID NO:8:

( i ) SEQUENCE CHARACTERISTICS:
        ( A ) LENGTH: 34 amino acids
        ( B ) TYPE: amino acid
        ( D ) TOPOLOGY: linear ( i i ) MOLECULE TYPE: peptide ( i i i ) HYPOTHETICAL: NO ( v ) FRAGMENT TYPE: N-terminal ( i x ) FEATURE:
        ( A ) NAME/KEY: Modified-site
        ( B ) LOCATION: 34
        ( D ) OTHER INFORMATION: /note= "Xaa34 = homoserine"

( x i ) SEQUENCE DESCRIPTION: SEQ ID NO:8:

```
Ala Val Ser Glu His Gln Leu Leu His Asp Lys Gly Lys Ser Ile Gln
 1               5                  10                  15
Asp Leu Arg Arg Arg Glu Leu Leu Glu Lys Leu Leu Glu Lys Leu His
            20                  25                  30
Thr Xaa
```

( 2 ) INFORMATION FOR SEQ ID NO:9:

( i ) SEQUENCE CHARACTERISTICS:
        ( A ) LENGTH: 34 amino acids
        ( B ) TYPE: amino acid
        ( D ) TOPOLOGY: linear ( i i ) MOLECULE TYPE: peptide ( i i i ) HYPOTHETICAL: NO ( v ) FRAGMENT TYPE: N-terminal ( i x ) FEATURE:
        ( A ) NAME/KEY: Modified-site
        ( B ) LOCATION: 34
        ( D ) OTHER INFORMATION: /note= "Xaa34 = homoserine lactone"

( x i ) SEQUENCE DESCRIPTION: SEQ ID NO:9:

```
Ala Val Ser Glu His Gln Leu Leu His Asp Lys Gly Lys Ser Ile Gln
 1               5                  10                  15
Asp Leu Arg Arg Arg Glu Leu Leu Glu Lys Leu Leu Glu Lys Leu His
            20                  25                  30
```

Thr Xaa (2) INFORMATION FOR SEQ ID NO:10:

(i) SEQUENCE CHARACTERISTICS:
        (A) LENGTH: 37 amino acids
        (B) TYPE: amino acid
        (D) TOPOLOGY: linear (ii) MOLECULE TYPE: peptide (iii) HYPOTHETICAL: NO (xi) SEQUENCE DESCRIPTION: SEQ ID NO:10:

```
Ala Val Ser Glu His Gln Leu Leu His Asp Lys Gly Lys Ser Ile Gln
1               5                   10                  15
Asp Leu Arg Arg Arg Glu Leu Leu Glu Lys Leu Leu Glu Lys Leu His
            20                  25                  30
Thr Ala Gly Arg Arg
            35
```

(2) INFORMATION FOR SEQ ID NO:11:

(i) SEQUENCE CHARACTERISTICS:
        (A) LENGTH: 34 amino acids
        (B) TYPE: amino acid
        (D) TOPOLOGY: linear (ii) MOLECULE TYPE: peptide (iii) HYPOTHETICAL: NO (v) FRAGMENT TYPE: N-terminal (xi) SEQUENCE DESCRIPTION: SEQ ID NO:11:

```
Ala Val Ser Glu His Gln Leu Leu His Asp Lys Gly Lys Ser Ile Gln
1               5                   10                  15
Asp Leu Arg Arg Arg Glu Leu Leu Glu Lys Leu Leu Glu Lys Leu Lys
            20                  25                  30
Glu Leu
```

(2) INFORMATION FOR SEQ ID NO:12:

(i) SEQUENCE CHARACTERISTICS:
        (A) LENGTH: 34 amino acids
        (B) TYPE: amino acid
        (D) TOPOLOGY: linear (ii) MOLECULE TYPE: peptide (iii) HYPOTHETICAL: NO (v) FRAGMENT TYPE: N-terminal (xi) SEQUENCE DESCRIPTION: SEQ ID NO:12:

```
Ala Val Ser Glu His Gln Leu Leu His Asp Lys Gly Lys Ser Ile Gln
1               5                   10                  15
Asp Leu Ala Arg Arg Glu Leu Leu Glu Lys Leu Leu Glu Lys Leu His
            20                  25                  30
Thr Ala
```

(2) INFORMATION FOR SEQ ID NO:13:

(i) SEQUENCE CHARACTERISTICS:
        (A) LENGTH: 34 amino acids
        (B) TYPE: amino acid (D) TOPOLOGY: linear (ii) MOLECULE TYPE: peptide (iii) HYPOTHETICAL: NO (v) FRAGMENT TYPE: N-terminal (xi) SEQUENCE DESCRIPTION: SEQ ID NO:13:

```
Ala Val Ser Glu His Gln Leu Leu His Asp Lys Gly Lys Ser Ile Gln
1               5                   10                  15
Asp Leu Arg Arg Ala Glu Leu Leu Glu Lys Leu Leu Glu Lys Leu His
            20                  25                  30
Thr Ala
```

(2) INFORMATION FOR SEQ ID NO:14:

(i) SEQUENCE CHARACTERISTICS:
(A) LENGTH: 34 amino acids
(B) TYPE: amino acid
(D) TOPOLOGY: linear (ii) MOLECULE TYPE: peptide (iii) HYPOTHETICAL: NO (v) FRAGMENT TYPE: N-terminal (xi) SEQUENCE DESCRIPTION: SEQ ID NO:14:

```
Ala Val Ser Glu Ala Gln Leu Leu His Asp Leu Gly Lys Ser Ile Gln
1               5                   10                  15
Asp Leu Arg Arg Arg Glu Leu Leu Glu Lys Leu Leu Glu Lys Leu His
            20                  25                  30
Ala Leu
```

(2) INFORMATION FOR SEQ ID NO:15:

(i) SEQUENCE CHARACTERISTICS:
(A) LENGTH: 34 amino acids
(B) TYPE: amino acid
(D) TOPOLOGY: linear (ii) MOLECULE TYPE: peptide (iii) HYPOTHETICAL: NO (v) FRAGMENT TYPE: N-terminal (xi) SEQUENCE DESCRIPTION: SEQ ID NO:15:

```
Ala Val Ser Glu His Gln Leu Leu His Asp Lys Gly Lys Ser Ile Gln
1               5                   10                  15
Asp Leu Arg Arg Arg Glu Leu Leu Glu Arg Leu Leu Glu Arg Leu His
            20                  25                  30
Thr Ala
```

(2) INFORMATION FOR SEQ ID NO:16:

(i) SEQUENCE CHARACTERISTICS:
(A) LENGTH: 34 amino acids
(B) TYPE: amino acid
(D) TOPOLOGY: linear (ii) MOLECULE TYPE: peptide (iii) HYPOTHETICAL: NO (v) FRAGMENT TYPE: N-terminal ( x i ) SEQUENCE DESCRIPTION: SEQ ID NO:16:

Ala Val Ser Glu His Gln Leu Leu His Asp Arg Gly Arg Ser Ile Gln
 1               5                   10                  15

Asp Leu Arg Arg Arg Glu Leu Leu Glu Arg Leu Leu Glu Arg Leu His
            20                  25                  30

Thr Ala ( 2 ) INFORMATION FOR SEQ ID NO:17:

( i ) SEQUENCE CHARACTERISTICS:
        ( A ) LENGTH: 34 amino acids
        ( B ) TYPE: amino acid
        ( D ) TOPOLOGY: linear ( i i ) MOLECULE TYPE: peptide ( i i i ) HYPOTHETICAL: NO ( v ) FRAGMENT TYPE: N-terminal ( x i ) SEQUENCE DESCRIPTION: SEQ ID NO:17:

Ala Val Ser Glu His Gln Leu Leu His Asp Arg Gly Arg Ser Ile Gln
 1               5                   10                  15

Asp Leu Arg Arg Arg Glu Leu Leu Glu Arg Leu Leu Lys Arg Leu His
            20                  25                  30

Thr Ala ( 2 ) INFORMATION FOR SEQ ID NO:18:

( i ) SEQUENCE CHARACTERISTICS:
        ( A ) LENGTH: 34 amino acids
        ( B ) TYPE: amino acid
        ( D ) TOPOLOGY: linear ( i i ) MOLECULE TYPE: peptide ( i i i ) HYPOTHETICAL: NO ( v ) FRAGMENT TYPE: N-terminal ( i x ) FEATURE:
        ( A ) NAME/KEY: Modified-site
        ( B ) LOCATION: 29
        ( D ) OTHER INFORMATION: /note= "Xaa29 =
        lysine- $(OCCH_2(OCH_2CH_2)_2OCH_3)$"

( x i ) SEQUENCE DESCRIPTION: SEQ ID NO:18:

Ala Val Ser Glu His Gln Leu Leu His Asp Arg Gly Arg Ser Ile Gln
 1               5                   10                  15

Asp Leu Arg Arg Arg Glu Leu Leu Glu Arg Leu Leu Xaa Arg Leu His
            20                  25                  30

Thr Ala ( 2 ) INFORMATION FOR SEQ ID NO:19:

( i ) SEQUENCE CHARACTERISTICS:
        ( A ) LENGTH: 34 amino acids
        ( B ) TYPE: amino acid
        ( D ) TOPOLOGY: linear ( i i ) MOLECULE TYPE: peptide ( i i i ) HYPOTHETICAL: NO ( v ) FRAGMENT TYPE: N-terminal ( i x ) FEATURE:
        ( A ) NAME/KEY: Modified-site (B) LOCATION: 29
(D) OTHER INFORMATION: /note= "Xaa29 = lysine- (OCCH$_2$(OCH$_2$CH$_2$)$_{110}$OCH$_3$"

(xi) SEQUENCE DESCRIPTION: SEQ ID NO:19:

| Ala | Val | Ser | Glu | His | Gln | Leu | Leu | His | Asp | Arg | Gly | Arg | Ser | Ile | Gln |
|---|---|---|---|---|---|---|---|---|---|---|---|---|---|---|---|
| 1 | | | | 5 | | | | | 10 | | | | | 15 | |

| Asp | Leu | Arg | Arg | Arg | Glu | Leu | Leu | Glu | Arg | Leu | Leu | Xaa | Arg | Leu | His |
|---|---|---|---|---|---|---|---|---|---|---|---|---|---|---|---|
| | | | 20 | | | | | 25 | | | | | 30 | | |

Thr Ala (2) INFORMATION FOR SEQ ID NO:20:

(i) SEQUENCE CHARACTERISTICS:
(A) LENGTH: 34 amino acids
(B) TYPE: amino acid
(D) TOPOLOGY: linear (ii) MOLECULE TYPE: peptide (iii) HYPOTHETICAL: NO (v) FRAGMENT TYPE: N-terminal (xi) SEQUENCE DESCRIPTION: SEQ ID NO:20:

| Ala | Val | Ser | Glu | His | Gln | Leu | Leu | His | Asp | Lys | Gly | Lys | Ser | Ile | Gln |
|---|---|---|---|---|---|---|---|---|---|---|---|---|---|---|---|
| 1 | | | | 5 | | | | | 10 | | | | | 15 | |

| Asp | Leu | Arg | Arg | Arg | Ala | Leu | Ala | Glu | Ala | Leu | Ala | Glu | Ala | Leu | His |
|---|---|---|---|---|---|---|---|---|---|---|---|---|---|---|---|
| | | | 20 | | | | | 25 | | | | | 30 | | |

Thr Ala (2) INFORMATION FOR SEQ ID NO:21:

(i) SEQUENCE CHARACTERISTICS:
(A) LENGTH: 34 amino acids
(B) TYPE: amino acid
(D) TOPOLOGY: linear (ii) MOLECULE TYPE: peptide (iii) HYPOTHETICAL: NO (v) FRAGMENT TYPE: N-terminal (xi) SEQUENCE DESCRIPTION: SEQ ID NO:21:

| Ala | Val | Ser | Glu | His | Gln | Leu | Leu | His | Asp | Lys | Gly | Lys | Ser | Ile | Gln |
|---|---|---|---|---|---|---|---|---|---|---|---|---|---|---|---|
| 1 | | | | 5 | | | | | 10 | | | | | 15 | |

| Asp | Leu | Arg | Arg | Arg | Ser | Leu | Leu | Ser | Ser | Leu | Leu | Ser | Ser | Leu | His |
|---|---|---|---|---|---|---|---|---|---|---|---|---|---|---|---|
| | | | 20 | | | | | 25 | | | | | 30 | | |

Thr Ala (2) INFORMATION FOR SEQ ID NO:22:

(i) SEQUENCE CHARACTERISTICS:
(A) LENGTH: 34 amino acids
(B) TYPE: amino acid
(D) TOPOLOGY: linear (ii) MOLECULE TYPE: peptide (iii) HYPOTHETICAL: NO (v) FRAGMENT TYPE: N-terminal (xi) SEQUENCE DESCRIPTION: SEQ ID NO:22:

| Ala | Val | Ser | Glu | His | Gln | Leu | Leu | His | Asp | Lys | Gly | Lys | Ser | Ile | Gln |
|---|---|---|---|---|---|---|---|---|---|---|---|---|---|---|---|
| 1 | | | | 5 | | | | | 10 | | | | | 15 | |

-continued

```
Asp  Leu  Arg  Arg  Arg  Ala  Phe  Tyr  Asp  Lys  Val  Ala  Glu  Lys  Leu  His
               20                      25                      30

Thr  Ala
```

( 2 ) INFORMATION FOR SEQ ID NO:23:

( i ) SEQUENCE CHARACTERISTICS:
        ( A ) LENGTH: 34 amino acids
        ( B ) TYPE: amino acid
        ( D ) TOPOLOGY: linear ( i i ) MOLECULE TYPE: peptide ( i i i ) HYPOTHETICAL: NO ( v ) FRAGMENT TYPE: N-terminal ( i x ) FEATURE:
        ( A ) NAME/KEY: Modified-site
        ( B ) LOCATION: 8
        ( D ) OTHER INFORMATION: /note= "Xaa8 = norleucine"

( i x ) FEATURE:
        ( A ) NAME/KEY: Modified-site
        ( B ) LOCATION: 18
        ( D ) OTHER INFORMATION: /note= "Xaa18 = norleucine"

( x i ) SEQUENCE DESCRIPTION: SEQ ID NO:23:

```
Ala  Val  Ser  Glu  Ile  Gln  Phe  Xaa  His  Asn  Leu  Gly  Lys  His  Leu  Ser
1                      5                      10                      15

Ser  Xaa  Glu  Arg  Val  Glu  Leu  Leu  Glu  Lys  Leu  Leu  Glu  Lys  Leu  His
               20                      25                      30

Asn  Tyr
```

( 2 ) INFORMATION FOR SEQ ID NO:24:

( i ) SEQUENCE CHARACTERISTICS:
        ( A ) LENGTH: 34 amino acids
        ( B ) TYPE: amino acid
        ( D ) TOPOLOGY: linear ( i i ) MOLECULE TYPE: peptide ( i i i ) HYPOTHETICAL: NO ( v ) FRAGMENT TYPE: N-terminal ( i x ) FEATURE:
        ( A ) NAME/KEY: Modified-site
        ( B ) LOCATION: 8
        ( D ) OTHER INFORMATION: /note= "Xaa8 = norleucine"

( i x ) FEATURE:
        ( A ) NAME/KEY: Modified-site
        ( B ) LOCATION: 18
        ( D ) OTHER INFORMATION: /note= "Xaa18 = norleucine"

( x i ) SEQUENCE DESCRIPTION: SEQ ID NO:24:

```
Ala  Val  Ser  Glu  Ile  Gln  Phe  Xaa  His  Asn  Leu  Gly  Lys  His  Leu  Ser
1                      5                      10                      15

Ser  Xaa  Arg  Arg  Arg  Glu  Leu  Leu  Glu  Lys  Leu  Leu  Glu  Lys  Leu  His
               20                      25                      30

Asn  Tyr
```

( 2 ) INFORMATION FOR SEQ ID NO:25:

( i ) SEQUENCE CHARACTERISTICS:
        ( A ) LENGTH: 35 amino acids
        ( B ) TYPE: amino acid (D) TOPOLOGY: linear (ii) MOLECULE TYPE: peptide (iii) HYPOTHETICAL: NO (v) FRAGMENT TYPE: N-terminal (xi) SEQUENCE DESCRIPTION: SEQ ID NO:25:

| Ala | Val | Ser | Glu | His | Gln | Leu | Leu | His | Asp | Lys | Gly | Lys | Ser | Ile | Gln |
|---|---|---|---|---|---|---|---|---|---|---|---|---|---|---|---|
| 1 | | | | 5 | | | | | 10 | | | | | | 15 |

| Asp | Leu | Arg | Arg | Arg | Glu | Leu | Leu | Glu | Lys | Leu | Leu | Glu | Lys | Leu | His |
|---|---|---|---|---|---|---|---|---|---|---|---|---|---|---|---|
| | | | 20 | | | | | 25 | | | | | 30 | | |

| Thr | Met | Ala |
|---|---|---|
| | | 35 |

(2) INFORMATION FOR SEQ ID NO:26:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (iii) HYPOTHETICAL: NO (v) FRAGMENT TYPE: internal (ix) FEATURE:
        (A) NAME/KEY: Modified-site
        (B) LOCATION: 8
        (D) OTHER INFORMATION: /note= "Xaa8 = glutamic acid or arginine"

(ix) FEATURE:
        (A) NAME/KEY: Region
        (B) LOCATION: 1..10
        (D) OTHER INFORMATION: /note= "Sequence 26 is embedded at positions 22 to 31 of sequences 5, 6, 7, 8, 9, 10, 11, 12, 13, and 14."

(xi) SEQUENCE DESCRIPTION: SEQ ID NO:26:

| Glu | Leu | Leu | Glu | Lys | Leu | Leu | Xaa | Lys | Leu |
|---|---|---|---|---|---|---|---|---|---|
| 1 | | | | 5 | | | | | 10 |

(2) INFORMATION FOR SEQ ID NO:27:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (iii) HYPOTHETICAL: NO (v) FRAGMENT TYPE: internal (ix) FEATURE:
        (A) NAME/KEY: Modified-site
        (B) LOCATION: 8
        (D) OTHER INFORMATION: /note= "Xaa8 = glutamic acid, lysine, or lysine-(OCCH2PEGX)"

(ix) FEATURE:
        (A) NAME/KEY: Region
        (B) LOCATION: 1..10
        (D) OTHER INFORMATION: /note= "Sequence 27 is embedded at positions 22 to 31 of sequences 15, 16, 17, 18, and 19."

(xi) SEQUENCE DESCRIPTION: SEQ ID NO:27:

```
Glu  Leu  Leu  Glu  Arg  Leu  Leu  Xaa  Arg  Leu
1                   5                    10
```

(2) INFORMATION FOR SEQ ID NO:28:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (iii) HYPOTHETICAL: NO (v) FRAGMENT TYPE: internal (ix) FEATURE:
        (A) NAME/KEY: Peptide
        (B) LOCATION: 1..10
        (D) OTHER INFORMATION: /note= "Sequence 28 is embedded at positions 22 to 31 of sequence 20."

(xi) SEQUENCE DESCRIPTION: SEQ ID NO:28:

```
Ala  Leu  Ala  Glu  Ala  Leu  Ala  Glu  Ala  Leu
1                   5                    10
```

(2) INFORMATION FOR SEQ ID NO:29:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (iii) HYPOTHETICAL: NO (v) FRAGMENT TYPE: internal (ix) FEATURE:
        (A) NAME/KEY: Peptide
        (B) LOCATION: 1..10
        (D) OTHER INFORMATION: /note= "Sequence 29 is embedded at positions 22 to 31 of sequence 21."

(xi) SEQUENCE DESCRIPTION: SEQ ID NO:29:

```
Ser  Leu  Leu  Ser  Ser  Leu  Leu  Ser  Ser  Leu
1                   5                    10
```

(2) INFORMATION FOR SEQ ID NO:30:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (iii) HYPOTHETICAL: NO (v) FRAGMENT TYPE: internal (ix) FEATURE:
        (A) NAME/KEY: Peptide
        (B) LOCATION: 1..10
        (D) OTHER INFORMATION: /note= "Sequence 30 is embedded at positions 22 to 31 of sequence 22."

(xi) SEQUENCE DESCRIPTION: SEQ ID NO:30:

```
Ala  Phe  Tyr  Asp  Lys  Val  Ala  Glu  Lys  Leu
1                   5                    10
```

(2) INFORMATION FOR SEQ ID NO:31:

( i ) SEQUENCE CHARACTERISTICS:
  ( A ) LENGTH: 88 base pairs
  ( B ) TYPE: nucleic acid
  ( C ) STRANDEDNESS: single
  ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:31:

CCTCTAGATC TCCGCGGCGC TAGCATGGCT GTTTCTGAAC ATCAGCTGCT TCATGACAAA 60

GGTAAATCGA TTCAAGATCT GAGACGTC 88

( 2 ) INFORMATION FOR SEQ ID NO:32:

( i ) SEQUENCE CHARACTERISTICS:
    ( A ) LENGTH: 90 base pairs
    ( B ) TYPE: nucleic acid
    ( C ) STRANDEDNESS: single
    ( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:32:

CCTCGAAGCT TATGCATCAT TATCTAGACA TAGTATGCAG CTTTTCAAGC AGTTTCTCCA 60

GCAGCTCGCG ACGTCTCAGA TCTTGAATCG 90

( 2 ) INFORMATION FOR SEQ ID NO:33:

( i ) SEQUENCE CHARACTERISTICS:
    ( A ) LENGTH: 23 base pairs
    ( B ) TYPE: nucleic acid
    ( C ) STRANDEDNESS: single
    ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:33:

CCTCTAGATC TCCGCGCGCT AGC 23

( 2 ) INFORMATION FOR SEQ ID NO:34:

( i ) SEQUENCE CHARACTERISTICS:
    ( A ) LENGTH: 24 base pairs
    ( B ) TYPE: nucleic acid
    ( C ) STRANDEDNESS: single
    ( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:34:

CCTCGAAGCT TATGCATCAT TATC 24

( 2 ) INFORMATION FOR SEQ ID NO: 35:

( i ) SEQUENCE CHARACTERISTICS:
   ( A ) LENGTH: 34 amino acids
   ( B ) TYPE: amino acid
   ( D ) TOPOLOGY: linear ( i i ) MOLECULE TYPE: protein ( i i i ) HYPOTHETICAL: NO ( v ) FRAGMENT TYPE: N-terminal ( x i ) SEQUENCE DESCRIPTION: SEQ ID NO: 35:

```
Ala Val Ser Glu Ile Gln Phe Leu His Asn Leu Gly Lys His Leu Ser
 1               5                  10                  15
Ser Leu Arg Arg Arg Glu Leu Leu Glu Lys Leu Leu Glu Lys Leu His
             20                  25                  30
Asn Tyr
```

( 2 ) INFORMATION FOR SEQ ID NO: 36:

( i ) SEQUENCE CHARACTERISTICS:
   ( A ) LENGTH: 34 amino acids
   ( B ) TYPE: amino acid
   ( D ) TOPOLOGY: linear ( i i ) MOLECULE TYPE: protein ( i i i ) HYPOTHETICAL: NO ( v ) FRAGMENT TYPE: N-terminal ( i x ) FEATURE:
   ( A ) NAME/KEY: Modified-site
   ( B ) LOCATION: 34
   ( D ) OTHER INFORMATION: /note= "Xaa is homoserine"

( x i ) SEQUENCE DESCRIPTION: SEQ ID NO: 36:

```
Ala Val Ser Glu Ile Gln Phe Leu His Asn Leu Gly Lys His Leu Ser
 1               5                  10                  15
Ser Leu Arg Arg Arg Glu Leu Leu Glu Lys Leu Leu Glu Lys Leu His
             20                  25                  30
Asn Xaa
```

( 2 ) INFORMATION FOR SEQ ID NO: 37:

( i ) SEQUENCE CHARACTERISTICS:
   ( A ) LENGTH: 34 amino acids
   ( B ) TYPE: amino acid
   ( D ) TOPOLOGY: linear ( i i ) MOLECULE TYPE: protein ( i i i ) HYPOTHETICAL: NO ( v ) FRAGMENT TYPE: N-terminal ( i x ) FEATURE:
   ( A ) NAME/KEY: Modified-site
   ( B ) LOCATION: 34
   ( D ) OTHER INFORMATION: /note= "Xaa is homoserine"

( x i ) SEQUENCE DESCRIPTION: SEQ ID NO: 37:

```
Ala Val Ser Glu Ile Gln Phe Leu His Asn Lys Gly Lys His Leu Ser
 1               5                  10                  15
Ser Leu Arg Arg Arg Glu Leu Leu Glu Lys Leu Leu Glu Lys Leu His
             20                  25                  30
Asn Xaa
```

( 2 ) INFORMATION FOR SEQ ID NO: 38:

( i ) SEQUENCE CHARACTERISTICS:
        ( A ) LENGTH: 34 amino acids
        ( B ) TYPE: amino acid
        ( D ) TOPOLOGY: linear ( i i ) MOLECULE TYPE: protein ( i i i ) HYPOTHETICAL: NO ( v ) FRAGMENT TYPE: N-terminal ( x i ) SEQUENCE DESCRIPTION: SEQ ID NO: 38:

```
Ala Val Ser Glu His Gln Leu Leu His Asp Lys Gly Lys Ser Ile Gln
1               5                   10                  15
Asp Leu Lys Leu Lys Glu Leu Leu Glu Lys Leu Leu Glu Lys Leu His
            20                  25                  30
Thr Ala
```

( 2 ) INFORMATION FOR SEQ ID NO: 39:

( i ) SEQUENCE CHARACTERISTICS:
        ( A ) LENGTH: 34 amino acids
        ( B ) TYPE: amino acid
        ( D ) TOPOLOGY: linear ( i i ) MOLECULE TYPE: protein ( i i i ) HYPOTHETICAL: NO ( v ) FRAGMENT TYPE: N-terminal ( x i ) SEQUENCE DESCRIPTION: SEQ ID NO: 39:

```
Ala Val Ser Glu His Gln Leu Leu His Asp Lys Gly Lys Ser Ile Gln
1               5                   10                  15
Asp Leu Arg Arg Arg Glu Leu Leu Glu Arg Leu Leu Glu Arg Leu His
            20                  25                  30
Thr Ala
```

( 2 ) INFORMATION FOR SEQ ID NO: 40:

( i ) SEQUENCE CHARACTERISTICS:
        ( A ) LENGTH: 35 amino acids
        ( B ) TYPE: amino acid
        ( D ) TOPOLOGY: linear ( i i ) MOLECULE TYPE: protein ( i i i ) HYPOTHETICAL: NO ( v ) FRAGMENT TYPE: N-terminal ( x i ) SEQUENCE DESCRIPTION: SEQ ID NO: 40:

```
Ala Val Ser Glu His Gln Leu Leu His Asp Lys Gly Lys Ser Ile Gln
1               5                   10                  15
Asp Leu Arg Arg Arg Glu Leu Leu Glu Arg Leu Leu Glu Arg Leu His
            20                  25                  30
Thr Ala Pro
        35
```

( 2 ) INFORMATION FOR SEQ ID NO: 41:

( i ) SEQUENCE CHARACTERISTICS:
        ( A ) LENGTH: 37 amino acids
        ( B ) TYPE: amino acid
        ( D ) TOPOLOGY: linear (i i) MOLECULE TYPE: protein (i i i) HYPOTHETICAL: NO (v) FRAGMENT TYPE: N-terminal (x i) SEQUENCE DESCRIPTION: SEQ ID NO: 41:

```
Ala Val Ser Glu His Gln Leu Leu His Asp Lys Gly Lys Ser Ile Gln
1               5                   10                  15
Asp Leu Arg Arg Arg Glu Leu Leu Glu Arg Leu Leu Glu Arg Leu His
            20                  25                  30
Thr Ala Gly Arg Arg
            35
```

(2) INFORMATION FOR SEQ ID NO: 42:

(i) SEQUENCE CHARACTERISTICS:
    (A) LENGTH: 38 amino acids
    (B) TYPE: amino acid
    (D) TOPOLOGY: linear (i i) MOLECULE TYPE: protein (i i i) HYPOTHETICAL: NO (v) FRAGMENT TYPE: N-terminal (i x) FEATURE:
    (A) NAME/KEY: Modified-site
    (B) LOCATION: 38
    (D) OTHER INFORMATION: /note= "Xaa is homoserine"

(x i) SEQUENCE DESCRIPTION: SEQ ID NO: 42:

```
Ala Val Ser Glu His Gln Leu Leu His Asp Lys Gly Lys Ser Ile Gln
1               5                   10                  15
Asp Leu Arg Arg Arg Glu Leu Leu Glu Arg Leu Leu Glu Arg Leu His
            20                  25                  30
Thr Ala Gly Arg Arg Xaa
            35
```

(2) INFORMATION FOR SEQ ID NO: 43:

(i) SEQUENCE CHARACTERISTICS:
    (A) LENGTH: 34 amino acids
    (B) TYPE: amino acid
    (D) TOPOLOGY: linear (i i) MOLECULE TYPE: protein (i i i) HYPOTHETICAL: NO (v) FRAGMENT TYPE: N-terminal (x i) SEQUENCE DESCRIPTION: SEQ ID NO: 43:

```
Ala Val Ser Glu His Gln Leu Leu His Asp Lys Gly Lys Ser Ile Gln
1               5                   10                  15
Asp Leu Arg Arg Arg Glu Leu Leu Glu Lys Leu Leu Glu Lys Leu His
            20                  25                  30
Thr Tyr
```

(2) INFORMATION FOR SEQ ID NO: 44:

(i) SEQUENCE CHARACTERISTICS:
    (A) LENGTH: 34 amino acids
    (B) TYPE: amino acid
    (D) TOPOLOGY: linear (i i) MOLECULE TYPE: protein (i i i) HYPOTHETICAL: NO (v) FRAGMENT TYPE: N-terminal (x i) SEQUENCE DESCRIPTION: SEQ ID NO: 44:

| Ala | Val | Ser | Glu | His | Gln | Leu | Leu | His | Asp | Lys | Gly | Tyr | Ser | Ile | Gln |
| 1 | | | | 5 | | | | | 10 | | | | | 15 | |

| Asp | Leu | Arg | Arg | Arg | Glu | Leu | Leu | Glu | Lys | Leu | Leu | Glu | Lys | Leu | His |
| | | | 20 | | | | | 25 | | | | | 30 | | |

Thr Ala (2) INFORMATION FOR SEQ ID NO: 45:

(i) SEQUENCE CHARACTERISTICS:
      (A) LENGTH: 34 amino acids
      (B) TYPE: amino acid
      (D) TOPOLOGY: linear (i i) MOLECULE TYPE: protein (i i i) HYPOTHETICAL: NO (v) FRAGMENT TYPE: N-terminal (x i) SEQUENCE DESCRIPTION: SEQ ID NO: 45:

| Ala | Val | Ser | Glu | His | Gln | Leu | Leu | His | Asp | Lys | Gly | Cys | Ser | Ile | Gln |
| 1 | | | | 5 | | | | | 10 | | | | | 15 | |

| Asp | Leu | Arg | Arg | Arg | Glu | Leu | Leu | Glu | Lys | Leu | Leu | Glu | Lys | Leu | His |
| | | | 20 | | | | | 25 | | | | | 30 | | |

Thr Ala (2) INFORMATION FOR SEQ ID NO: 46:

(i) SEQUENCE CHARACTERISTICS:
      (A) LENGTH: 34 amino acids
      (B) TYPE: amino acid
      (D) TOPOLOGY: linear (i i) MOLECULE TYPE: protein (i i i) HYPOTHETICAL: NO (v) FRAGMENT TYPE: N-terminal (i x) FEATURE:
      (A) NAME/KEY: Modified-site
      (B) LOCATION: 13
      (D) OTHER INFORMATION: /note= "Xaa is
          Cys(CH- 2CONH(CH-2)-2NH(biotinyl))"

(x i) SEQUENCE DESCRIPTION: SEQ ID NO: 46:

| Ala | Val | Ser | Glu | His | Gln | Leu | Leu | His | Asp | Lys | Gly | Xaa | Ser | Ile | Gln |
| 1 | | | | 5 | | | | | 10 | | | | | 15 | |

| Asp | Leu | Arg | Arg | Arg | Glu | Leu | Leu | Glu | Lys | Leu | Leu | Glu | Lys | Leu | His |
| | | | 20 | | | | | 25 | | | | | 30 | | |

Thr Ala (2) INFORMATION FOR SEQ ID NO: 47:

(i) SEQUENCE CHARACTERISTICS:
      (A) LENGTH: 34 amino acids
      (B) TYPE: amino acid
      (D) TOPOLOGY: linear (i i) MOLECULE TYPE: protein ( i i i ) HYPOTHETICAL: NO ( v ) FRAGMENT TYPE: N-terminal ( i x ) FEATURE:
    ( A ) NAME/KEY: Modified-site
    ( B ) LOCATION: 13
    ( D ) OTHER INFORMATION: /note= "Xaa is
        Lys(7- dimethylamino-2-oxo-2H-1-benxopyran-4-acety
        l)"

( x i ) SEQUENCE DESCRIPTION: SEQ ID NO: 47:

```
Ala  Val  Ser  Glu  His  Gln  Leu  Leu  His  Asp  Lys  Gly  Xaa  Ser  Ile  Gln
 1              5                        10                       15

Asp  Leu  Arg  Arg  Arg  Glu  Leu  Leu  Glu  Lys  Leu  Leu  Glu  Lys  Leu  His
               20                        25                       30

Thr  Ala
```

( 2 ) INFORMATION FOR SEQ ID NO: 48:

( i ) SEQUENCE CHARACTERISTICS:
        ( A ) LENGTH: 35 amino acids
        ( B ) TYPE: amino acid
        ( D ) TOPOLOGY: linear ( i i ) MOLECULE TYPE: protein ( i i i ) HYPOTHETICAL: NO ( v ) FRAGMENT TYPE: N-terminal ( x i ) SEQUENCE DESCRIPTION: SEQ ID NO: 48:

```
Ala  Val  Ser  Glu  His  Gln  Leu  Leu  His  Asp  Lys  Gly  Lys  Ser  Ile  Gln
 1              5                        10                       15

Asp  Leu  Arg  Arg  Arg  Glu  Leu  Leu  Glu  Lys  Leu  Leu  Glu  Lys  Leu  His
               20                        25                       30

Thr  Ala  Gly
          35
```

( 2 ) INFORMATION FOR SEQ ID NO: 49:

( i ) SEQUENCE CHARACTERISTICS:
        ( A ) LENGTH: 33 amino acids
        ( B ) TYPE: amino acid
        ( D ) TOPOLOGY: linear ( i i ) MOLECULE TYPE: protein ( i i i ) HYPOTHETICAL: NO ( v ) FRAGMENT TYPE: N-terminal ( i x ) FEATURE:
        ( A ) NAME/KEY: Modified-site
        ( B ) LOCATION: 4
        ( D ) OTHER INFORMATION: /note= "Xaa4 is Glu(OCH-3)"

( i x ) FEATURE:
        ( A ) NAME/KEY: Modified-site
        ( B ) LOCATION: 10
        ( D ) OTHER INFORMATION: /note= "Xaa10 is Asp(OCH-3)"

( i x ) FEATURE:
        ( A ) NAME/KEY: Modified-site
        ( B ) LOCATION: 17
        ( D ) OTHER INFORMATION: /note= "Xaa17 is Asp(OCH-3)"

( i x ) FEATURE:
        ( A ) NAME/KEY: Modified-site
        ( B ) LOCATION: 22
        ( D ) OTHER INFORMATION: /note= "Xaa22 is Glu(OCH3)"

(ix) FEATURE:
    (A) NAME/KEY: Modified-site
    (B) LOCATION: 25
    (D) OTHER INFORMATION: /note= "Xaa25 is Glu(OCH-3)"

(ix) FEATURE:
    (A) NAME/KEY: Modified-site
    (B) LOCATION: 29
    (D) OTHER INFORMATION: /note= "Xaa29 is Glu(OCH-3)"

(xi) SEQUENCE DESCRIPTION: SEQ ID NO: 49:

```
Ala  Val  Ser  Xaa  His  Gln  Leu  Leu  His  Xaa  Lys  Gly  Lys  Ser  Ile  Gln
1              5                        10                       15
Xaa  Leu  Arg  Arg  Arg  Xaa  Leu  Leu  Xaa  Lys  Leu  Leu  Xaa  Lys  Leu  His
               20                       25                       30
Ala
```

(2) INFORMATION FOR SEQ ID NO: 50:

(i) SEQUENCE CHARACTERISTICS:
    (A) LENGTH: 33 amino acids
    (B) TYPE: amino acid
    (D) TOPOLOGY: linear (ii) MOLECULE TYPE: protein (iii) HYPOTHETICAL: NO (v) FRAGMENT TYPE: N-terminal (ix) FEATURE:
    (A) NAME/KEY: Modified-site
    (B) LOCATION: 4
    (D) OTHER INFORMATION: /note= "Xaa4 is Glu(OCH-3)"

(ix) FEATURE:
    (A) NAME/KEY: Modified-site
    (B) LOCATION: 10
    (D) OTHER INFORMATION: /note= "Xaa10 is Asp(OCH-3)"

(ix) FEATURE:
    (A) NAME/KEY: Modified-site
    (B) LOCATION: 17
    (D) OTHER INFORMATION: /note= "Xaa17 is Asp(OCH-3)"

(ix) FEATURE:
    (A) NAME/KEY: Modified-site
    (B) LOCATION: 22
    (D) OTHER INFORMATION: /note= "Xaa22 is Glu(OCH-3)"

(ix) FEATURE:
    (A) NAME/KEY: Modified-site
    (B) LOCATION: 25
    (D) OTHER INFORMATION: /note= "Xaa25 is Glu(OCH-3)"

(ix) FEATURE:
    (A) NAME/KEY: Modified-site
    (B) LOCATION: 29
    (D) OTHER INFORMATION: /note= "Xaa29 is Glu(OCH-3)"

(xi) SEQUENCE DESCRIPTION: SEQ ID NO: 50:

```
Ala  Val  Ser  Xaa  His  Gln  Leu  Leu  His  Xaa  Lys  Gly  Lys  Ser  Ile  Gln
1              5                        10                       15
Xaa  Leu  Arg  Arg  Arg  Xaa  Leu  Leu  Xaa  Lys  Leu  Leu  Xaa  Lys  Leu  His
               20                       25                       30
Ala
```

(2) INFORMATION FOR SEQ ID NO: 51:

(i) SEQUENCE CHARACTERISTICS:
    (A) LENGTH: 34 amino acids
    (B) TYPE: amino acid -continued (D) TOPOLOGY: linear (ii) MOLECULE TYPE: protein (iii) HYPOTHETICAL: NO (v) FRAGMENT TYPE: N-terminal (ix) FEATURE:
  (A) NAME/KEY: Modified-site
  (B) LOCATION: 34
  (D) OTHER INFORMATION: /note= "Xaa is homoserine"

(xi) SEQUENCE DESCRIPTION: SEQ ID NO: 51:

```
Ala Val Ser Glu His Gln Leu Leu His Asp Lys Gly Lys Ser Ile Gln
 1               5                   10                  15
Asp Leu Arg Arg Arg Glu Leu Leu Glu Lys Leu Leu Glu Lys Leu His
            20                  25                  30
Thr Xaa
```

(2) INFORMATION FOR SEQ ID NO: 52:

(i) SEQUENCE CHARACTERISTICS:
    (A) LENGTH: 35 amino acids
    (B) TYPE: amino acid
    (D) TOPOLOGY: linear (ii) MOLECULE TYPE: protein (iii) HYPOTHETICAL: NO (v) FRAGMENT TYPE: N-terminal (xi) SEQUENCE DESCRIPTION: SEQ ID NO: 52:

```
Ala Val Ser Glu His Gln Leu Leu His Asp Lys Gly Lys Ser Ile Gln
 1               5                   10                  15
Asp Leu Arg Arg Arg Glu Leu Leu Glu Lys Leu Leu Glu Lys Leu His
            20                  25                  30
Thr Ala Pro
        35
```

(2) INFORMATION FOR SEQ ID NO: 53:

(i) SEQUENCE CHARACTERISTICS:
    (A) LENGTH: 34 amino acids
    (B) TYPE: amino acid
    (D) TOPOLOGY: linear (ii) MOLECULE TYPE: protein (iii) HYPOTHETICAL: NO (v) FRAGMENT TYPE: N-terminal (xi) SEQUENCE DESCRIPTION: SEQ ID NO: 53:

```
Ala Val Ser Glu His Gln Leu Leu His Asp Lys Gly Lys Ser Ile Gln
 1               5                   10                  15
Asp Leu Arg Arg Arg Glu Leu Leu Glu Lys Leu Leu Glu Lys Leu His
            20                  25                  30
Thr Pro
```

(2) INFORMATION FOR SEQ ID NO: 54:

(i) SEQUENCE CHARACTERISTICS:
    (A) LENGTH: 34 amino acids
    (B) TYPE: amino acid
    (D) TOPOLOGY: linear ( i i ) MOLECULE TYPE: protein ( i i i ) HYPOTHETICAL: NO ( v ) FRAGMENT TYPE: N-terminal ( x i ) SEQUENCE DESCRIPTION: SEQ ID NO: 54:

Ala Val Ser Glu His Gln Leu Leu His Asp Lys Gly Lys Ser Ile Gln
1               5                   10                  15

Asp Leu Arg Arg Arg Glu Leu Leu Glu Lys Leu Leu Glu Lys Leu His
            20                  25                  30

Thr Pro ( 2 ) INFORMATION FOR SEQ ID NO: 55:

( i ) SEQUENCE CHARACTERISTICS:
        ( A ) LENGTH: 33 amino acids
        ( B ) TYPE: amino acid
        ( D ) TOPOLOGY: linear ( i i ) MOLECULE TYPE: protein ( i i i ) HYPOTHETICAL: NO ( v ) FRAGMENT TYPE: N-terminal ( x i ) SEQUENCE DESCRIPTION: SEQ ID NO: 55:

Ala Val Ser Glu His Gln Leu Leu His Asp Lys Gly Lys Ser Ile Gln
1               5                   10                  15

Asp Leu Arg Arg Arg Glu Leu Leu Glu Lys Leu Leu Glu Lys Leu His
            20                  25                  30

Pro ( 2 ) INFORMATION FOR SEQ ID NO: 56:

( i ) SEQUENCE CHARACTERISTICS:
        ( A ) LENGTH: 32 amino acids
        ( B ) TYPE: amino acid
        ( D ) TOPOLOGY: linear ( i i ) MOLECULE TYPE: protein ( i i i ) HYPOTHETICAL: NO ( v ) FRAGMENT TYPE: N-terminal ( x i ) SEQUENCE DESCRIPTION: SEQ ID NO: 56:

Ala Val Ser Glu His Gln Leu Leu His Asp Lys Gly Lys Ser Ile Gln
1               5                   10                  15

Asp Leu Arg Arg Arg Glu Leu Leu Glu Lys Leu Leu Glu Lys Leu Pro
            20                  25                  30

( 2 ) INFORMATION FOR SEQ ID NO: 57:

( i ) SEQUENCE CHARACTERISTICS:
        ( A ) LENGTH: 37 amino acids
        ( B ) TYPE: amino acid
        ( D ) TOPOLOGY: linear ( i i ) MOLECULE TYPE: protein ( i i i ) HYPOTHETICAL: NO ( v ) FRAGMENT TYPE: N-terminal ( x i ) SEQUENCE DESCRIPTION: SEQ ID NO: 57:

Ala Val Ser Glu His Gln Leu Leu His Asp Lys Gly Lys Ser Ile Gln
1               5                   10                  15

```
         Asp  Leu  Arg  Arg  Arg  Glu  Leu  Leu  Glu  Lys  Leu  Leu  Glu  Lys  Leu  His
                        20                      25                     30

Thr  Arg  Ser  Ala  Trp
                        35
```

(2) INFORMATION FOR SEQ ID NO: 58:

(i) SEQUENCE CHARACTERISTICS:
    (A) LENGTH: 42 amino acids
    (B) TYPE: amino acid
    (D) TOPOLOGY: linear (ii) MOLECULE TYPE: protein (iii) HYPOTHETICAL: NO (v) FRAGMENT TYPE: N-terminal (xi) SEQUENCE DESCRIPTION: SEQ ID NO: 58:

```
         Ala  Val  Ser  Glu  His  Gln  Leu  Leu  His  Asp  Arg  Gly  Arg  Ser  Ile  Gln
         1                   5                        10                      15

Asp  Leu  Arg  Arg  Arg  Glu  Leu  Leu  Glu  Arg  Leu  Leu  Glu  Arg  Leu  His
                        20                      25                     30

Thr  Ala  Gly  Arg  Arg  Thr  Arg  Ser  Ala  Trp
                        35                      40
```

(2) INFORMATION FOR SEQ ID NO: 59:

(i) SEQUENCE CHARACTERISTICS:
    (A) LENGTH: 42 amino acids
    (B) TYPE: amino acid
    (D) TOPOLOGY: linear (ii) MOLECULE TYPE: protein (iii) HYPOTHETICAL: NO (v) FRAGMENT TYPE: N-terminal (xi) SEQUENCE DESCRIPTION: SEQ ID NO: 59:

```
         Ala  Val  Ser  Glu  His  Gln  Leu  Leu  His  Asp  Arg  Gly  Arg  Ser  Ile  Gln
         1                   5                        10                      15

Asp  Leu  Arg  Arg  Arg  Glu  Leu  Leu  Glu  Arg  Leu  Leu  Glu  Arg  Leu  His
                        20                      25                     30

Thr  Arg  Gly  Arg  Arg  Thr  Arg  Ser  Ala  Trp
                        35                      40
```

(2) INFORMATION FOR SEQ ID NO: 60:

(i) SEQUENCE CHARACTERISTICS:
    (A) LENGTH: 42 amino acids
    (B) TYPE: amino acid
    (D) TOPOLOGY: linear (ii) MOLECULE TYPE: protein (iii) HYPOTHETICAL: NO (v) FRAGMENT TYPE: N-terminal (ix) FEATURE:
    (A) NAME/KEY: Modified-site
    (B) LOCATION: 13
    (D) OTHER INFORMATION: /note= "Xaa13 is
        Lys(dihydrocinnamoyl)"

(xi) SEQUENCE DESCRIPTION: SEQ ID NO: 60:

```
Ala Val Ser Glu His Gln Leu Leu His Asp Arg Gly Xaa Ser Ile Gln
1               5                   10                  15

Asp Leu Arg Arg Arg Glu Leu Leu Glu Arg Leu Leu Glu Arg Leu His
            20                  25                  30

Thr Arg Gly Arg Arg Thr Arg Ser Ala Trp
            35                  40
```

(2) INFORMATION FOR SEQ ID NO: 61:

(i) SEQUENCE CHARACTERISTICS:
        (A) LENGTH: 34 amino acids
        (B) TYPE: amino acid
        (D) TOPOLOGY: linear (ii) MOLECULE TYPE: protein (iii) HYPOTHETICAL: NO (v) FRAGMENT TYPE: N-terminal (ix) FEATURE:
        (A) NAME/KEY: Modified-site
        (B) LOCATION: 8
        (D) OTHER INFORMATION: /note= "Leu8 is Norleucine"

(ix) FEATURE:
        (A) NAME/KEY: Modified-site
        (B) LOCATION: 18
        (D) OTHER INFORMATION: /note= "Leu18 is Norleucine"

(xi) SEQUENCE DESCRIPTION: SEQ ID NO: 61:

```
Ala Val Ser Glu Ile Gln Phe Leu His Asn Leu Gly Lys His Leu Ser
1               5                   10                  15

Ser Leu Thr Arg Ser Ala Trp Leu Arg Lys Lys Leu Gln Asp Val His
            20                  25                  30

Asn Tyr
```

(2) INFORMATION FOR SEQ ID NO: 62:

(i) SEQUENCE CHARACTERISTICS:
        (A) LENGTH: 35 amino acids
        (B) TYPE: amino acid
        (D) TOPOLOGY: linear (ii) MOLECULE TYPE: protein (iii) HYPOTHETICAL: NO (v) FRAGMENT TYPE: N-terminal (xi) SEQUENCE DESCRIPTION: SEQ ID NO: 62:

```
Ala Val Ser Glu His Gln Leu Leu His Asp Lys Gly Lys Ser Ile Gln
1               5                   10                  15

Asp Leu Arg Arg Arg Glu Leu Leu Glu Lys Leu Leu Glu Lys Leu His
            20                  25                  30

Thr Met Ala
        35
```

(2) INFORMATION FOR SEQ ID NO: 63:

(i) SEQUENCE CHARACTERISTICS:
        (A) LENGTH: 33 amino acids
        (B) TYPE: amino acid
        (D) TOPOLOGY: linear (ii) MOLECULE TYPE: protein (iii) HYPOTHETICAL: NO (v) FRAGMENT TYPE: N-terminal (ix) FEATURE:
    (A) NAME/KEY: Modified-site
    (B) LOCATION: 33
    (D) OTHER INFORMATION: /note= "Xaa is Thr
        1,4- diaminobutyryl lactam"

(xi) SEQUENCE DESCRIPTION: SEQ ID NO: 63:

```
Ala Val Ser Glu His Gln Leu Leu His Asp Lys Gly Lys Ser Ile Gln
1               5                   10                  15
Asp Leu Arg Arg Arg Glu Leu Leu Glu Lys Leu Leu Glu Lys Leu His
            20                  25                  30
Xaa
```

(2) INFORMATION FOR SEQ ID NO: 64:

(i) SEQUENCE CHARACTERISTICS:
        (A) LENGTH: 34 amino acids
        (B) TYPE: amino acid
        (D) TOPOLOGY: linear (ii) MOLECULE TYPE: protein (iii) HYPOTHETICAL: NO (v) FRAGMENT TYPE: N-terminal (xi) SEQUENCE DESCRIPTION: SEQ ID NO: 64:

```
Ala Val Ser Glu His Gln Leu Leu His Asp Lys Gly Lys Ser Ile Gln
1               5                   10                  15
Asp Leu Arg Arg Arg Phe Phe Leu Glu Lys Leu Leu Glu Lys Leu His
            20                  25                  30
Thr Ala
```

(2) INFORMATION FOR SEQ ID NO: 65:

(i) SEQUENCE CHARACTERISTICS:
        (A) LENGTH: 34 amino acids
        (B) TYPE: amino acid
        (D) TOPOLOGY: linear (ii) MOLECULE TYPE: protein (iii) HYPOTHETICAL: NO (v) FRAGMENT TYPE: N-terminal (xi) SEQUENCE DESCRIPTION: SEQ ID NO: 65:

```
Ala Val Ser Glu His Gln Leu Leu His Asp Lys Gly Lys Ser Ile Gln
1               5                   10                  15
Asp Leu Arg Arg Arg Glu Leu Leu His Lys Leu Leu Glu Lys Leu His
            20                  25                  30
Thr Ala
```

(2) INFORMATION FOR SEQ ID NO: 66:

(i) SEQUENCE CHARACTERISTICS:
        (A) LENGTH: 34 amino acids
        (B) TYPE: amino acid
        (D) TOPOLOGY: linear (ii) MOLECULE TYPE: protein (iii) HYPOTHETICAL: NO (v) FRAGMENT TYPE: N-terminal ( x i ) SEQUENCE DESCRIPTION: SEQ ID NO: 66:

| Ala | Val | Ser | Glu | His | Gln | Leu | Leu | His | Asp | Lys | Gly | Lys | Ser | Ile | Gln |
|-----|-----|-----|-----|-----|-----|-----|-----|-----|-----|-----|-----|-----|-----|-----|-----|
| 1 | | | | 5 | | | | | 10 | | | | | 15 | |

| Asp | Leu | Arg | Arg | Arg | Glu | Leu | Leu | Glu | His | Leu | Leu | Glu | Lys | Leu | His |
|-----|-----|-----|-----|-----|-----|-----|-----|-----|-----|-----|-----|-----|-----|-----|-----|
| | | | 20 | | | | | 25 | | | | | 30 | | |

Thr Ala ( 2 ) INFORMATION FOR SEQ ID NO: 67:

( i ) SEQUENCE CHARACTERISTICS:
        ( A ) LENGTH: 34 amino acids
        ( B ) TYPE: amino acid
        ( D ) TOPOLOGY: linear ( i i ) MOLECULE TYPE: protein ( i i i ) HYPOTHETICAL: NO ( v ) FRAGMENT TYPE: N-terminal ( x i ) SEQUENCE DESCRIPTION: SEQ ID NO: 67:

| Ala | Val | Ser | Glu | His | Gln | Leu | Leu | His | Asp | Lys | Gly | Lys | Ser | Ile | Gln |
|-----|-----|-----|-----|-----|-----|-----|-----|-----|-----|-----|-----|-----|-----|-----|-----|
| 1 | | | | 5 | | | | | 10 | | | | | 15 | |

| Asp | Leu | Arg | Arg | Arg | Glu | Leu | Leu | Glu | Lys | Leu | Ile | Ala | Lys | Leu | His |
|-----|-----|-----|-----|-----|-----|-----|-----|-----|-----|-----|-----|-----|-----|-----|-----|
| | | | 20 | | | | | 25 | | | | | 30 | | |

Thr Ala ( 2 ) INFORMATION FOR SEQ ID NO: 68:

( i ) SEQUENCE CHARACTERISTICS:
        ( A ) LENGTH: 34 amino acids
        ( B ) TYPE: amino acid
        ( D ) TOPOLOGY: linear ( i i ) MOLECULE TYPE: protein ( i i i ) HYPOTHETICAL: NO ( v ) FRAGMENT TYPE: N-terminal ( x i ) SEQUENCE DESCRIPTION: SEQ ID NO: 68:

| Ala | Val | Ser | Glu | His | Gln | Leu | Leu | His | Asp | Lys | Gly | Lys | Ser | Ile | Gln |
|-----|-----|-----|-----|-----|-----|-----|-----|-----|-----|-----|-----|-----|-----|-----|-----|
| 1 | | | | 5 | | | | | 10 | | | | | 15 | |

| Asp | Leu | Arg | Arg | Arg | Glu | Leu | Leu | Glu | Lys | Leu | Leu | Glu | Glu | Ile | His |
|-----|-----|-----|-----|-----|-----|-----|-----|-----|-----|-----|-----|-----|-----|-----|-----|
| | | | 20 | | | | | 25 | | | | | 30 | | |

Thr Ala ( 2 ) INFORMATION FOR SEQ ID NO: 69:

( i ) SEQUENCE CHARACTERISTICS:
        ( A ) LENGTH: 34 amino acids
        ( B ) TYPE: amino acid
        ( D ) TOPOLOGY: linear ( i i ) MOLECULE TYPE: protein ( i i i ) HYPOTHETICAL: NO ( v ) FRAGMENT TYPE: N-terminal ( i x ) FEATURE:
        ( A ) NAME/KEY: Modified-site
        ( B ) LOCATION: 34
        ( D ) OTHER INFORMATION: /note= "Xaa is homoserine"

( x i ) SEQUENCE DESCRIPTION: SEQ ID NO: 69:

```
Ala  Val  Ser  Glu  His  Gln  Leu  Leu  His  Asp  Lys  Gly  Lys  Ser  Ile  Gln
1               5                        10                        15

Asp  Leu  Arg  Arg  Arg  Glu  Leu  Leu  Glu  Lys  Leu  Leu  Glu  Lys  Leu  His
               20                        25                        30

Thr  Xaa
```

( 2 ) INFORMATION FOR SEQ ID NO: 70:

( i ) SEQUENCE CHARACTERISTICS:
        ( A ) LENGTH: 34 amino acids
        ( B ) TYPE: amino acid
        ( D ) TOPOLOGY: linear ( i i ) MOLECULE TYPE: protein ( i i i ) HYPOTHETICAL: NO ( v ) FRAGMENT TYPE: N-terminal ( i x ) FEATURE:
        ( A ) NAME/KEY: Modified-site
        ( B ) LOCATION: 34
        ( D ) OTHER INFORMATION: /note= "Xaa is homoserine"

( x i ) SEQUENCE DESCRIPTION: SEQ ID NO: 70:

```
Ala  Val  Ser  Glu  His  Gln  Leu  Leu  His  Asp  Lys  Gly  Lys  Ser  Ile  Gln
1               5                        10                        15

Asp  Leu  Arg  Arg  Arg  Glu  Leu  Leu  Glu  Lys  Leu  Leu  Glu  Lys  Leu  His
               20                        25                        30

Thr  Xaa
```

( 2 ) INFORMATION FOR SEQ ID NO: 71:

( i ) SEQUENCE CHARACTERISTICS:
        ( A ) LENGTH: 34 amino acids
        ( B ) TYPE: amino acid
        ( D ) TOPOLOGY: both ( i i ) MOLECULE TYPE: protein ( i i i ) HYPOTHETICAL: NO ( v ) FRAGMENT TYPE: N-terminal ( x i ) SEQUENCE DESCRIPTION: SEQ ID NO: 71:

```
Ala  Val  Ser  Glu  His  Gln  Leu  Leu  His  Asp  Lys  Gly  Lys  Ser  Ile  Gln
1               5                        10                        15

Asp  Leu  Arg  Arg  Arg  Glu  Leu  Leu  Glu  Lys  Leu  Leu  Glu  Lys  Leu  His
               20                        25                        30

Thr  Ala
```

( 2 ) INFORMATION FOR SEQ ID NO: 72:

( i ) SEQUENCE CHARACTERISTICS:
        ( A ) LENGTH: 37 amino acids
        ( B ) TYPE: amino acid
        ( D ) TOPOLOGY: linear ( i i ) MOLECULE TYPE: protein ( i i i ) HYPOTHETICAL: NO ( v ) FRAGMENT TYPE: N-terminal ( x i ) SEQUENCE DESCRIPTION: SEQ ID NO: 72:

```
Ala  Val  Ser  Glu  His  Gln  Leu  Leu  His  Asp  Lys  Gly  Lys  Ser  Ile  Gln
1               5                        10                        15
```

( 2 ) INFORMATION FOR SEQ ID NO: 73:

( i ) SEQUENCE CHARACTERISTICS:
        ( A ) LENGTH: 36 amino acids
        ( B ) TYPE: amino acid
        ( D ) TOPOLOGY: linear ( i i ) MOLECULE TYPE: protein ( i i i ) HYPOTHETICAL: NO ( v ) FRAGMENT TYPE: N-terminal ( i x ) FEATURE:
        ( A ) NAME/KEY: Modified-site
        ( B ) LOCATION: 36
        ( D ) OTHER INFORMATION: /note= "Xaa is Ala
            3-(2- naphthyl)-L-alanine"

( x i ) SEQUENCE DESCRIPTION: SEQ ID NO: 73:

```
Ala Val Ser Glu His Gln Leu Leu His Asp Lys Gly Lys Ser Ile Gln
1               5                   10                  15
Asp Leu Arg Arg Arg Glu Leu Leu Glu Lys Leu Leu Glu Lys Leu His
            20                  25                  30
Thr Arg Ser Xaa
            35
```

( 2 ) INFORMATION FOR SEQ ID NO: 74:

( i ) SEQUENCE CHARACTERISTICS:
        ( A ) LENGTH: 37 amino acids
        ( B ) TYPE: amino acid
        ( D ) TOPOLOGY: linear ( i i ) MOLECULE TYPE: protein ( i i i ) HYPOTHETICAL: NO ( v ) FRAGMENT TYPE: N-terminal ( x i ) SEQUENCE DESCRIPTION: SEQ ID NO: 74:

```
Ala Val Ser Glu His Gln Leu Leu His Asp Lys Gly Lys Ser Ile Gln
1               5                   10                  15
Asp Leu Arg Arg Arg Glu Leu Leu Glu Lys Leu Leu Glu Lys Leu His
            20                  25                  30
Thr Ala Ser Ala Trp
            35
```

( 2 ) INFORMATION FOR SEQ ID NO: 75:

( i ) SEQUENCE CHARACTERISTICS:
        ( A ) LENGTH: 38 amino acids
        ( B ) TYPE: amino acid
        ( D ) TOPOLOGY: linear ( i i ) MOLECULE TYPE: protein ( i i i ) HYPOTHETICAL: NO ( v ) FRAGMENT TYPE: N-terminal ( x i ) SEQUENCE DESCRIPTION: SEQ ID NO: 75:

```
Ala Val Ser Glu His Gln Leu Leu His Asp Lys Gly Lys Ser Ile Gln
1               5                   10                  15
```

Asp Leu Arg Arg Arg Glu Leu Leu Glu Lys Leu Leu Glu Lys Leu His
            20                      25                      30

Thr Ala Glu Ile Arg Ala
            35

( 2 ) INFORMATION FOR SEQ ID NO: 76:

( i ) SEQUENCE CHARACTERISTICS:
        ( A ) LENGTH: 37 amino acids
        ( B ) TYPE: amino acid
        ( D ) TOPOLOGY: linear ( i i ) MOLECULE TYPE: protein ( i i i ) HYPOTHETICAL: NO ( v ) FRAGMENT TYPE: N-terminal ( x i ) SEQUENCE DESCRIPTION: SEQ ID NO: 76:

Ala Val Ser Glu His Gln Leu Leu His Asp Lys Gly Lys Ser Ile Gln
1                   5                       10                      15

Asp Leu Arg Arg Arg Glu Leu Leu Glu Lys Leu Leu Glu Lys Leu His
            20                      25                      30

Thr Ala Glu Ile Arg
            35

( 2 ) INFORMATION FOR SEQ ID NO: 77:

( i ) SEQUENCE CHARACTERISTICS:
        ( A ) LENGTH: 36 amino acids
        ( B ) TYPE: amino acid
        ( D ) TOPOLOGY: linear ( i i ) MOLECULE TYPE: protein ( i i i ) HYPOTHETICAL: NO ( v ) FRAGMENT TYPE: N-terminal ( x i ) SEQUENCE DESCRIPTION: SEQ ID NO: 77:

Ala Val Ser Glu His Gln Leu Leu His Asp Lys Gly Lys Ser Ile Gln
1                   5                       10                      15

Asp Leu Arg Arg Arg Glu Leu Leu Glu Lys Leu Leu Glu Lys Leu His
            20                      25                      30

Thr Ala Glu Ile
            35

( 2 ) INFORMATION FOR SEQ ID NO: 78:

( i ) SEQUENCE CHARACTERISTICS:
        ( A ) LENGTH: 35 amino acids
        ( B ) TYPE: amino acid
        ( D ) TOPOLOGY: linear ( i i ) MOLECULE TYPE: protein ( i i i ) HYPOTHETICAL: NO ( v ) FRAGMENT TYPE: N-terminal ( x i ) SEQUENCE DESCRIPTION: SEQ ID NO: 78:

Ala Val Ser Glu His Gln Leu Leu His Asp Lys Gly Lys Ser Ile Gln
1                   5                       10                      15

Asp Leu Arg Arg Arg Glu Leu Leu Glu Lys Leu Leu Glu Lys Leu His
            20                      25                      30

Thr Ala Glu
         35

(2) INFORMATION FOR SEQ ID NO: 79:

(i) SEQUENCE CHARACTERISTICS:
       (A) LENGTH: 34 amino acids
       (B) TYPE: amino acid
       (D) TOPOLOGY: linear (ii) MOLECULE TYPE: peptide (iii) HYPOTHETICAL: NO (v) FRAGMENT TYPE: N-terminal (ix) FEATURE:
       (A) NAME/KEY: Modified-site
       (B) LOCATION: 8
       (D) OTHER INFORMATION: /note= "Leu8 is Norleucine"

(ix) FEATURE:
       (A) NAME/KEY: Modified-site
       (B) LOCATION: 18
       (D) OTHER INFORMATION: /note= "Leu18 is Norleucine"

(ix) FEATURE:
       (A) NAME/KEY: Modified-site
       (B) LOCATION: 34
       (D) OTHER INFORMATION: /note= "Xaa is homoserine lactone"

(xi) SEQUENCE DESCRIPTION: SEQ ID NO: 79:

Ala Val Ser Glu Ile Gln Phe Leu His Asn Lys Gly Lys His Leu Ser
   1               5                   10                  15
   Ser Leu Glu Arg Val Glu Trp Leu Arg Lys Lys Leu Gln Asp Val His
                   20                  25                  30
   Asn Xaa (2) INFORMATION FOR SEQ ID NO: 80:

(i) SEQUENCE CHARACTERISTICS:
       (A) LENGTH: 32 amino acids
       (B) TYPE: amino acid
       (D) TOPOLOGY: linear (ii) MOLECULE TYPE: protein (iii) HYPOTHETICAL: NO (v) FRAGMENT TYPE: internal (xi) SEQUENCE DESCRIPTION: SEQ ID NO: 80:

Ser Glu His Gln Leu Leu His Asp Lys Gly Lys Ser Ile Gln Asp Leu
   1               5                   10                  15
   Arg Arg Arg Glu Leu Leu Glu Lys Leu Leu Glu Lys Leu His Thr Ala
                   20                  25                  30

(2) INFORMATION FOR SEQ ID NO: 81:

(i) SEQUENCE CHARACTERISTICS:
       (A) LENGTH: 28 amino acids
       (B) TYPE: amino acid
       (D) TOPOLOGY: linear (ii) MOLECULE TYPE: protein (iii) HYPOTHETICAL: NO (v) FRAGMENT TYPE: internal (xi) SEQUENCE DESCRIPTION: SEQ ID NO: 81:

Leu Leu His Asp Lys Gly Lys Ser Ile Gln Asp Leu Arg Arg Arg Glu
1               5                   10                  15

Leu Leu Glu Lys Leu Leu Glu Lys Leu His Thr Ala
            20              25

(2) INFORMATION FOR SEQ ID NO: 82:

(i) SEQUENCE CHARACTERISTICS:
        (A) LENGTH: 27 amino acids
        (B) TYPE: amino acid
        (D) TOPOLOGY: linear (ii) MOLECULE TYPE: protein (iii) HYPOTHETICAL: NO (v) FRAGMENT TYPE: internal (xi) SEQUENCE DESCRIPTION: SEQ ID NO: 82:

Leu His Asp Lys Gly Lys Ser Ile Gln Asp Leu Arg Arg Arg Glu Leu
1               5                   10                  15

Leu Glu Lys Leu Leu Glu Lys Leu His Thr Ala
            20              25

(2) INFORMATION FOR SEQ ID NO: 83:

(i) SEQUENCE CHARACTERISTICS:
        (A) LENGTH: 41 amino acids
        (B) TYPE: amino acid
        (D) TOPOLOGY: linear (ii) MOLECULE TYPE: protein (iii) HYPOTHETICAL: NO (v) FRAGMENT TYPE: internal (xi) SEQUENCE DESCRIPTION: SEQ ID NO: 83:

Ser Glu His Gln Leu Leu His Asp Arg Gly Arg Ser Ile Gln Asp Leu
1               5                   10                  15

Arg Arg Arg Glu Leu Leu Glu Arg Leu Leu Glu Arg Leu His Leu His
            20                  25                  30

Arg Gly Arg Arg Thr Arg Ser Ala Trp
            35              40

(2) INFORMATION FOR SEQ ID NO: 84:

(i) SEQUENCE CHARACTERISTICS:
        (A) LENGTH: 35 amino acids
        (B) TYPE: amino acid
        (D) TOPOLOGY: linear (ii) MOLECULE TYPE: protein (iii) HYPOTHETICAL: NO (v) FRAGMENT TYPE: internal (xi) SEQUENCE DESCRIPTION: SEQ ID NO: 84:

Leu Leu His Asp Arg Gly Arg Ser Ile Gln Asp Leu Arg Arg Arg Glu
1               5                   10                  15

Leu Leu Glu Arg Leu Leu Glu Arg Leu His Ala Gly Arg Arg Thr Arg
            20                  25                  30

Ser Ala Trp
        35

(2) INFORMATION FOR SEQ ID NO:85:

( i ) SEQUENCE CHARACTERISTICS:
  ( A ) LENGTH: 10 amino acids
  ( B ) TYPE: amino acid
  ( D ) TOPOLOGY: linear ( i i ) MOLECULE TYPE: peptide ( i i i ) HYPOTHETICAL: NO ( v ) FRAGMENT TYPE: internal ( i x ) FEATURE:
  ( A ) NAME/KEY: Modified-site
  ( B ) LOCATION: 1 and 4
  ( D ) OTHER INFORMATION: /note= "Xaa1 and Xaa4 = Glu, Glu(OCH3), His, or Phe"

( i x ) FEATURE:
  ( A ) NAME/KEY: Modified-site
  ( B ) LOCATION: 2
  ( D ) OTHER INFORMATION: /note= "Xaa2 = Leu or Phe"

( i x ) FEATURE:
  ( A ) NAME/KEY: Modified-site
  ( B ) LOCATION: 5
  ( D ) OTHER INFORMATION: /note= "Xaa5 = Lys or His"

( i x ) FEATURE:
  ( A ) NAME/KEY: Modified-site
  ( B ) LOCATION: 7 and 10
  ( D ) OTHER INFORMATION: /note= "Xaa7 and Xaa10 = Leu or Ile"

( i x ) FEATURE:
  ( A ) NAME/KEY: Modified-site
  ( B ) LOCATION: 8
  ( D ) OTHER INFORMATION: /note= "Xaa8 = Ala, Arg, or Glu"

( i x ) FEATURE:
  ( A ) NAME/KEY: Modified-site
  ( B ) LOCATION: 9
  ( D ) OTHER INFORMATION: /note= "Xaa9 = Lys or Glu"

( x i ) SEQUENCE DESCRIPTION: SEQ ID NO:85:

Xaa Xaa Leu Xaa Xaa Leu Xaa Xaa Xaa Xaa
1             5                   10

( 2 ) INFORMATION FOR SEQ ID NO:86:

( i ) SEQUENCE CHARACTERISTICS:
    ( A ) LENGTH: 10 amino acids
    ( B ) TYPE: amino acid
    ( D ) TOPOLOGY: linear ( i i ) MOLECULE TYPE: peptide ( i i i ) HYPOTHETICAL: NO ( v ) FRAGMENT TYPE: internal ( i x ) FEATURE:
    ( A ) NAME/KEY: Modified-site
    ( B ) LOCATION: 1 and 4
    ( D ) OTHER INFORMATION: /note= "Xaa1 and Xaa4 = Glu, Glu(OCH3), His, or Phe"

( i x ) FEATURE:
    ( A ) NAME/KEY: Modified-site
    ( B ) LOCATION: 2
    ( D ) OTHER INFORMATION: /note= "Xaa2 = Leu or Phe"

( i x ) FEATURE:
    ( A ) NAME/KEY: Modified-site
    ( B ) LOCATION: 8
    ( D ) OTHER INFORMATION: /note= "Xaa8 = Glu, Lys or Lys(COCH2PEGX)"

-continued ( x i ) SEQUENCE DESCRIPTION: SEQ ID NO:86:

Xaa Xaa Leu Xaa Arg Leu Leu Xaa Arg Leu
1               5                    1 0